2010.

United States Patent
Kotton et al.

(10) Patent No.: US 11,366,115 B2
(45) Date of Patent: *Jun. 21, 2022

(54) ISOLATION OF HUMAN LUNG PROGENITORS DERIVED FROM PLURIPOTENT STEM CELLS

(71) Applicant: TRUSTEES OF BOSTON UNIVERSITY, Boston, MA (US)

(72) Inventors: Darrell N. Kotton, Newton, MA (US); Finn Hawkins, Boston, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 244 days.

This patent is subject to a terminal disclaimer.

(21) Appl. No.: 16/460,461

(22) Filed: Jul. 2, 2019

(65) Prior Publication Data
US 2020/0003776 A1    Jan. 2, 2020

Related U.S. Application Data

(62) Division of application No. 15/902,614, filed on Feb. 22, 2018, now Pat. No. 10,386,368.

(60) Provisional application No. 62/463,184, filed on Feb. 24, 2017.

(51) Int. Cl.
| | |
|---|---|
| *G01N 33/569* | (2006.01) |
| *A61K 35/42* | (2015.01) |
| *C12N 5/071* | (2010.01) |
| *A61K 9/00* | (2006.01) |
| *A61K 9/19* | (2006.01) |

(52) U.S. Cl.
CPC ....... *G01N 33/56966* (2013.01); *A61K 35/42* (2013.01); *C12N 5/0689* (2013.01); *A61K 9/007* (2013.01); *A61K 9/19* (2013.01); *C12N 2501/117* (2013.01); *C12N 2501/119* (2013.01); *C12N 2501/155* (2013.01); *C12N 2501/599* (2013.01); *C12N 2501/999* (2013.01); *C12N 2506/04* (2013.01); *C12N 2506/45* (2013.01); *G01N 2333/4703* (2013.01); *G01N 2333/70596* (2013.01)

(58) Field of Classification Search
CPC ... G01N 33/56966; G01N 2333/70596; A61K 35/42; C12N 5/0689
See application file for complete search history.

(56) References Cited

U.S. PATENT DOCUMENTS

| | | |
|---|---|---|
| 2010/0266552 A1 | 10/2010 | Jenkin |
| 2011/0212067 A1 | 9/2011 | Karanu |
| 2013/0230921 A1 | 9/2013 | Keller |
| 2014/0329318 A1 | 11/2014 | Rajagopal |
| 2016/0200816 A1 | 7/2016 | Jaiswal |
| 2016/0363591 A1 | 12/2016 | Stricher |

OTHER PUBLICATIONS

Ikonomou et al. The in vivo genetic program of murine primordial lung epithelial progenitors. Nature Communications (2020) 11:635, p. 1-17 (Year: 2020).*
Ghaedi et al., "Development of Lung Epithelium from Induced Pluripotent Stem Cells", Curr Transplant Rep 2(1) 81-89 (2015).
Green et al., "Generation of anterior foregut endoderm from human embryonic and induced pluripotent stem cells", Nat Biotechnol 29(3) 267-272 (2011).
Hawkins et al., "Prospective isolation of NKX2-1-expressing human lung progenitors derived from pluripotent stem cells", J Clin Invest 127(6) 2277-2294 (2017).
Jacob et al., "Differentiation of Human Pluripotent Stem Cells into Functional Lung Alveolar Epithelial Cells", Cell Stem Cell 21(4) 472-488 (2017).
Jaiswal et al., "CD47 is upregulated on circulating hematopoietic stem cells and leukemia cells to avoid phagocytosis", Cell 138(2) 271-285 (2009).
Dye et al., "In vitro generation of human pluripotent stem cell derived lung organoids", Elife 24: 4 (2015).
Gotoh et al., "Generation of alveolar epithelial spheroids via isolated progenitor cells from human pluripotent stem cells", Stem Cell Reports 3(3) 394-403 (2014).
Guo et al., "Resolution of cell fate decisions revealed by single-cell gene expression analysis from zygote to blastocyst", Dev Cell 18(4) 675-685 (2010).
Hawkins et al., "Embryonic and induced pluripotent stem cells for lung regeneration", Ann Am Thorac Sco 12(Suppls 1) S50-S53 (2015).
Herriges et al., "Genome-scale study of transcription factor expression in the branching mouse lung", Dev Dyn 241(9) 1432-1453 (2012).
Herriges et al., "Long noncoding RNAs are spatially correlated with transcription factors and regulate lung development", Genes Dev 28(12) 1363-1379 (2014).
Herriges et al., "Lung development: orchestrating the generation and regeneration of a complex organ", Development 141(3) 502-513 (2014).
Huang et al., "Efficient generation of lung and airway epithelial cells from human pluripotent stem cells", Nat Biotechnol 32(1) 84-91 (2014).
Kho et al., "Transcriptomic analysis of human lung development", Am J Respir Crit Care Med 181(1) 54-63 (2010).
Klemann et al. "Cut to the chase: a review of CD26/dipeptidyl peptidase-4's (DPP4) entanglement in the immune system." Clinical & Experimental Immunology 185(1):1-21 (2016).
Longmire et al., "Efficient derivation of purified lung and thyroid progenitors from embryonic stem cells", Cell Stem Cell 10(4) 398-411 (2012).
Maeda et al., "Transcriptional control of lung morphogenesis", Physiol Rev 87(1) 219-244 (2007).

(Continued)

*Primary Examiner* — Taeyoon Kim
(74) *Attorney, Agent, or Firm* — Nixon Peabody LLP; Ronald I. Eisenstein; Nicole D. Kling

(57) ABSTRACT

Provided herein are methods and compositions relating, in part, to the generation and isolation of human lung progenitor cells from pluripotent stem cells.

7 Claims, 44 Drawing Sheets
(44 of 44 Drawing Sheet(s) Filed in Color)
Specification includes a Sequence Listing.

(56) References Cited

OTHER PUBLICATIONS

Millien et al., "Characterization of the mid-foregut transcriptome identifies genes regulated during lung bud induction", Gene Expr Patterns 8(2) 124-139 (2008).
Mou et al., "Generation of multipotent lung and airway progenitors from mouse ESCs and patient-specific cystic fibrosis iPSCs", Cell Stem Cell 10(4) 385-397 (2012).
Oldenborg "CD47: a cell surface glycoprotein which regulates multiple functions of hematopoietic cells in health and disease." ISRN Hematology 2013(614619):1-19 (2013).
Shannon et al., "Mesenchyme specifies epithelial differentiation in reciprocal recombinants of embryonic lung and trachea", Dev Dyn 212(4) 482-494 (1998).
Van Haute et al., "Generation of lung epithelial-like tissue from human embryonic stem cells", Respir Res 10: 105 (2009).
Wang et al., "A pure population of lung alveolar epithelial type II cells derived from human embryonic stem cells", Proc Natl Acad Sci USA 104(11) 4449-4454 (2007).
Wong et al., "Directed differentiation of human pluripotent stem cells into mature airway epithelia expressing functional CFTR protein", Nat Biotechnol 30(9) 876-882 (2012).

\* cited by examiner

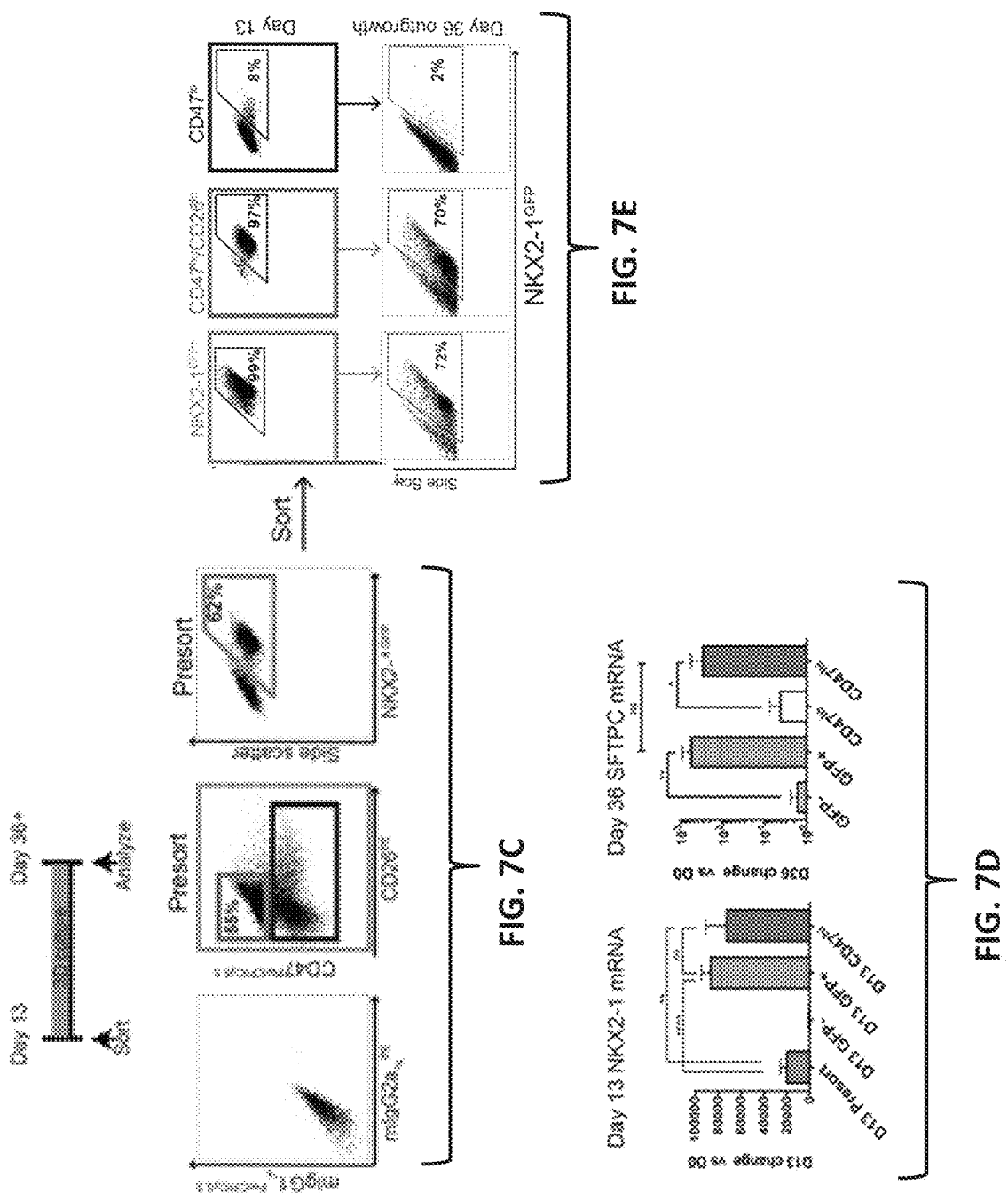

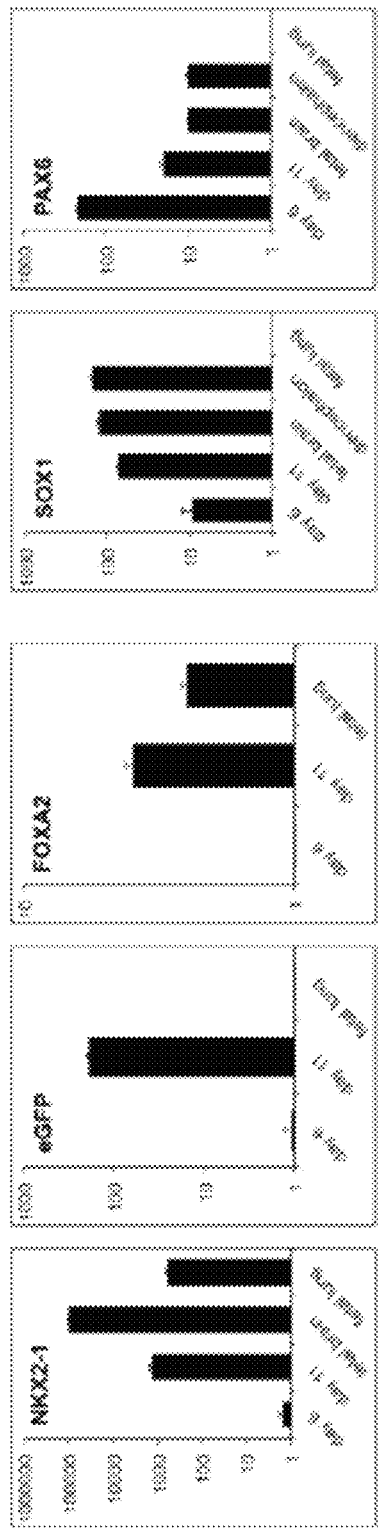
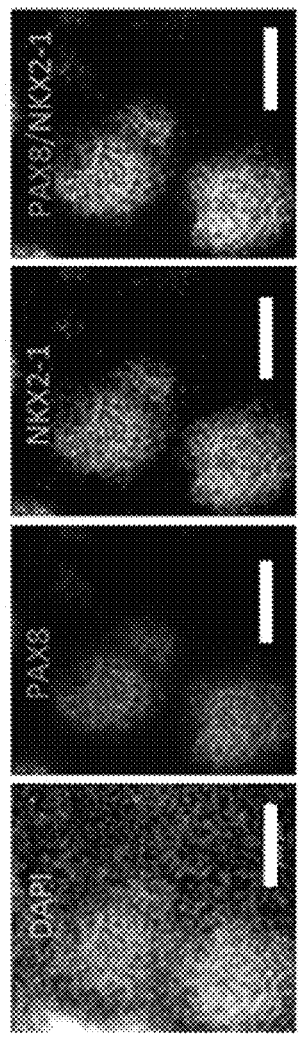
FIG. 9C
FIG. 9D

SEQUENCE LISTING

```
<160> NUMBER OF SEQ ID NOS: 6

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Asp Gly Cys Glu Leu
1               5

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tcgagcgccc ggcccgg                                                 17

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agtctgggca ggtggga                                                 17

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gccctctctc cagcggagtc                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gactctaagg gtccgagcag                                              20

<210> SEQ ID NO 6
<211> LENGTH: 20
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 6
gagaccggta agcgacaaac                                              20
```

ISOLATION OF HUMAN LUNG PROGENITORS DERIVED FROM PLURIPOTENT STEM CELLS

CROSS REFERENCE TO RELATED APPLICATIONS

This application is a Divisional application which claims the benefit of U.S. Utility application Ser. No. 15/902,614, filed Feb. 22, 2018, which claims benefit under 35 U.S.C. § 119(e) of U.S. Provisional Application No. 62/463,184 filed Feb. 24, 2017, the contents of which are incorporated herein by reference in their entirety.

GOVERNMENT SUPPORT

This invention was made with Government Support under Contract No. HL095993 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Apr. 4, 2018, is named 701586-088671-US_SL.txt and is 1,674 bytes in size.

FIELD OF THE INVENTION

The field of the invention relates to methods for isolating human lung progenitor cells using cell surface markers.

BACKGROUND

Current treatments for lung and respiratory diseases are mainly directed at reducing symptoms of disease, rather than treating the disease itself. However, transplantation of lung progenitor cells may be able to regenerate endogenous lung cells that were previously destroyed by injury or disease.

While stem cell treatment of lung disease is highly desired, isolation of lung progenitor cells from the adult human lung has proved to be a difficult task, despite much effort by the scientific community. One approach to address this issue is to reprogram an autologous cell to an induced pluripotent stem cell, and then induce directed differentiation to lung progenitor cells. This approach also has the advantages of permitting manipulation to the cell prior to administration and preventing rejection of the cells by the subject.

SUMMARY

The methods and compositions provided herein are based, in part, on the detection and/or isolation of lung progenitor ("primordial") cells based on the expression (or lack thereof) of cell surface markers that make up the cell surface phenotype. In one embodiment, methods are provided herein for isolating lung progenitor cells from a population of cells by isolating cells expression $CD47^{hi}$ and/or $CD26^{lo}$.

Accordingly, provided herein in one aspect is a method for isolating a lung progenitor cell, the method comprising: contacting a pluripotent stem cell population with at least one differentiation-inducing agent, and sorting one or more cells having high expression of CD47 ($CD47^{hi}$) from the pluripotent stem cell population, thereby isolating one or more lung progenitor cells.

In one embodiment of this aspect and all other aspects described herein, the method further comprises sorting the population for low CD26 expression ($CD26^{lo}$), such that an isolated population of $CD47^{hi}/CD26^{lo}$ lung progenitor cells is isolated.

In another embodiment of this aspect and all other aspects described herein, the at least one differentiation-inducing agent comprises at least one of CHIR 99021, BMP4, KGF, FGF10, and retinoic acid.

In one embodiment, the concentration of CHIR 99021 used with the methods of generating primordial lung progenitors as described herein comprises at least 0.5 µM, at least 1 µM, at least 1.5 µM, at least 2 µM, at least 2.5 µM, at least 3 µM, at least 3.5 µM, at least 4 µM, at least 4.5 µM, at least 5 µM, at least 10 µM, at least 20 µM or more. In another embodiment, the concentration of CHIR 99021 used with the methods of generating primordial lung progenitors as described herein comprises a concentration in the range of 1-5 µM, 1-10 µM, 1-20 µM, 2-4 µM, 5-20 µM, 10-20 µM, or any range therebetween.

In another embodiment, the concentration of BMP4 used with the methods of generating primordial lung progenitors as described herein comprises at least 1 ng/mL, at least 2 ng/mL, at least 3 ng/mL, at least 4 ng/mL, at least 5 ng/mL, at least 6 ng/mL, at least 7 ng/mL, at least 8 ng/mL, at least 9 ng/mL, at least 10 ng/mL, at least 11 ng/mL, at least 12 ng/mL, at least 13 ng/mL, at least 14 ng/mL, at least 15 ng/mL, at least 20 ng/mL, at least 30 ng/mL, at least 40 ng/mL, at least 50 ng/mL, at least 60 ng/mL, at least 75 ng/mL, at least 100 ng/mL, at least 125 ng/mL, at least 150 ng/mL, at least 200 ng/mL or more. In another embodiment, the concentration of BMP4 used with the methods of generating primordial lung progenitors as described herein comprises a concentration in the range of 1-50 ng/mL, 1-25 ng/mL, 1-10 ng/mL, 5-10 ng/mL, 5-15 ng/mL, 5-25 ng/mL, 25-50 ng/mL, 25-75 ng/mL, 25-100 ng/mL, 25-150 ng/mL, 75-125 ng/mL or any range therebetween.

In another embodiment, the concentration of KGF used with the methods of generating primordial lung progenitors as described herein comprises at least 1 ng/mL, at least 2 ng/mL, at least 3 ng/mL, at least 4 ng/mL, at least 5 ng/mL, at least 6 ng/mL, at least 7 ng/mL, at least 8 ng/mL, at least 9 ng/mL, at least 10 ng/mL, at least 11 ng/mL, at least 12 ng/mL, at least 13 ng/mL, at least 14 ng/mL, at least 15 ng/mL, at least 20 ng/mL, at least 30 ng/mL, at least 40 ng/mL, at least 50 ng/mL, or more. In another embodiment, the concentration of KGF used with the methods of generating primordial lung progenitors as described herein comprises a concentration in the range of 1-50 ng/mL, 1-25 ng/mL, 1-10 ng/mL, 5-10 ng/mL, 5-15 ng/mL, 10-20 ng/mL, 5-25 ng/mL, or any range therebetween.

In another embodiment, the concentration of FGF10 used with the methods of generating primordial lung progenitors as described herein comprises at least 1 ng/mL, at least 2 ng/mL, at least 3 ng/mL, at least 4 ng/mL, at least 5 ng/mL, at least 6 ng/mL, at least 7 ng/mL, at least 8 ng/mL, at least 9 ng/mL, at least 10 ng/mL, at least 11 ng/mL, at least 12 ng/mL, at least 13 ng/mL, at least 14 ng/mL, at least 15 ng/mL, at least 20 ng/mL, at least 30 ng/mL, at least 40 ng/mL, at least 50 ng/mL, or more. In another embodiment, the concentration of FGF10 used with the methods of generating primordial lung progenitors as described herein comprises a concentration in the range of 1-50 ng/mL, 1-25 ng/mL, 1-10 ng/mL, 5-10 ng/mL, 5-15 ng/mL, 10-20 ng/mL, 5-25 ng/mL, or any range therebetween.

In one embodiment, the concentration of retinoic acid used with the methods of generating primordial lung progenitors as described herein comprises at least 0.5 µM, at least 1 µM, at least 5 µM, at least 25 µM, at least 40 µM, at least 50 µM, at least 60 µM, at least 70 µM, at least 75 µM, at least 80 µM, at least 90 µM, at least 100 µM, at least 125 µM, at least 150 µM, at least 200 µM or more. In another embodiment, the concentration of retinoic acid used with the methods of generating primordial lung progenitors as described herein comprises a concentration in the range of 1-150 µM, 1-100 µM, 1-50 µM, 25-75 µM, 40-60 µM, 50-100 µM, 50-75 µM, 40-75 µM, 75-10 µM, 50-125 µM, 75-125 µM, or any range therebetween.

In another embodiment of this aspect and all other aspects described herein, the pluripotent stem cell population is comprised by a tissue.

In another embodiment of this aspect and all other aspects described herein, the pluripotent stem cell population is derived from embryonic stem cells or induced pluripotent stem cells (IPSCs) in vitro.

In another embodiment of this aspect and all other aspects described herein, the method further comprises a step of comparing the level of expression of CD47 and/or CD26 with a reference.

In another embodiment of this aspect and all other aspects described herein, the expression of CD47 and/or CD26 is measured using antibody that binds to either CD47 and/or CD26.

In another embodiment of this aspect and all other aspects described herein, the lung progenitor cell also expresses NKX2-1.

In another embodiment of this aspect and all other aspects described herein, the lung progenitor cell can be differentiated to: (a) a maturing alveolar epithelial cell comprising expression of ETV5, CLDN18, LPCAT1, MUC1, SFTPB, and/or low SFTPC, (b) a basal cell comprising expression of TP63, (c) a secretory cell comprising expression of SCGB3A2, MUC5B, MUC5AC, and/or AGR2, (d) a ciliated cell comprising expression of FOXJ1, and/or CFTR, and/or (e) a pulmonary neuroendocrine cell comprising expression of ASCL1.

In another embodiment of this aspect and all other aspects described herein, the lung progenitor cell does not express mature lung markers.

In another embodiment of this aspect and all other aspects described herein, the mature lung markers are selected from the group consisting of: lowSCG1A1, SCGB3A2, TP63, SFTPB, and/or SFTPC.

In another embodiment of this aspect and all other aspects described herein, the lung progenitor cell can be separated from neuronal cell precursors by measuring increased expression of one or more transcriptional markers selected from the group consisting of: GRHL2, ELF3, GATA6, HNF1B, HOXA1 and FOXA1.

In another embodiment of this aspect and all other aspects described herein, increased expression of all of the transcriptional markers is measured.

In another embodiment of this aspect and all other aspects described herein, the lung progenitor cell further expresses SFTA3, CPM, NFIB, NKX2-1, CRH, JUN, MECOM, SOX2, HES1, HOXA1, FOXA2, FOXA1, GATA6, GRHL2, IRX1, IRX2, ELF3, ELF5, HNFIB, FOXP2, HOXA4, HOXC4, SHH, EPCAM, CD166, CD227, SOX2, SOX9, and/or LAMA2.

In another embodiment of this aspect and all other aspects described herein, the lung progenitor cell further comprises expression of NKX2-1, SFTA3, CPM, and LAMA3.

In another embodiment of this aspect and all other aspects described herein, the lung progenitor cell does not express SCGB3A2, SFTPB, TP63, ICAM1, IL8, ASCL1, FOXJ1, SCGB1A1, ITGB6, SIX3, SIX6, OTX1 or PAX8.

In another embodiment of this aspect and all other aspects described herein, the lung progenitor cell is sorted using fluorescence-activated cell sorting (FACS).

Another aspect provided herein relates to a method for isolating a lung progenitor cell, the method comprising: (a) contacting a population of pluripotent cells with a first binding reagent that recognizes CD47 and a second binding reagent that recognizes CD26 to determine the level of expression of CD47 and CD26, and (b) isolating at least one cell with a cell surface phenotype comprising $CD47^{hi}$/$CD26^{lo}$, thereby isolating a lung progenitor cell from the population of pluripotent cells.

Another aspect provided herein relates to a method for isolating a lung progenitor cell, the method comprising: (a) contacting a population of cells with an antibody that recognizes CD47 and a second antibody that recognizes CD26 to determine the level of expression of CD47 and CD26, and (b) isolating at least one cell with a cell surface phenotype comprising expression levels of CD47 that is at least one standard deviation greater than the expression levels of CD47 in a control cell ($CD47^{hi}$) and comprising expression levels of CD26 that is at least one standard deviation greater than the expression levels of CD26 in a control cell ($CD26^{lo}$), thereby isolating a lung progenitor cell from the population of cells. It is specifically contemplated herein that an antibody or binding reagent used to detect levels of CD47 are selective for CD47 and that an antibody or binding reagent used to detect levels of CD26 are selective for CD26. That is, an antibody or binding reagent that binds CD47 does not bind or recognize CD26 and vice versa.

In one embodiment of this aspect and all other aspects described herein, the first and/or second binding reagent comprises an antibody or a fragment thereof.

In another embodiment of this aspect and all other aspects described herein, the population of pluripotent cells is comprised by a tissue.

In another embodiment of this aspect and all other aspects described herein, the population of pluripotent cells is derived from embryonic stem cells or induced pluripotent stem cells (IPSCs) in vitro.

In another embodiment of this aspect and all other aspects described herein, the method further comprises a step of comparing the level of expression of CD47 and/or CD26 with a reference.

In another embodiment of this aspect and all other aspects described herein, the lung progenitor cell also expresses NKX2-1.

In another embodiment of this aspect and all other aspects described herein, the lung progenitor cell can be differentiated to: (a) a maturing alveolar epithelial cell comprising expression of ETV5, CLDN18, LPCAT1, MUC1, SFTPB, and/or low SFTPC, (b) a basal cell comprising expression of TP63, (c) a secretory cell comprising expression of SCGB3A2, MUC5B, MUC5AC, and/or AGR2, (d) a ciliated cell comprising expression of FOXJ1, and/or CFTR, and/or (e) a pulmonary neuroendocrine cell comprising expression of ASCL1.

In another embodiment of this aspect and all other aspects described herein, the lung progenitor cell does not express mature lung markers.

In another embodiment of this aspect and all other aspects described herein, the mature lung markers are selected from the group consisting of: lowSCG1A1, SCGB3A2, TP63, SFTPB, and/or SFTPC.

In another embodiment of this aspect and all other aspects described herein, the lung progenitor cell can be separated from neuronal cell precursors by measuring increased expression of one or more transcriptional markers selected from the group consisting of: GRHL2, ELF3, GATA6, HNF1B, HOXA1 and FOXA1.

In another embodiment of this aspect and all other aspects described herein, increased expression of all of the transcriptional markers is measured.

In another embodiment of this aspect and all other aspects described herein, the lung progenitor cell further expresses SFTA3, CPM, NFIB, NKX2-1, CRH, JUN, MECOM, SOX2, HES1, HOXA1, FOXA2, FOXA1, GATA6, GRHL2, IRX1, IRX2, ELF3, ELF5, HNFIB, FOXP2, HOXA4, HOXC4, SHH, EPCAM, CD166, CD227, SOX2, SOX9, and/or LAMA2.

In another embodiment of this aspect and all other aspects described herein, the lung progenitor cell comprises expression of NKX2-1, SFTA3, CPM, and LAMA3.

In another embodiment of this aspect and all other aspects described herein, the lung progenitor cell does not express SCGB3A2, SFTPB, TP63, ICAM1, IL8, ASCL1, FOXJ1, SCGB1A1, ITGB6, SIX3, SIX6, OTX1 or PAX8.

In another embodiment of this aspect and all other aspects described herein, the lung progenitor cell is isolated using fluorescence-activated cell sorting (FACS).

In another embodiment of this aspect and all other aspects described herein, the population of cells is cultured without mesenchymal co-culture support.

Another aspect provided herein relates to a composition comprising: a population of CD47$^{hi}$/CD26$^{lo}$ lung progenitor cells isolated by the methods described herein and a pharmaceutically acceptable carrier.

In one embodiment of this aspect and all other aspects described herein, the composition further comprises a scaffold.

In another embodiment of this aspect and all other aspects described herein, the scaffold is biodegradable.

In another embodiment of this aspect and all other aspects described herein, the scaffold is a decellularized lung.

In another embodiment of this aspect and all other aspects described herein, the population of CD47$^{hi}$/CD26$^{lo}$ lung progenitor cells is at least 90% pure.

In another embodiment of this aspect and all other aspects described herein, the lung progenitor cell also expresses NKX2-1.

In another embodiment of this aspect and all other aspects described herein, the lung progenitor cell does not express mature lung markers. In one embodiment, the mature lung markers are selected from the group consisting of: lowSCG1A1, SCGB3A2, TP63, SFTPB, and/or SFTPC.

In another embodiment of this aspect and all other aspects described herein, the lung progenitor cell can be separated from neuronal cell precursors by measuring increased expression of one or more transcriptional markers selected from the group consisting of: GRHL2, ELF3, GATA6, HNF1B, HOXA1 and FOXA1.

In another embodiment of this aspect and all other aspects described herein, wherein increased expression of all of the transcriptional markers is measured.

In another embodiment of this aspect and all other aspects described herein, wherein the lung progenitor cell further expresses SFTA3, CPM, NFIB, NKX2-1, CRH, JUN, MECOM, SOX2, HES1, HOXA1, FOXA2, FOXA1, GATA6, GRHL2, IRX1, IRX2, ELF3, ELF5, HNFIB, FOXP2, HOXA4, HOXC4, SHH, EPCAM, CD166, CD227, SOX2, SOX9, and/or LAMA2.

In another embodiment of this aspect and all other aspects described herein, the lung progenitor cell comprises expression of NKX2-1, SFTA3, CPM, and LAMA3.

In another embodiment of this aspect and all other aspects described herein, the lung progenitor cell does not express SCGB3A2, SFTPB, TP63, ICAM1, IL8, ASCL1, FOXJ1, SCGB1A1, ITGB6, SIX3, SIX6, OTX1 or PAX8.

In another embodiment of this aspect and all other aspects described herein, the cell is engineered to comprise at least one modification. In one embodiment, the modification comprises a genomic modification or insertion of a non-integrating vector. In another embodiment, the genomic modification comprises: a point mutation, a deletion, an insertion, or a frame-shift mutation.

In another embodiment of this aspect and all other aspects described herein, the genomic modification introduces, removes, repairs and/or corrects a nucleic acid encoding a desired gene product.

Another aspect provided herein relates to a method for treating a lung disease or disorder, the method comprising: administering a composition comprising a population of CD47$^{hi}$/CD26$^{lo}$ lung progenitor cells to a subject in need thereof.

In another embodiment of this aspect and all other aspects described herein, the lung progenitor cells are derived from embryonic stem cells or induced pluripotent stem cells.

In another embodiment of this aspect and all other aspects described herein, the lung progenitor cells are autologous cells.

In another embodiment of this aspect and all other aspects described herein, the composition further comprises a pharmaceutically acceptable carrier.

In another embodiment of this aspect and all other aspects described herein, the composition further comprises a bioactive agent.

In another embodiment of this aspect and all other aspects described herein, the composition further comprises a scaffold. In one embodiment, the scaffold is biodegradable.

In another embodiment of this aspect and all other aspects described herein, the population of lung progenitor cells is at least 90% pure.

In another embodiment of this aspect and all other aspects described herein, the composition is formulated for delivery to the lungs.

In another embodiment of this aspect and all other aspects described herein, the composition is formulated for aerosol delivery.

In another embodiment of this aspect and all other aspects described herein, the lung progenitor cell also expresses NKX2-1.

In another embodiment of this aspect and all other aspects described herein, the lung progenitor cell does not express mature lung markers. In one embodiment, the mature lung markers are selected from the group consisting of: lowSCG1A1, SCGB3A2, TP63, SFTPB, and/or SFTPC.

In another embodiment of this aspect and all other aspects described herein, the lung progenitor cell can be separated from neuronal cell precursors by measuring increased expression of one or more transcriptional markers selected from the group consisting of: GRHL2, ELF3, GATA6, HNF1B, HOXA1 and FOXA1.

In another embodiment of this aspect and all other aspects described herein, increased expression of all of the transcriptional markers is measured.

In another embodiment of this aspect and all other aspects described herein, the lung progenitor cell further expresses SFTA3, CPM, NFIB, NKX2-1, CRH, JUN, MECOM, SOX2, HES1, HOXA1, FOXA2, FOXA1, GATA6, GRHL2, IRX1, IRX2, ELF3, ELF5, HNFIB, FOXP2, HOXA4, HOXC4, SHH, EPCAM, CD166, CD227, SOX2, SOX9, and/or LAMA2.

In another embodiment of this aspect and all other aspects described herein, the lung progenitor cell comprises expression of NKX2-1, SFTA3, CPM, and LAMA3.

In another embodiment of this aspect and all other aspects described herein, the lung progenitor cell does not express SCGB3A2, SFTPB, TP63, ICAM1, IL8, ASCL1, FOXJ1, SCGB1A1, ITGB6, SIX3, SIX6, OTX1 or PAX8.

In another embodiment of this aspect and all other aspects described herein, the cell is engineered to comprise at least one modification. In one embodiment, the modification comprises a genomic modification or insertion of a non-integrating vector. In another embodiment, the genomic modification comprises: a point mutation, a deletion, an insertion, or a frame-shift mutation. In another embodiment, the genomic modification introduces, removes, repairs and/or corrects a nucleic acid encoding a desired gene product.

Another aspect provided herein relates to a method for generating autologous lung progenitor cells, the method comprising: (a) reprogramming a somatic cell obtained from a subject to an induced pluripotent stem cell, (b) differentiating the induced pluripotent stem cell to an anterior foregut-like endoderm cell, (c) culturing the anterior foregut-like endoderm cell in the presence of CHIR 99021, BMP4, KGF, FGF10, and retinoic acid each for a time and at a concentration sufficient to induce differentiation along the lung lineage, and (d) isolating cells having a cell surface phenotype comprising $CD47^{hi}/CD26^{lo}$, thereby generating autologous lung progenitor cells for the subject.

In one embodiment of this aspect and all other aspects described herein, the method further comprises a step of formulating the autologous lung progenitor cells for administration to the lung(s) of the subject.

In another embodiment of this aspect and all other aspects provided herein, the method provides standardized generation and isolation of the lung progenitor cells derived from iPSCs.

In another embodiment of this aspect and all other aspects provided herein, the somatic cells, induced pluripotent stem cells, embryonic stem cells, lung progenitor cells and/or differentiated lung cells are each human cells.

Another aspect provided herein relates to a kit for generating lung progenitor cells comprising: (a) a reagent that binds CD47, (b) a reagent that binds CD26, and (c) instructions for generating lung progenitor cells therefor.

In one embodiment of this aspect and all other aspects described herein, the kit further comprises one or more reagents for generating lung progenitor cells from anterior foregut endoderm cells, wherein the one or more reagents is selected from the group consisting of: CHIR 99021, BMP4, KGF, FGF10, and retinoic acid.

In another embodiment of this aspect and all other aspects provided herein, the kit comprises reagent for generating lung progenitor cells in standardized concentrations and/or dosages, wherein the standardized concentration and/or dosages permit the reproducible and consistent isolation of lung progenitor cells from non-lung progenitor cells.

BRIEF DESCRIPTION OF THE FIGURES

The patent or application file contains at least one drawing executed in color. Copies of this patent or patent application publication with color drawing(s) will be provided by the Office upon request and payment of the necessary fee.

(FIG. 1A) Gene editing strategy based on TALENs technology to target a GFP reporter to the human NKX2-1 locus to engineer NKX2-1$^{GFP}$ iPSC/ESC lines. See also FIG. 8. (FIG. 1B) Schematic overview of in vitro directed differentiation of ESC/iPSC into NKX2-1+ lineages: endodermal lung or thyroid epithelia vs. ectodermal forebrain. (FIG. 1C) Representative timeline of GFP expression measured by flow cytometry during lung directed differentiation (C17). (FIG. 1D) Immunostaining of day 15 lung directed differentiation for NKX2-1, GFP (anti-GFP) and EPCAM (scale bars=100 μm) with zoom in (white dashed-line box) (C17). (FIG. 1E) Phase contrast and fluorescence microscopy of C17 iPSC-derived cells generated in the lung (day 15), thyroid (day 27) and forebrain (day 10) protocols. See also FIG. 9. (FIG. 1F) Flow cytometric analysis of lung (day 15), thyroid (day 17) and forebrain (day 14) protocols. (FIG. 1G) Fold change, compared to day 0, of mRNA expression of sorted NKX2-1$^{GFP+}$ and NKX2-1$^{GFP-}$ cells from those time points by RT-qPCR; quantified as $2^{(-\Delta\Delta CT)}$, n=3 (C17).

(FIG. 2A) Schematic overview of organoid generation with representative phase contrast and GFP fluorescence microscopy images (day 25-28) as well as immunostainings (day 36) for NKX2-1 and EPCAM proteins. Cell nuclei are counterstained with DAPI. Each panel shows outgrowth in 3D culture of structures arising from iPSC-derived cells that were either unsorted or sorted on day 15 as GFP+vs. GFP− populations. Scale bar left and center columns=100 μm, scale bar right sided column=20 μm. (FIG. 2B) Time lapse microscopy (merged GFP fluorescence and phase contrast) of unsorted organoids over 25 hours. Arrows indicate epithelial organoids undergoing induction of the GFP reporter in real time. (FIG. 2C) Flow cytometry quantification on day 36 of the percentage of cells expressing GFP in the outgrowth wells shown in FIG. 2A. Data indicate individual biological replicates (squares and triangles) with mean±SD. Fold change [RT-qPCR; $2^{(-\Delta\Delta CT)}$] in mRNA expression on day 36 compared to day 0 for each GFP+vs. GFP− outgrowth compared to fetal lung control tissue. *p≤0.05, ***p≤0.001 (Student's t-test; n=3 biological replicates). (FIG. 2D) Immunostainings of GFP+ outgrowth organoids on day 36 for MUC1, SFTPB, and TP63. Nuclei are counterstained with DAPI. Scale bar=10 μm.

(FIG. 3A) Schematic of micro-dissecting and combining iPSC-derived lung organoids with E12 mouse lung mesenchyme (LgM). (FIG. 3B) Light microscopy of the same recombinant on days 1, 3 and 5 of in vitro culture. White dashed lines indicate boundaries of mouse lung mesenchyme and human iPSC-derived organoid. (FIG. 3C) SFTPC mRNA expression (purple) assessed by in situ hybridization using an anti-human SFTPC probe to stain recombinants generated with either GFP+ vs. GFP− human iPSC-derived organoids recombined with distal mouse LgM. (FIG. 3D) Immunostaining of NKX2-1$^{GFP+}$/Distal LgM recombinants for NKX2-1, Ki67, LPCAT1, and pro-SFTPC proteins (with zoom). Brown=immunoperoxidase product after DAB exposure. (FIG. 3E) Representative phase microscopy of day 32 organoids grown from day 15 GFP+ sorted progenitors plated at limiting dilution. Shown beneath each image are the cell numbers plated per well of a 96-well plate on day 15. (FIG. 3F) Fold change of human SFTPC mRNA expression in day 32 organoids, generated from sorted Day 15 NKX2-1$^{GFP+}$ cells at concentrations ranging from 15,000 to 240 cells per well, compared to day 0 by RT-qPCR; $2^{(-\Delta\Delta CT)}$. Lines with error bars indicate mean±SD, n=8 biological replicates except for sample "240" where only 4 samples had appreciable RNA. (FIGS. 3D-3F with BU3 cells).

(FIG. 4A) Schematic overview of the lung directed differentiation timepoints and populations analyzed by microarrays. (FIG. 4B) Principal component analysis (PCA) of global transcriptomes of the biological triplicates from time points shown in FIG. 4A. (FIG. 4C) Unsupervised hierarchical clustering by dendrogram of the samples shown in FIG. 4A, based on the top ~1000 transcripts differentially expressed by ANOVA across all 27 samples. (FIG. 4D) Heatmap of the top 10 transcription factors differentially expressed between neural NKX2-1$^{GFP+}$ vs. Day 15 lung NKX2-1$^{GFP+}$ (15+) populations (ranked by fold change; filtered by FDR<0.01). (FIG. 4E) Heatmap of the top 10 genes differentially expressed between Day 15 lung NKX2-1$^{GFP+}$ (15+) vs. Day 15 lung NKX2-1$^{GFP-}$ (15-; ranked by FC; filtered by FDR<0.01). (FIG. 4F) Heatmap of the expression of known markers of neuroectoderm, endoderm, and lung epithelium (separated into progenitor stage and distal/alveolar vs. proximal/airway epithelium). Scale=row normalized $\log_2$ expression.

(FIG. 6A) Schematic of the single cell capture and global RNA sequencing of sorted C17 NKX2-1$^{GFP+}$ and unsorted BU3 iPSCs on day 15 of lung directed differentiation. (FIG. 6B) Principal components analysis (PCA) of the global transcriptomes of all sequenced cells reveals 4 cell clusters, color coded to match the clusters shown in panel FIG. 6C. (FIG. 6C) Heatmap of gene expression (Global Z-score) with unsupervised hierarchical clustering of all 153 cells (x-axis) and their differentially expressed genes (y-axis). Dendrograms as well as colored boxes indicate 4 cell clusters (CC1-4; matching colors shown in panel B.) Y-axis dendrograms and thick black lines indicate 3 gene clusters (GC1-GC3). Key genes indicated on right. CC1=orange, CC2=blue, CC3=red, CC4=green. (FIG. 6D) Top 10 genes correlated with NKX2-1 expression. (FIG. 6E) Unsupervised cell clustering using Monocle's "pseudotime" spanning tree analysis reveals 7 cell "states". Individual cells are labeled in subsequent panels by NKX2-1 level, genetic background (iPSC clone), or cell cycle (mitosis), respectively. (FIG. 6F) Pseudotime plots of expression levels of NKX2-1, CD47, SOX9, NFIB, FGB and APOA2 with cells colored based on the 7 "states" determined in FIG. 6E. (FIG. 6G) Immunostaining of RUES2-derived day 15 cells for NKX2-1 (red) and SOX9 (green) nuclear proteins. Nuclei counterstained with DAPI. Scale bar=25 μm.

FIG. 7A-FIG. 7G Cell surface profiling and Prospective isolation of iPSC-derived NKX2-1+ primordial lung progenitors by CD47$^{hi}$/C26$^{lo}$ cell sorting. (FIG. 7A) Day 15 iPSCs after lung directed differentiation, immunostained for CD47 and NKX2-1 proteins. Nuclear counterstaining with DAPI. Scale bar=100 μm. (FIG. 7B) Flow cytometry dot plots of 4 key cell surface markers identified in a screen of 243 surface markers on day 15 of lung directed differentiation; CD26 is depleted in NKX2-1$^{GFP+}$ cells, while CD47, ALCAM, MUC1, and CPM exhibit higher expression in the GFP+ population. (FIG. 7C) Schematic of experimental data for FIGS. 7D and 7E. Flow cytometry dot plots of live day 13 iPSCs after lung directed differentiation indicates staining with isotype control antibodies (left panel) or antibodies against CD47 and CD26. Sort gates identify "presorted" cells (grey box) vs a CD47$^{hi}$/CD26$^{lo}$ population (red box) or a CD47$^{lo}$ population (black box) profiled in FIGS. 7D and 7E. (FIG. 7D) Fold change of NKX2-1 mRNA (left graph) expression in day 13 presort, sorted GFP+, GFP− vs CD47$^{hi}$ populations and SFTPC mRNA (right graph) expression in CD47$^{hi}$/CD26$^{lo}$, CD47$^{lo}$, GFP+ and GFP− outgrowth on day 36 compared to day 0 iPSC by RT-qPCR; $2^{(-\Delta\Delta CT)}$. Data indicate mean±SD, *p≤0.05, p≤0.01, **p≤0.0001 (Student's t-test); n=4 biological replicates for NKX2-1, n=3 biological replicates for SFTPC. (FIG. 7E) GFP expression quantified in each of the gates shown in FIG. 7C: the day13 presort population is 62% NKX2-1$^{GFP+}$, while the CD47$^{hi}$/CD26$^{lo}$ population is 97% GFP+. CD47$^{lo}$ cells are 8% GFP+. Lower panel is FACS of day 36 outgrowth of each indicated day 13 sorted population: GFP+, CD47$^{hi}$/CD26$^{lo}$ vs. CD47$^{lo}$ (FIG. 7F) Phase contrast and fluorescence microscopy (GFP) of day 36 organoids derived from day 13 sorted GFP+, CD47$^{hi}$/CD26$^{lo}$ and CD47$^{lo}$ populations from FIG. 7E. (FIG. 7G) Confocal microscopy of outgrowth organoids, sorted on day 13 based on CD47$^{hi}$/CD26$^{lo}$ and analyzed on day 44 by co-immunostaining for NKX2-1 (green) and pro-SFTPC (purple). Scale bar=25 μm.

(FIG. 8A) Schematic of the targeting strategy used to introduce a 2A-GFP cassette at the end of exon 3 in order to preserve expression of each allele, in an effort to avoid haploinsufficiency. The donor vector includes a floxed PGK promoter-driven antibiotic selection cassette (puroTK, consisting of a fused Puro resistance-thymidine kinase [TK] cassette) which is excised following transient Cre recombinase exposure. FIAU exposure is used to kill any cells carrying the thymidine kinase (TK) cassette or to confirm successful PuroR-TK cassette excision. The TALENs cut site (in the case of C17 or WA09 PSCs, black bars=left and right TALENs) or CRISPR-Cas9 cut site (in the case of BU3 iPSCs, green bar=guide RNA), primer binding sites (black arrows), or southern blot probe binding sites (red box) are indicated, to be used in FIGS. 8B and 8C. Left and right arms of homology (L-HA and R-HA) as well as restriction endonuclease sites ApaLI and NheI are indicated. (FIG. 8B) NKX2-1 locus targeting screening by PCR of gDNA from iPSCs, using the primer pairs indicated in FIG. 8A. (FIG.

8C) Southern blot of gDNA extracted from each indicated iPSC clone after restriction enzyme digest with ApaLI or NheI and probing of the gel with the probe indicated as a red box in FIG. 8A. (FIG. 8D) Karyotyping of each indicated iPSC and ESC clone after gene editing and antibiotic selection cassette excision. Normal 46XY and 46XX karyotypes are shown. (FIG. 8E) Characterization by flow cytometry of pluripotency marker expression in each indicated clone before vs after gene editing. (FIG. 8F) NKX2-1 mRNA in Day 14 GFP+vs GFP− sorted cells using BU3NKX2-1$^{GFP}$. (FIG. 8G) Expression of NKX2-1 protein by intracellular FACS staining on day 15 of the lung differentiation in pre-targeted BU3 vs. homozygous targeted BU3NKX2-1$^{GFP}$. The percent positive for NKX2-1 protein as well as the mean fluorescence intensity (MFI) of the NKX2-1 staining is indicated for each clone. (FIG. 8H) Percentage H9C26NKX2-1$^{GFP+}$ cells on day 15 of lung directed differentiation.

FIG. 9A-FIG. 9E Stage-specific optimization of lung directed differentiation protocol and comparison to thyroid and forebrain directed differentiation protocols. (FIG. 9A) Schematic of endoderm induction and efficiency of endoderm induction at 60, 72 and 84 hours of differentiation based on co-expression of CKIT and CXCR4 measured by flow cytometry (BU3). (FIG. 9B) Schematic of experiment and representative flow cytometry plots of the effect of endoderm timing and density of replating on Day 15 NKX2-1$^{GFP+}$ induction. Heatmap of Day 15 NKX2-1$^{GFP+}$ percentage from 60, 72 or 84 hours endoderm induction at different cell plating densities (250,000, 75000 and 40000 cells per cm$^2$) (BU3). (FIG. 9C) RT-qPCR of day 6 and sorted NKX2-1$^{GFP+}$ cells on day 11 from the forebrain protocol compared to primary fetal brain, diencephalon and fetal lung controls. Data indicate individual biological replicates (n=3) with mean±SD. Fold changes (RT-qPCR; $2^{(-\Delta\Delta CT)}$) in mRNA expression are compared to day 0. (FIG. 9D) Immunostaining of day 17 cells from the thyroid directed differentiation protocol for NKX2-1 and PAX8 proteins (BU3). Cell nuclei are counterstained with DAPI. Scale bar=100 μm. (FIG. 9E) mRNA expression by RT-qPCR in day 18 C17 NKX2-1$^{GFP+}$ vs NKX2-1$^{GFP-}$ cells from thyroid protocol (two left panels) and in sorted NKX2-1$^{GFP+}$ cells from lung, thyroid and forebrain protocols (three right panels). Data indicate individual biological replicates (n=3) with mean±SD. Fold change [RT-qPCR; $2^{(-\Delta\Delta CT)}$] in mRNA expression are compared to day 0.

(FIG. 10A) Schematic of experiment. On day 15 of the lung differentiation the media is changed from CFKBRA to Chir+FGF10 (CF) until day 19. GFP+vs GFP− cells are sorted on day 19 for analysis. Fold change of TP63 and PITX1 mRNA expression in Day 15 and Day 19 GFP+vs GFP− compared to day 0 by RT-qPCR; $2^{(-\Delta\Delta CT)}$, n=3 replicates for day 19 (FIG. 10B) Immunostaining of TP63 (magenta), NKX2-1 (green) on day 19 demonstrates minimal colocalization. Nuclei labeled with DAPI. Scale bar=50 μm. (FIG. 10C) PAX8 mRNA expression by in situ hybridization in embryonic mouse thyroid, kidney and in recombinant of C17 NKX2-1$^{GFP+}$ microdissected organoid with E12.5 mouse distal lung mesenchyme (see also FIG. 3). (FIG. 10D) Fold change of human SFTPC mRNA expression compared to day 0 by RT-qPCR; $2^{(-\Delta\Delta CT)}$ indicates that distal rather than bronchial mouse LgM induces expression of SFTPC. (FIG. 10E) Adult human lung control for LPCAT1 immunostains (see also FIG. 3D).

(FIG. 11A) From the microarray data of the top 100 genes differently expressed in day 15 NKX2-1$^{GFP+}$ vs day 0, day 3, day 6 and day 15 NKX2-1$^{GFP-}$ cells, genes were ranked by fold change and filtered by FDR<0.01) in order to identify the top 10 differentially expressed genes in common across each comparison. Also listed are the top 10 genes differentially expressed in day 15 NKX2-1$^{GFP+}$ cells vs neural NKX2-1$^{GFP+}$ and day 15 NKX2-1$^{GFP+}$ cells vs day 28 NKX2-1$^{GFP+}$ cells. Top 10 genes differentially expressed by day 28 NKX2-1$^{GFP+}$ compared to day 15 NKX2-1$^{GFP+}$ cells (right panel). (FIG. 11B) Validation of mRNA expression levels of key genes identified by time series microarray tranccriptomic profiling. Fold change in expression levels for each indicated transcript is shown for Day 6, Day 15 GFP+ and Day 15 GFP− cells, compared to day 0 by RT-qPCR; $2^{(-\Delta\Delta CT)}$. Data indicate mean±SD, *p≤0.05, p≤0.01, **p≤0.0001 (Student's t-test); n=3 biological replicates. (FIGS. 11C & 11D) Graph of log 2 expression (y-axis) by microarrays of the indicated differentially expressed transcription factors on days 0, 3, 6, and 15+. Transcription factors with FC>4, FDR<0.01 and with known roles in foregut endoderm and developing lung development are included.

(FIG. 12A) Unbiased hierarchical clustering and significance testing was performed using SCICAST. Top significant differentially expressed genes from the three cell clusters: Mitotic (Yellow), APOA2+(Blue), and NKX2-1+(Green) were selected and hierarchical clustering re-run with the selected genes (left panel). Mitotic genes were removed and hierarchical clustering was re-run with the same cell group assignments as in revealing how the underlying identity of the mitotic cells falls among the two cell identities; APOA2 (Blue) or NKX2-1 (Green) (right panel). (FIG. 12B) Pseudotime plot of all cells by applying the unbiased Monocle clustering algorithm, used in FIG. 6. Units are arbitrary. (FIG. 12C) Heatmap of top genes that follow a similar kinetic in pseudotime. (FIG. 12D) 15 of the top 30 genes (by FDR-adjusted p value) that follow similar kinetics in pseudotime.

(FIG. 13A) Heatmap illustrating the expression of key lung genes including primordial markers (NKX2-1, SFTA3), early proximal vs distal markers (SOX2, SOX9), and more differentiated proximal vs distal markers (SCGB1A1, SFTPC) in the single-cell RNA-Seq analysis of Day 15 iPSC-derived cells. (FIG. 13B) Heatmap of 97 cells reanalyzed after removing the mitotic cell clusters (CC1 and 2) from FIG. 6C. Unsupervised hierarchical clustering reveals four cell subgroups (SG1-4). Key genes are indicated and highly statistically significant, differentially expressed genes that identify each SG are summarized below the x-axis. (FIG. 13C) Top 15 genes differentially expressed between NKX2-1+ subgroup SG2 vs NKX2-1− subgroup SG3, ranked by adjusted p-value. (FIG. 13D) Heatmap of expression of markers from a database of 24 human fetal lung samples ranging in gestation from 53 to 154 days (53). (FIG. 13E) Immunostain of human fetal lung (week 10) for CD47 (green) and NKX2-1 proteins (pink). Nuclei counterstained with DAPI, scale bar=25 μm.

(FIG. 14A)

Representative flow cytometry dot plot of EpCAM and NKX2-1$^{GFP}$ on day 15 of differentiation vs isotype control (C17). (FIG. 14B) Flow cytometry dot plots of isotype (mIgG1,k$^{PerCP/Cy5.5}$ and mIgG2a,k$^{PE}$), or single color (CD47$^{PerCP/Cy5.5}$ and CD26$^{PE}$) controls on day 15 of lung differentiation. (FIG. 14C) Representative flow cytometry dot plots of CD47$^{hi}$/CD26$^{lo}$ enrichment for NKX2-1$^{GFP}$ on day 15 of a high efficiency (top row, presort=56%) and low efficiency (lower row, presort=13%) lung differentiation in independent experiments. (FIG. 14D) Expression of intracellular NKX2-1 protein analyzed by FACS of RUES2 cells on day 15 of lung directed differentiation. Levels of NKX2-1 on day 15 are shown for presort, CD47$^{hi}$/CD26$^{lo}$ and CD47$^{lo}$ populations, compared to isotype antibody stained control day 15 cells. (FIG. 14E) Confocal microscopy of outgrowth organoids from progenitors sorted on CD47$^{hi}$/CD26$^{lo}$ on day 13 and analyzed on day 44 by immunostaining for NKX2-1 protein (green) and pro-SFTPC (purple). Cartoon depicts the two focal planes (panel A and B) of a single spherical organoid; compare to FIG. 7G. Nuclei are counterstained with DAPI. Scale bar=25 um. Each row is a different section through the same organoid.

DETAILED DESCRIPTION

Figure 1A:
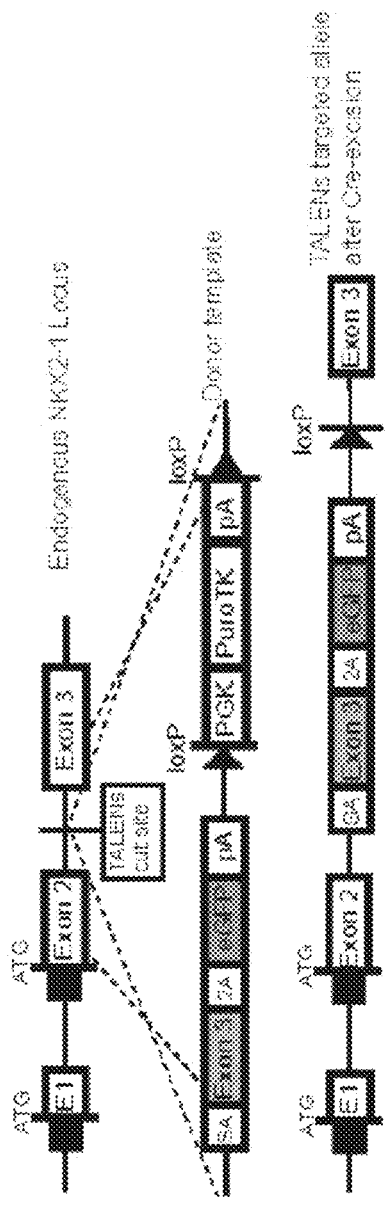
FIG. 1A-FIG. 1G Purification of human NKX2-1+ lineages derived from ESCs/iPSCs using NKX2-1$^{GFP}$ reporters.

The compositions and methods described herein are related, in part, to the discovery of a new cell surface phenotype that permits isolation of human lung progenitor cells during differentiation from e.g., embryonic stem (ES) cells or induced pluripotent stem cells (iPSCs). The methods and compositions described herein have the advantage of being able to produce a large quantity of cells for e.g., tissue engineering, cell therapy, or pharmaceutical compositions thereof. In addition, methods relating to the production of autologous lung progenitor cells are described herein.

Another major benefit of the methods described herein relates to the ability to standardize an approach to differentiate iPSCs to a variety of different lung cells. Thus, the methods described herein can easily be translated to a clinical setting and can be used to generate cell-based therapies. This standardized approach is based, in part, on the isolation of a distinct group of lung progenitor cells comprising a cell surface phenotype comprising CD47$^{hi}$/CD26$^{lo}$. This cell surface phenotype can be used to isolate primordial lung progenitors derived from a variety of cell lines, cultured cells, reprogrammed/redifferentiated cells, and even from tissue, thereby making it applicable to a variety of uses including cell-based therapies or in vitro assays. The working Examples provided herein show that the cell surface marker phenotype described herein provides consistent and efficient isolation of primordial lung cells from a population of cells, which permits standardization of in vitro lung progenitor generation (or generation of their differentiated progeny). Thus, the methods can be easily reproduced in either a research or clinical setting by one of skill in the art.

Further, one of skill in the art will appreciate that a standardized approach is particularly useful in the field of personalized medicine, where a cell therapy can be generated from the subject's own somatic cells. Personalized medicine requires simple, consistent and reproducible methods of generating cells, as provided herein, in order to be feasible for use in a clinical setting. In addition, it is envisioned that such personalized cells and their progeny can be used to perform a personalized assessment of drug responsiveness to a given disease. Other applications of the cells and their progeny include general drug development and drug screening.

Definitions

As used herein, the term "human lung progenitor cell" refers to a progenitor cell that is committed to the pulmonary lineage and also retains the ability to self-renew. In one embodiment, the human lung progenitor cell expresses the cell surface phenotype CD47$^{hi}$/CD26$^{lo}$. In other embodiments, the lung progenitor cell also expresses NKX2-1. The human lung progenitor cells described herein have the capacity to differentiate into a variety of different lung cells, including but not limited to, alveolar epithelial cells, basal cells, secretory cells, ciliated cells and pulmonary neuroendocrine cells. Thus, the human lung progenitor cells described herein can be considered to be "primordial cells." A human lung progenitor cell is not a tumor cell or a cancer cell. In one aspect, a human lung progenitor cell is not derived from an embryo or from an embryonic stem cell or other cell derived in culture from an embryo. In some embodiments, the human lung progenitor cells are differentiated from autologous cells or from non-autologous cells. In one embodiment, the human lung progenitor is genetically modified or is derived from a genetically modified cell. However, in another embodiment, the human lung progenitor cell is not genetically modified or derived from a genetically modified cell.

As used herein, the term "positive for" when referring to a cell positive for a marker (e.g., Nkx2.1 positive) means that a cell surface marker is detectable above background levels on the cell using immunofluorescence microscopy or flow cytometry methods, such as fluorescence activated cell sorting (FACS). Alternatively, the terms "positive for" or "expresses a marker" means that expression of mRNA encoding a cell surface or intracellular marker is detectable above background levels using RT-PCR. The expression level of a cell surface marker or intracellular marker can be compared to the expression level obtained from a negative control (i.e., cells known to lack the marker) or by isotype controls (i.e., a control antibody that has no relevant specificity and only binds non-specifically to cell proteins, lipids or carbohydrates). Thus, a cell that "expresses" a marker (or is "positive for a marker") has an expression level detectable above the expression level determined for the negative control for that marker.

As used herein, the term "negative for" when referring to a cell negative for a marker (or the term "does not express") means that a cell surface marker cannot be detected above background levels on the cell using immunofluorescence microscopy or flow cytometry methods, such as fluorescence activated cell sorting (FACS). Alternatively, the terms "negative" or "does not express" means that expression of the mRNA for an intracellular marker or cell surface marker (e.g., protein, glycoprotein, or polypeptide, among others) cannot be detected above background levels using RT-PCR. The expression level of a cell surface marker or intracellular marker can be compared to the expression level obtained from a negative control (i.e., cells known to lack the marker) or by isotype controls (i.e., a control antibody that has no relevant specificity and only binds non-specifically to cell proteins, lipids or carbohydrates). Thus, a cell that "does not express" a marker appears similar to the negative control for that marker.

As used herein, the term "high expression," "high expression level," or "hi" when referring to a positive marker (e.g., a cell surface marker), refers to a level of expression of the cell surface marker on a human lung progenitor that is at least 10% higher than the expression of the cell surface marker on a control cell. In other embodiments, the level of expression of the marker on the human lung progenitor is at least 20%, at least 30%, at least 40%, at least 50%, at least 60%, at least 70%, at least 75%, at least 80%, at least 85%, at least 90%, at least 100% (i.e., 1-fold), at least 2-fold, at least 5-fold, at least 10-fold, at least 100-fold, at least 1000-fold or higher than the level of expression of the same marker on a control cell. Essentially any cell that is not a human lung progenitor cell, as that term is used herein, can be used as a control cell. In one embodiment, the control cell is a cell that is not committed to the lung lineage (e.g., a thyroid progenitor cell or a neuronal progenitor cell). In another embodiment, the control cell is a reference value or number related to the level of expression of the marker and obtained from a population of cells that are not human lung progenitor cells. In one embodiment, the term "CD47$^{hi}$" refers to a level of expression of CD47 on the surface of a lung progenitor cell that is at least 1 standard deviation, at least 2 standard deviations, at least 5 standard deviations, at least 10 standard deviations or more above the level of expression of CD47 on the surface of a normal cell (i.e., a stem cell not committed to the lung lineage or a differentiated lung cell).

As used herein, the term "low expression," "low expression level," or "lo" when referring to a positive marker (e.g., a cell surface marker), refers to a level of expression of the cell surface marker on a human lung progenitor that is at least 10% lower than the expression of the cell surface marker on a control cell. In other embodiments, the level of expression of the marker on the human lung progenitor is at least 20%, at least 30%, at least 40%, at least 50%, at least 60%, at least 70%, at least 75%, at least 80%, at least 85%, at least 90%, at least 95%, at least 99%, or at least 100% (i.e., below detectable levels) than the level of expression of the same marker on a control cell. In one embodiment, the term "CD26$^{lo}$" refers to a level of expression of CD26 on the surface of a lung progenitor cell that is at least 1 standard deviation, at least 2 standard deviations, at least 5 standard deviations, at least 10 standard deviations or more below the level of expression of CD26 on the surface of a normal cell (i.e., a stem cell not committed to the lung lineage or a differentiated lung cell).

As used herein, the phrase "proliferative" when used in reference to human lung progenitor cells, refers to the ability of a progenitor cell to self-renew and/or expand in culture.

As used herein, the term "capacity to differentiate" refers to the ability of a human lung progenitor cell (or other stem cell, multipotent cell or pluripotent cell) to differentiate into a subset of more differentiated cells. The term "capacity to differentiate" does not encompass moving backwards along the differentiation spectrum such that a cell is produced that comprises a greater differentiation capacity than the parent cell. That is, the term "capacity to differentiate" does not encompass reprogramming methods to shift cells to a less differentiated state.

In the context of cell ontogeny, the term "differentiate", or "differentiating" is a relative term that indicates a "differentiated cell" is a cell that has progressed further down the developmental pathway than its precursor cell. Thus in some embodiments, a reprogrammed cell as this term is defined herein, can differentiate to lineage-restricted precursor cells (such as a human lung progenitor cell), which in turn can differentiate into other types of precursor cells further down the pathway (such as a tissue specific precursor, for example, a proximal airway multipotent progenitor cell), and then to an end-stage differentiated cell (e.g. basal cells, ciliated cells, pulmonary neuroendocrine cells etc.), which plays a characteristic role in a certain tissue type, and may or may not retain the capacity to proliferate further.

As used herein, the terms "dedifferentiation" or "reprogramming" or "retrodifferentiation" refer to the process that generates a cell that re-expresses a more stem cell phenotype or a less differentiated phenotype than the cell from which it is derived. For example, a terminally differentiated cell can be dedifferentiated to a pluripotent cell or a stem cell (e.g., induced pluripotent stem cells). That is, dedifferentiation shifts a cell backward along the differentiation spectrum of totipotent cells to fully differentiated cells. Typically, reversal of the differentiation phenotype of a cell requires artificial manipulation of the cell, for example, by expressing stem cell-specific mRNA and/or proteins. Reprogramming is not typically observed under native conditions in vivo or in vitro.

As used herein, the term "somatic cell" refers to any cell other than a germ cell, a cell present in or obtained from a pre-implantation embryo, or a cell resulting from proliferation of such a cell in vitro. Stated another way, a somatic cell refers to any cells forming the body of an organism, as opposed to germline cells. Every cell type in the mammalian body—apart from the sperm and ova, the cells from which they are made (gametocytes) and undifferentiated stem cells—is a somatic cell: internal organs, skin, bones, blood, and connective tissue are all substantially made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. Unless otherwise indicated the methods for reprogramming a differentiated cell (e.g., to generate an iPSC) can be performed both in vivo and in vitro (where in vivo is practiced when a differentiated cell is present within a subject, and where in vitro is practiced using an isolated differentiated cell maintained in culture).

As used herein, the term "adult cell" refers to a cell found throughout the body after embryonic development.

The term "isolated cell" as used herein refers to a cell that has been removed from an organism or population of cells in which it was originally found, or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched. In some embodiments, the isolated population is an isolated population of human lung progenitor cells, e.g., a population of human lung progenitor cells that are at least 80%, at least 85%, at least 90%, at least 92%, at least 95%, at least 98%, at least 99%, or even 99.9% or higher (e.g., a substantially pure population) as compared to a heterogeneous population of cells comprising human lung progenitor cells and cells from which the human lung progenitor cells were derived.

The term "substantially pure," with respect to a particular cell population, with regard to a population of lung progenitor cells, refers to a population of cells that contain fewer than about 20%, 15%, 10%, 8%, 7%, preferably fewer than about 5%, 4%, 3%, 2%, 1%, or less than 1%, of cells that are not lung progenitor cells as defined by the terms herein.

The terms "enriching" or "enriched" are used interchangeably herein and mean that the yield (fraction) of cells of one type, such as human lung progenitor cell compositions and cells for use in the methods described herein, is increased by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, or by at least 75%, over the fraction of cells of that type in the starting biological sample, culture, or preparation.

As used herein, "proliferating" and "proliferation" refer to an increase in the number of cells in a population (growth) by means of cell division. Cell proliferation is generally understood to result from the coordinated activation of multiple signal transduction pathways in response to the environment, including growth factors and other mitogens. Cell proliferation can also be promoted by release from the actions of intra- or extracellular signals and mechanisms that block or negatively affect cell proliferation.

The terms "renewal" or "self-renewal" or "proliferation" are used interchangeably herein, and refers to a process of a cell making more copies of itself (e.g. duplication) of the cell. In some embodiments, lung progenitor cells are capable of renewal of themselves by dividing into the same undifferentiated cells (e.g., as determined by measuring the presence of absence of one or more cell surface markers) over long periods, and/or many months to years. In some instances, proliferation refers to the expansion of lung progenitor cells by the repeated division of single cells into two identical daughter cells.

The term "sorting," "separation" or "selection" as used herein refers to isolating different cell types into one or more populations and collecting the isolated population as a target cell population which is enriched in a specific target stem cell population. Selection can be performed using positive selection, whereby a target enriched cell population is retained, or negative selection, whereby non-target cell types are discarded (thereby enriching for desired target cell types in the remaining cell population).

The term "positive selection" as used herein refers to selection of a human lung progenitor cell by retaining the cells of interest. In some embodiments, positive selection involves the use of an agent to assist in retaining the cells of interest, e.g., use of a positive selection agent such as an antibody which has specific binding affinity for a surface antigen on the desired or target cell. For example, the human lung progenitor cells described herein can be separated from the closely related neuronal cell precursors by measuring increased expression of one or more transcriptional markers selected from the group consisting of: GRHL2, ELF3, GATA6, HNF1B, HOXA1 and FOXA1. In some embodiments, the lung progenitor cells further express SFTA3, CPM, NFIB, NKX2-1, CRH, JUN, MECOM, SOX2, HES1, HOXA1, FOXA2, FOXA1, GATA6, GRHL2, IRX1, IRX2, ELF3, ELF5, HNFIB, FOXP2, HOXA4, HOXC4, SHH, EPCAM, CD166, CD227, SOX2, SOX9, and/or LAMA2. In some embodiments, positive selection can occur in the absence of a positive selection agent, e.g., in a "touch-free" or closed system, for example, where positive selection of a target cell type is based on any of cell size, density and/or morphology of the target cell type.

The term "negative selection" as used herein refers to selection of undesired or non-target stem cells for depletion or discarding, thereby retaining (and thus enriching) the desired target cell type. In some embodiments, negative selection involves the use of an agent to assist in selecting undesirable cells for discarding, e.g., use of a negative selection agent such as a monoclonal antibody which has specific binding affinity for a surface antigen on unwanted or non-target cells. In some embodiments, negative selection does not involve a negative selection agent. In some embodiments, negative selection can occur in the absence of a negative selection agent, e.g., in a "touch-free" or closed system, for example, where negative selection of an undesired (non-target) cell type to be discarded is based on any of cell size, density and/or morphology of the undesired (non-target) cell type. In some embodiments, the lung progenitors described herein do not express mature lung markers, thus the human lung progenitor cells can be isolated from partially differentiated cells, for example, by detecting and discarding those cells that comprise a marker selected from the group consisting of: lowSCG1A1, SCGB3A2, TP63, SFTPB, and/or SFTPC. In another embodiment, the lung progenitor cells described herein do not express SCGB3A2, SFTPB, TP63, ICAM1, IL8, ASCL1, FOXJ1, SCGB1A1, ITGB6, SIX3, SIX6, OTX1 or PAX8.

The term "marker" as used herein is used to describe the characteristics and/or phenotype of a given cell. Markers can be used for selection of cells comprising characteristics of interest and can vary with specific cells. Markers can be cell characteristics, whether morphological, functional or biochemical (enzymatic) characteristics of the cell of a particular cell type, or molecules expressed by the cell type. In one aspect, such markers are proteins. Such proteins can possess an epitope for antibodies or other binding molecules available in the art. However, a marker can consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers can be detected by any method available to one of skill in the art. Markers can also be the absence of a morphological characteristic or absence of proteins, lipids etc. Markers can be a combination of a panel of unique characteristics of the presence and/or absence of polypeptides and other morphological characteristics. In one embodiment, the marker is a cell surface marker. Exemplary cell surface markers expressed on lung progenitor cells include, but are not limited to, $CD47^{hi}/CD26^{lo}$, SFTA3, CPM, NFIB, NKX2-1, CRH, JUN, MECOM, SOX2, HES1, HOXA1, FOXA2, FOXA1, GATA6, GRHL2, IRX1, IRX2, ELF3, ELF5, HNFIB, FOXP2, HOXA4, HOXC4, SHH, EPCAM, CD166, CD227, SOX2, SOX9, and/or LAMA2. In some embodiments, the absence of a cell surface marker can be used to distinguish a lung progenitor cell from a cell of another lineage (e.g., a thyroid or brain lineage). Exemplary cell surface markers that are absent on lung progenitor cells or differentiated lung cells include, but are not limited to, SCGB3A2, SFTPB, TP63, ICAM1, IL8, ASCL1, FOXJ1, SCGB1A1, ITGB6, SIX3, SIX6, OTX1 or PAX8. One of skill in the art will recognize that a cell surface marker can be present at a particular point in development or in a particular lung progenitor cell type. For example, Sox2 is expressed in progenitor cells of the anterior endoderm, is not expressed in more differentiated lung progenitors, such as distal multipotent lung progenitors, and then is reactivated in cells such as airway progenitors as differentiation of the progenitors progresses. Thus, a cell surface marker can be used in combination with a positive selection strategy for certain lung progenitors and also used as in combination with a negative selection strategy for other lung progenitors, depending on the particular differentiation stage of the desired lung progenitor to be selected.

As used herein, the term "scaffold" refers to a structure, comprising a biocompatible material that provides a surface suitable for adherence and proliferation of cells. A scaffold can further provide mechanical stability and support. A scaffold can be in a particular shape or form so as to influence or delimit a three-dimensional shape or form assumed by a population of proliferating cells. Such shapes or forms include, but are not limited to, films (e.g., a form with two-dimensions substantially greater than the third dimension), ribbons, cords, sheets, flat discs, cylinders, spheres, 3-dimensional amorphous shapes, etc. In one embodiment, the scaffold is implantable in a subject. In one embodiment, the scaffold is biodegradable.

As used herein, the term "implantable in a subject" refers to any non-living (e.g., acellular) implantable structure that upon implantation does not generate an appreciable immune response in the host organism. Thus, an implantable structure should not for example, be or contain an irritant, or contain LPS etc.

As used herein, the term "biodegradable" refers to the ability of a scaffold to degrade under physiological conditions, for example under conditions that do not adversely affect cell viability of the delivered cells or cells in vivo. Such biodegradable scaffolds will preferably not be or contain an irritant or an allergen that can cause a systemic reaction in the subject to which the composition has been implanted. In some embodiments, biodegradable means that the scaffold can be metabolized and the metabolites cleared from the subject by physiological excretion mechanisms (e.g., urine, feces, liver detoxification etc.).

As used herein, the term "treating" includes reducing or alleviating at least one adverse effect or symptom of a condition, disease or disorder. For example, the term "treating" and "treatment" refers to administering to a subject an effective amount of a composition, e.g., an effective amount of a composition comprising a population of human lung progenitor cells so that the subject has a reduction in at least one symptom of a given lung disease or an improvement in the disease, for example, beneficial or desired clinical results. For purposes of this disclosure, beneficial or desired clinical results include, but are not limited to, alleviation of one or more symptoms (e.g., shortness of breath), diminishment of extent of disease, disease stabilization (e.g., not worsening), delay or slowing of disease progression, amelioration or palliation of the disease state, and remission (whether partial or total), whether detectable or undetectable. In some embodiments, treating can refer to prolonging survival as compared to expected survival if not receiving treatment. Thus, one of skill in the art realizes that a treatment can improve the disease condition, but may not be a complete cure for the disease. In some embodiments, treatment can include prophylaxis. However, in alternative embodiments, treatment does not include prophylaxis.

"Treatment" of a lung disorder, a lung disease, or a lung injury (e.g., acute lung injury) as referred to herein refers to therapeutic intervention that stabilizes or improves the function of the lung or the airway. That is, "treatment" is oriented to the function of the respiratory tract. A therapeutic approach that stabilizes or improves the function of the lung or the airway by at least 10%, and preferably by at least 20%, 30%, 40%, 50%, 75%, 90%, 100% or more, e.g., 2-fold, 5-fold, 10-fold or more, up to and including full function, relative to such function prior to such therapy is considered effective treatment. Effective treatment need not cure or directly impact the underlying cause of the lung disease or disorder to be considered effective treatment.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used with the methods described herein that will be effective in the treatment of a particular disorder or condition will depend on the nature of the disorder or condition, and can be determined by standard clinical techniques.

As used herein, "prevention" or "preventing," when used in reference to a disease, disorder or symptoms thereof, refers to a reduction in the likelihood that an individual will develop a disease or disorder, e.g., a lung disorder, such as interstitial lung disease. The likelihood of developing a disease or disorder is reduced, for example, when an individual having one or more risk factors for a disease or disorder either fails to develop the disorder or develops such disease or disorder at a later time or with less severity, statistically speaking, relative to a population having the same risk factors and not receiving treatment as described herein. The failure to develop symptoms of a disease, or the development of reduced (e.g., by at least 10% on a clinically accepted scale for that disease or disorder) or delayed (e.g., by days, weeks, months or years) symptoms is considered effective prevention.

As used herein, the term "induced to differentiate" refers to a chemical/biological treatment, a physical environment or a genetic modification that is conducive to the formation of more differentiated cells (e.g., human lung progenitor cells) from pluripotent or multipotent stem cells (e.g., anterior foregut endoderm cells). Differentiation can be assessed by the appearance of distinct cell-type specific markers or by the loss of stem cell specific markers, or both.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Sources of Pluripotent Cells

Stem cells are cells that retain the ability to renew themselves through mitotic cell division and can differentiate into a diverse range of specialized cell types. Three broad types of mammalian stem cells include: embryonic stem (ES) cells that are found in blastocysts, induced pluripotent stem cells (iPSCs) that are reprogrammed from somatic cells, and adult stem cells that are found in adult tissues. Pluripotent stem cells can also be derived from amniotic tissue/fluid and/or placental tissue. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin or intestinal tissues. Pluripotent stem cells can differentiate into cells derived from any of the three germ layers.

Provided herein are methods of generating human lung progenitor cells from both embryonic stem cells and induced pluripotent stem cells. In one embodiment, the methods provided herein relate to generation of human lung progenitor cells from embryonic stem cells. Alternatively, in some embodiments, the methods provided herein do not encompass generation of human lung progenitor cells from embryonic stem cells or any other cells of human embryonic origin.

Embryonic stem cells: Embryonic stem cells and methods of their retrieval are well known in the art and are described, for example, in Trounson A O (Reprod Fertil Dev (2001) 13: 523), Roach M L (Methods Mol Biol (2002) 185: 1), and Smith A G (Annu Rev Cell Dev Biol (2001) 17:435). The term "embryonic stem cell" is used to refer to the pluripotent stem cells of the inner cell mass of the embryonic blastocyst (see e.g., U.S. Pat. Nos. 5,843,780, 6,200,806). Such cells can similarly be obtained from the inner cell mass of blastocysts derived from somatic cell nuclear transfer (see, for example, U.S. Pat. Nos. 5,945,577, 5,994,619, 6,235, 970). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like. Undifferentiated embryonic stem (ES) cells are easily recognized by those skilled in the art, and typically appear in the two dimensions of a microscopic view in colonies of cells with high nuclear/cytoplasmic ratios and prominent nucleoli.

Cells derived from embryonic sources can include embryonic stem cells or stem cell lines obtained from a stem cell bank or other recognized depository institution. Embryonic stem cells are considered to be undifferentiated when they have not committed to a specific differentiation lineage. In some embodiments, the human lung progenitor cells described herein are not derived from embryonic stem cells or any other cells of embryonic origin.

Adult Stem Cells:

Adult stem cells are stem cells, which are derived from tissues of a post-natal or post-neonatal organism or from an adult organism are also known in the art. An adult stem cell is structurally distinct from an embryonic stem cell not only in markers it does or does not express relative to an embryonic stem cell, but also by the presence of epigenetic differences, e.g. differences in DNA methylation patterns.

Induced Pluripotent Stem Cells (IPSCs):

In some embodiments, the human lung progenitor cells described herein are derived from isolated pluripotent stem cells. An advantage of using iPSCs is that the cells can be derived from the same subject to which the human lung progenitor cells are to be administered. That is, a somatic cell can be obtained from a subject, reprogrammed to an induced pluripotent stem cell, and then re-differentiated into a human lung progenitor cell to be administered to the subject (e.g., autologous cells). Since the lung progenitors are essentially derived from an autologous source, the risk of engraftment rejection or allergic responses is reduced compared to the use of cells from another subject or group of subjects. In some embodiments, the lung progenitors are derived from non-autologous sources. In addition, the use of iPSCs negates the need for cells obtained from an embryonic source. Thus, in one embodiment, the stem cells used in the disclosed methods are not embryonic stem cells.

Although differentiation is generally irreversible under physiological contexts, several methods have been recently developed to reprogram somatic cells to induced pluripotent stem cells. Exemplary methods are known to those of skill in the art and are described briefly herein below.

As used herein, the term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. In some embodiments, reprogramming encompasses complete reversion of the differentiation state of a differentiated cell (e.g., a somatic cell) to a pluripotent state or a multipotent state. In some embodiments, reprogramming encompasses complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain embodiments described herein, reprogramming of a differentiated cell (e.g., a somatic cell) causes the differentiated cell to assume an undifferentiated state (e.g., is an undifferentiated cell). The resulting cells are referred to as "reprogrammed cells," or "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent, although the compositions and methods described herein can also be of use for such purposes, in some embodiments.

The specific approach or method used to generate pluripotent stem cells from somatic cells (broadly referred to as "reprogramming") is not critical to the claimed invention. Thus, any method that re-programs a somatic cell to the pluripotent phenotype would be appropriate for use in the methods described herein.

iPS cells can be generated or derived from practically any terminally differentiated somatic cell, as well as from an adult stem cell, or a somatic stem cell. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 2010 Nov. 5; 7(5):618-30). Reprogramming can be achieved by introducing a combination of nucleic acids encoding stem cell-associated genes including, for example Oct-4 (also known as Oct-3/4 or Pouf51), Sox1, Sox2, Sox3, Sox 15, Sox 18, NANOG, Klf1, Klf2, Klf4, Klf5, NR5A2, c-Myc, 1-Myc, n-Myc, Rem2, Tert, and L1N28. As noted above, the exact method used for reprogramming is not necessarily critical to the methods and compositions described herein. However, where cells differentiated from the reprogrammed cells are to be used in, e.g., human therapy, in one embodiment the reprogramming is not effected by a method that alters the genome. Thus, in such embodiments, reprogramming is achieved, e.g., without the use of viral or plasmid vectors.

In one embodiment, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCDO103, NVP-LAQ-824, CBHA (m-carboxycinnaminic acid bishydroxamic acid), JNJ16241199, Tubacin, A-161906, proxamide, oxamflatin, 3-Cl-UCHA (e.g., 6-(3-chlorophenylureido)caproic hydroxamic acid), AOE (2-amino-8-oxo-9,10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Aton Pharma, Titan Pharmaceuticals, Schering AG, Pharmion, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbxl5, Ecat1, Esg1, Eras, Gdf3, Fgf4, Cripto, Dax1, Zpf296, Slc2a3, Rex1, Utf1, and Nat1. In one embodiment, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. In some embodiments, detection does not involve only RT-PCR, but also includes detection of protein markers. Intracellular markers may be best identified via RT-PCR, while cell surface markers are readily identified, e.g., by immunocytochemistry.

The pluripotent stem cell character of isolated cells can be confirmed by tests evaluating the ability of the iPSCs to differentiate to cells of each of the three germ layers. As one example, teratoma formation in nude mice can be used to evaluate the pluripotent character of the isolated clones. The cells are introduced to nude mice and histology and/or immunohistochemistry is performed on a tumor arising from the cells. The growth of a tumor comprising cells from all three germ layers, for example, further indicates that the cells are pluripotent stem cells.

Somatic cell types useful for reprogramming include, but are not limited to, a fibroblast (e.g., a primary fibroblast), a muscle cell (e.g., a myocyte), a cumulus cell, a neural cell, a mammary cell, a hepatocyte and a pancreatic islet cell. In some embodiments, the somatic cell is a primary cell line or is the progeny of a primary or secondary cell line. In some embodiments, the somatic cell is obtained from a human sample, e.g., a hair follicle, a blood sample, a biopsy (e.g., a skin biopsy or an adipose biopsy), a swab sample (e.g., an oral swab sample), and is thus a human somatic cell.

Some non-limiting examples of differentiated somatic cells include, but are not limited to, epithelial, endothelial, neuronal, adipose, cardiac, skeletal muscle, immune cells, hepatic, splenic, lung, circulating blood cells, gastrointestinal, renal, bone marrow, and pancreatic cells. In some embodiments, a somatic cell can be a primary cell isolated from any somatic tissue including, but not limited to brain, liver, lung, gut, stomach, intestine, fat, muscle, uterus, skin, spleen, endocrine organ, bone, etc. Further, the somatic cell can be from any mammalian species, with non-limiting examples including a murine, bovine, simian, porcine, equine, ovine, or human cell. In some embodiments, the somatic cell is a human somatic cell.

When reprogrammed cells are used for generation of human lung progenitor cells to be used in the therapeutic treatment of disease, it is desirable, but not required, to use somatic cells isolated from the patient being treated. For example, somatic cells involved in diseases, and somatic cells participating in therapeutic treatment of diseases and the like can be used. In some embodiments, a method for selecting the reprogrammed cells from a heterogeneous population comprising reprogrammed cells and somatic cells they were derived or generated from can be performed by any known means. For example, a drug resistance gene or the like, such as a selectable marker gene can be used to isolate the reprogrammed cells using the selectable marker as an index.

Reprogrammed somatic cells as disclosed herein can express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; βIII-tubulin; α-smooth muscle actin (α-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthl17; Sall4; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4; other general markers for pluripotency, etc. Other markers can include Dnmt3L; Sox15; Stat3; Grb2; β-catenin, and Bmi1. Such cells can also be characterized by the down-regulation of markers characteristic of the somatic cell from which the induced pluripotent stem cell is derived.

In some embodiments, it may be desirable to correct a genetic defect or repair genomic DNA (i.e., modify the cell) related to a given disease in a reprogrammed cell prior to preparing and administering autologous human lung progenitor cells to the subject. Thus, in some embodiments, a genomic modification is introduced to the cell. Genomic modifications can include a point mutation, a deletion, an insertion, or a frame-shift mutation. In another embodiment, the cell is modified by transduction of a non-integrating vector (e.g., non-retroviral vector). Expression of a desired gene product(s) from the non-integrating vector would be present only in the parent cells or early daughter cells, after which the non-integrating vector would be "diluted" out of the cell population. Thus, this approach can permit expression of a desired gene product(s) at a particular time in development. While any method for modifying the genome of a cell can be used with the methods and compositions described herein, the use of CRISPR/Cas9 methods is preferred due to the ability to precisely define where the genomic modification is placed in the endogenous genome. Alternatively, genetic modifications can be randomly inserted into the genome; care should be taken to evaluate cells resulting from random integration of genetic modifications for their ability to cause tumors before administration to a subject for therapy.

Generation of Definitive Endoderm and Anterior Foregut Endoderm

The methods for generating human lung progenitor cells as described herein begin by first generating definitive endoderm from embryonic stem cells or induced pluripotent stem cells. "Definitive endoderm" comprises a multipotent cell committed to the endoderm lineage and that can give rise to cells of the gut tube or organs derived from the gut tube. The term "definitive endoderm" does not encompass the separate lineage of cells termed primitive endoderm, which is responsible for formation of extra-embryonic tissues.

Formation of definitive endoderm and endoderm cells derived therefrom is an important step for the derivation of cells which make up terminally differentiated tissues and/or organs derived from the definitive endoderm lineage, such as the human lung progenitor cells as described herein.

Methods for deriving definitive endoderm from embryonic stem cells or induced pluripotent stem cells are known in the art (e.g., U.S. Pat. Nos. 7,993,916; 7,695,963; 7,541,185; US2009/0298178; US2010/0272695; Sherwood et al., *Mechanisms of Development* (2011) 128:387-400; D'Amour K. et al., *Nature Biotechnology* (2005) 23:1534-1541; Turovets, N. et al., *Differentiation* (2011) 81(5):292-298; Kim, P T. et al., *PLoS One* (2010) 5(11):e14146).

Differentiation of embryonic stem cells or induced pluripotent stem cells to definitive endoderm can be monitored by determining the expression of cell surface markers characteristic of definitive endoderm. In some embodiments, the expression of definitive endoderm markers is determined by detecting the presence or absence of the marker. Alternatively, the expression of certain markers can be determined by measuring the level at which the marker is present in the cells of the cell culture or cell population. Such measurements of marker expression can be either qualitative or quantitative.

In one embodiment, quantitative PCR (Q-PCR) is used to quantify the expression of markers on the definitive endoderm. Methods of performing Q-PCR are well known in the art. In alternative embodiments, expression of a marker gene product is detected using antibodies specific for the cell marker. In certain embodiments, the expression of marker genes characteristic of definitive endoderm as well as the lack of significant expression of marker genes characteristic of the cells from which they are derived (e.g., ES cells or iPSCs) and other cell types is determined.

In one embodiment, a marker of definitive endoderm is the SOX17 gene. Other markers of definitive endoderm include, but are not limited to, MIXL1, GATA4, HNF3b, GSC, FGF17, VWF, CALCR, FOXQ1, CMKOR1 and CRIP1. In some embodiments, the expression of both SOX17 and SOX7 is monitored. In other embodiments, expression of the SOX17 marker gene and the OCT4 marker gene, which is characteristic of ES cells, is monitored. Additionally, because definitive endoderm cells express the SOX17 marker gene at a level higher than that of the AFP, SPARC or Thrombomodulin marker genes, the expression of these genes can also be monitored. Another marker of definitive endoderm is the CXCR4 gene, which encodes a cell surface chemokine receptor whose ligand is the chemoattractant SDF-1. In one embodiment, the efficiency of definitive endoderm production can be determined by costaining for FOXA2/SOX17 or by FACS analysis with cKit/CXCR4 or cKit/EpCAM combination.

Once generation of definitive endoderm has been achieved, the next step is to differentiate the definitive endoderm cells to anterior foregut endoderm-like cells, which is the region that comprises the cells destined to become lung and thyroid cells. This process is also referred to herein as "anteriorization" of definitive endoderm. As used herein, "foregut endoderm" refers to cells of the anterior portion of the gut tube and encompasses cells of the foregut/midgut junction. It will be recognized by one of skill in the art that ESCs or iPSCs can also be differentiated directly to anterior foregut endoderm cells without requiring an intermediate step of generating definitive endoderm. The differentiation methods described herein for generating lung progenitor cells are not limited to a particular method of making anterior foregut endoderm cells. That is, any method that provides anterior foregut endoderm can be used to provide the starting material for preparation of lung progenitor cells, as disclosed herein.

Methods for generating anterior foregut endoderm from definitive endoderm are known in the art (see e.g., WO2010/136583, WO2011/139628; Green, M D et al., *Nature Biotechnology* (2011) 29:267-27; Morrison et al, (2008), *Cell Stem Cell*, 3: 355-356; Goss A M et al., *Developmental Cell* (2009) 17(2):290-298; Livigni A et al., *Current Protocols in Stem Cell Biology* (2009) 10:1G.3.1-1G.3.10).

In one embodiment, the production of anterior foregut endoderm is confirmed by the activation of an anterior foregut endoderm specific marker, such as the marker Hex. Hex is a homeobox-containing transcriptional repressor that is one of the earliest markers of anterior foregut endoderm, and has been shown to suppress posterior characteristics (see e.g., Brickman J M et al., *Development* (2000) 127:2303-2315; Thomas P Q et al., *Development* (1998) 125:85-94; Zamparini A L et al., *Development* (2006) 133:3709-3722). The detection of Hex can be used in combination with other anterior foregut endoderm markers, such as Cxcr4 (Morrison, G M et al., *Cell Stem Cell* (2008) 3:402-412). Other exemplary markers include, but are not limited to, FoxA2 and Sox2, among others. In one embodiment, the definitive endoderm undergoes an anteriorization step comprising treatment with a TGFβ agonist (e.g., Activin).

Signaling Pathways for Differentiation

Essentially any method for differentiating a human pluripotent cell to a human lung progenitor cell (e.g., a cell committed to the lung lineage) and/or further differentiation steps to differentiated lung cells can be used with the methods described herein. Provided herein are examples of different signaling pathways and their agonists/antagonists that are useful in a variety of differentiation methods. Such agents can be used alone or in combination with other agents.

TGF-β Signaling Pathway Modulation:

In some embodiments, one or more TGF-β agonists are used to promote a particular differentiation step of a pluripotent cell (e.g., during generation of anterior foregut endoderm). In such embodiments, an activating agent specific for TGF-β signaling can be a TGF-β polypeptide or an active fragment thereof, a fusion protein comprising a TGF-β polypeptide or an active fragment thereof, an agonist antibody to a TGF-β receptor, or a small molecule agonist of a TGF-β receptor.

In other embodiments, one or more TGF-β antagonists can be used to permit differentiation of a pluripotent cell (e.g., for inducing Nkx2.1 expression, the first step towards commitment to lung lineage). In such embodiments, an antagonist for TGF-β signaling can be a polypeptide inhibitor or a fragment thereof, a dominant negative fusion protein, an antagonist antibody to a TGF-β receptor or a small molecule antagonist of a TGF-β receptor.

The Transforming growth factor beta (TGF-β) signaling pathway is involved in many cellular processes in both the adult organism and the developing embryo including cell growth, cell differentiation, apoptosis, cellular homeostasis and other cellular functions. TGF-β superfamily ligands bind to a type II receptor, which recruits and phosphorylates a type I receptor. The type I receptor then phosphorylates receptor-regulated SMADs (R-SMADs) which then bind the coSMAD SMAD4. R-SMAD/coSMAD complexes accumulate in the nucleus where they act as transcription factors and participate in the regulation of target gene expression.

TGF-β1 is a prototypic member of a family of cytokines including the TGF-βs, activins, inhibins, bone morphogenetic proteins and Mullerian-inhibiting substance. Smad proteins are exemplary downstream signal transduction factors in the TGF-beta pathway and therefore, in some embodiments, can be activated directly to effect differentiation to a human lung cell progenitor phenotype (e.g., by treating a cell with an activator of a Smad protein). Exemplary Smad activators include, but are not limited to, Smad proteins or functional peptides or fragments thereof (e.g., Smad1, Smad5, Smad8), BMP2, BMP4, and Mullerian inhibiting substance (MIS). Activin ligands transduce signals in a manner similar to TGF-β ligands. Activins bind to and activate ALK receptors, which in turn phosphorylate Smad proteins such as Smad2 and Smad3. The consequent formation of a hetero-Smad complex with Smad4 results in the activin-induced regulation of gene transcription.

Some non-limiting examples of small molecule inhibitors of TGF-β receptors include 2-(3-(6-Methylpyridin-2-yl)-1H-pyrazol-4-yl)-1,5 napththyridine, [3-(Pyridin-2-yl)-4-(4-quinoyl)]-1H-pyrazole, and 3-(6-Methylpyridin-2-yl)-4-(4- quinolyl)-1-phenylthiocarbamoyl-1H-pyrazole, which can be purchased from Calbiochem (San Diego, Calif.). Other small molecule inhibitors include, but are not limited to, SB-431542 (see e.g., Halder et al., 2005; *Neoplasia* 7(5): 509-521), SM16 (see e.g., Fu, K et al., 2008; *Arteriosclerosis, Thrombosis and Vascular Biology* 28(4):665), and SB-505124 (see e.g., Dacosta Byfield, S., et al., 2004; *Molecular Pharmacology* 65:744-52), among others. Additional TGF-□ receptor antagonists are known in the art.

In some embodiments, the dosage range useful for a TGF-β antagonist (e.g., A8301) is between 0.1 and 10 µM, for example between 0.1 and 1 µM, between 0.1 and 0.5 µM, between 0.1 and 2 µM, between 0.1 and 3 µM, between 0.1 and 4 µM, between 0.1 and 5 µM, between 0.1 and 6 µM, between 0.1 and 7 µM, between 0.1 and 8 µM, between 0.1 and 9 µM, between 0.5 and 2 µM, between 0.5 and 5 µM, between 1 and 3 µM, between 2 and 4 µM, between 2 and 6 µM, between 2 and 7 µM, between 5 and 10 µM, between 6 and 10 µM, between 7 and 10 µM, between 8 and 10 µM, between 9 and 10 µM. In some embodiments the TGF-β antagonist is used at a dose of e.g., at least 0.1 µM, at least 0.2 µM, at least 0.3 µM, at least 0.4 µM, at least 0.5 µM, at least 0.6 µM, at least 0.7 µM, at least 0.8 µM, at least 0.9 µM, at least 1 µM, at least 1.2 µM, at least 1.3 µM, at least 1.4 µM, at least 1.5 µM, at least 1.6 µM, at least 1.7 µM, at least 1.8 µM, at least 1.9 µM, at least 2 µM, at least 2.5 µM, at least 3 µM, at least 3.5 µM, at least 4 µM, at least 4.5 µM, at least 5 µM, at least 5.5 µM, at least 6 µM, at least 6.5 µM, at least 7 µM, at least 7.5 µM, at least 8 µM, at least 8.5 µM, at least 9 µM, at least 9.5 µM, at least 1 µM or more.

BMP Receptor Signaling Pathway Modulation

BMP2 and BMP4 both signal through the type I receptor (ALK3), while BMP7 binds to a separate type I receptor (ALK2). See e.g., von Bubnoff A et al., *Developmental Biology* (2001) 239:1-14; Chen D. et al., *Growth Factors* (2004) 22(4):233-241; Sieber C. et al., *Cytokine and Growth Factor Rev.* (2009) 20:343-355; and Miyazono K et al., *Journal of Biochemistry* (2010) 147(1):35-51.

Typically, BMP2 and BMP4 bind to a BMP receptor I/II complex, leading to phosphorylation of Smads 1/5/8, followed by formation of heterotrimeric complexes with Smad4. These complexes translocate to the nucleus and activate expression of target genes (von Bubnoff A et al., *Developmental Biology* (2001) 239:1-14; Chen D. et al., *Growth Factors* (2004) 22(4):233-241; Sieber C. et al., *Cytokine and Growth Factor Rev.* (2009) 20:343-355; and Miyazono K et al., *Journal of Biochemistry* (2010) 147(1): 35-51). Besides Smad1/5/8-mediated transcription, BMP-induced receptor complexes can activate the mitogen-activated protein kinase (MAPK) pathway via ERK, JNK, or p38 (Kozawa O et al., *Journal of Cellular Biochemistry* 84:583-589).

BMP Receptor Pathway Activation:

In some embodiments, a BMP agonist is used with the methods described herein for differentiation of a human lung progenitor cell. In one embodiment, the BMP receptor is a receptor that signals through the SMAD pathway (e.g., ALK3). In other embodiments, the BMPs used with the methods described herein are BMP2 and/or BMP4.

In one embodiment, one or more BMP agonists are used to promote a particular differentiation step of a pluripotent cell. In such embodiments, an activating agent specific for BMP signaling can be a BMP polypeptide or an active fragment thereof, a fusion protein comprising a BMP polypeptide or an active fragment thereof, an agonist antibody to a BMP receptor, or a small molecule agonist of a BMP receptor.

In some embodiments, the dosage range useful for BMP4 is between 1 and 500 nM, for example between 1 and 400 nM, between 1 and 300 nM, between 1 and 200 nM, between 1 and 100 nM, between 1 and 50 nM, between 1 and 25 nM, between 1 and 10 nM, between 1 and 5 nM, between 1 and 2 nM, between 10 and 300 nM, between 15 and 250 nM, between 20 and 250 nM, between 20 and 200 nM, between 30 and 200 nM, between 40 and 200 nM, between 50 and 200 nM, between 60 and 200 nM, between 70 and 200 nM, between 80 and 200 nM, between 90 and 200 nM, between 100 and 200 nM, between 150 and 200 nM, between 150 nM and 300 nM, between 175 and 300 nM, between 200 nM and 300 nM, between 200 nM and 400 nM, between 200 nM and 500 nM.

In some embodiments the dose of BMP4 is e.g., at least 1 nM, at least 2 nM, at least 5 nM, at least 10 nM, at least 20 nM, at least 30 nM, at least 40 nM, at least 50 nM, at least 60 nM, at least 70 nM, at least 80 nM, at least 90 nM, at least 100 nM, at least 110 nM, at least 120 nM, at least 130 nM, at least 140 nM, at least 150 nM, at least 160 nM, at least 170 nM, at least 180 nM, at least 190 nM, at least 200 nM, at least 225 nM, at least 250 nM, at least 275 nM, at least 300 nM, at least 400 nM, at least 500 nM or more.

In some embodiments, the dosage range useful for BMP7 is between 1 and 200 ng/mL, for example between 1 and 100 ng/mL, between 1 and 50 ng/mL, between 1 and 25 ng/mL, between 1 and 10 ng/mL, between 1 and 5 ng/mL, between 1 and 2 ng/mL, between 10 and 200 ng/mL, between 15 and 200 ng/mL, between 20 and 200 ng/mL, between 30 and 200 ng/mL, between 40 and 200 ng/mL, between 50 and 200 ng/mL, between 60 and 200 ng/mL, between 70 and 200 ng/mL, between 80 and 200 ng/mL, between 90 and 200 ng/mL, between 100 and 200 ng/mL, or between 150 and 200 ng/mL.

In some embodiments the dose of BMP7 is e.g., at least 1 ng/mL, at least 2 ng/mL, at least 5 ng/mL, at least 10 ng/mL, at least 20 ng/mL, at least 30 ng/mL, at least 40 ng/mL, at least 50 ng/mL, at least 60 ng/mL, at least 70 ng/mL, at least 80 ng/mL, at least 90 ng/mL, at least 100 ng/mL, at least 110 ng/mL, at least 120 ng/mL, at least 130 ng/mL, at least 140 ng/mL, at least 150 ng/mL, at least 160 ng/mL, at least 170 ng/mL, at least 180 ng/mL, at least 190 ng/mL, at least 200 ng/mL, or more.

BMP Receptor Pathway Inhibition:

In some embodiments, a BMP antagonist is used with the methods described herein for differentiation of a human foregut endoderm cell to a lung progenitor cell. In one embodiment, the BMP antagonist is dorsomorphin.

In one embodiment, one or more BMP receptor pathway antagonists are used to promote a particular differentiation step of a pluripotent cell. In such embodiments, an inhibitor specific for BMP signaling can be a polypeptide or fragment thereof, an shRNA or siRNA directed against a BMP receptor, an antagonist antibody to a BMP receptor, or a small molecule antagonist of a BMP receptor.

In some embodiments, the dosage range useful for a BMP pathway inhibitor is between 1 and 500 nM, for example between 1 and 400 nM, between 1 and 300 nM, between 1 and 200 nM, between 1 and 100 nM, between 1 and 50 nM, between 1 and 25 nM, between 1 and 10 nM, between 1 and 5 nM, between 1 and 2 nM, between 10 and 300 nM, between 15 and 250 nM, between 20 and 250 nM, between 20 and 200 nM, between 30 and 200 nM, between 40 and 200 nM, between 50 and 200 nM, between 60 and 200 nM, between 70 and 200 nM, between 80 and 200 nM, between 90 and 200 nM, between 100 and 200 nM, between 150 and 200 nM, between 150 nM and 300 nM, between 175 and 300 nM, between 200 nM and 300 nM, between 200 nM and 400 nM, between 200 nM and 500 nM.

In some embodiments the dose of the BMP pathway antagonist is e.g., at least 1 nM, at least 2 nM, at least 5 nM, at least 10 nM, at least 20 nM, at least 30 nM, at least 40 nM, at least 50 nM, at least 60 nM, at least 70 nM, at least 80 nM, at least 90 nM, at least 100 nM, at least 110 nM, at least 120 nM, at least 130 nM, at least 140 nM, at least 150 nM, at least 160 nM, at least 170 nM, at least 180 nM, at least 190 nM, at least 200 nM, at least 225 nM, at least 250 nM, at least 275 nM, at least 300 nM, at least 400 nM, at least 500 nM or more.

MAPKK/ERK Inhibitors:

Provided herein are methods for differentiating human lung progenitor cells to a population of more differentiation cells, wherein the methods comprise treatment with a MAPKK/ERK inhibitor.

Mitogen activated protein kinase (MAPK) signaling pathways are involved in cellular events such as growth, differentiation and stress responses (J. Biol. Chem. (1993) 268, 14553-14556). Four parallel MAPK pathways have been identified to date: ERK1/ERK2, JNK, p38 and ERK5. These pathways are linear kinase cascades in that MAPKKK phosphorylates and activates MAPKK, and MAPKK phosphorylates and activates MAPK. To date, seven MAPKK homologs (MEK1, MEK2, MKK3, MKK4/SEK, MEK5, MKK6, and MKK7) and four MAPK families (ERK1/2, JNK, p38, and ERK5) have been identified. Activation of these pathways regulates the activity of a number of substrates through phosphorylation. These substrates include: transcription factors such as TCF, c-myc, ATF2 and the AP-1 components, fos and Jun; cell surface components EGF-R; cytosolic components including PHAS-T, p90$^{rsk}$, cPLA$_2$ and c-Raf-1; and cytoskeleton components such as tau and MAP2. MAPK signaling cascades are involved in controlling cellular processes including proliferation, differentiation, apoptosis, and stress responses.

MEK occupies a strategic downstream position in the Mek/Erk pathway catalyzing the phosphorylation of its MAPK substrates, ERK1 and ERK2. Anderson et al. Nature 1990, v. 343, pp. 651-653. In the ERK pathway, MAPKK corresponds with MEK (MAP kinase ERK Kinase) and the MAPK corresponds with ERK (Extracellular Regulated Kinase).

Some non-limiting examples of MAPK and/or ERK pathway inhibitors include SL327, U0126, SP600125, PD98059, SB203580, and CAY10561. Additional MAPK and/or ERK pathway inhibitors that can be used with the methods described herein are known to those of skill in the art.

In some embodiments, the dosage range useful for a MAPKK/ERK antagonist (e.g., PD98059) is between 0.1 and 5 µM, for example, between 0.1 and 4 µM, between 0.1 and 3 µM, between 0.1 and 2 µM, between 0.1 and 1 µM, between 0.1 and 0.5 µM, between 0.5 and 3 µM, between 0.5 and 2 µM, between 0.5 and 1 µM, between 1 and 2 µM, between 1.5 and 2 µM, between 1 and 1.5 µM, between 2 and 5 µM, between 3 and 5 µM, between 4 and 5 µM.

In some embodiments, the dose of a MAPKK/ERK antagonist is e.g., at least 0.1 µM, at least 0.5 µM, at least 1 µM, at least 1.1 µM, at least 1.2 µM, at least 1.3 µM, at least 1.4 µM, at least 1.5 µM, at least 1.6 µM, at least 1.7 µM, at least 1.8 µM, at least 1.9 µM, at least 2 µM, at least 2.5 µM, at least 3 µM, at least 4 µM, at least 5 µM or more.

FGF Activation:

Fibroblast growth factors, or FGFs, are a family of growth factors that play a role in angiogenesis, wound healing, and embryonic development. FGFs and functional fragments or analogs thereof are useful for differentiating human lung progenitor cells to a more differentiated phenotype as described herein.

FGFs are heparin-binding proteins, which interact with cell-surface-associated heparan sulfate proteoglycans to effect FGF signaling. At least 22 different members of the FGF family have been identified. FGF1, FGF2, FGF3, FGF4, FGF5, FGF6, FGF7, FGF8, FGF9, and FGF10 bind and effect signaling through fibroblast growth receptors (FGFR).

FGFs induce mitosis in a variety of cell types and also have regulatory, morphological, and endocrine effects. FGFs function throughout embryonic development and aid in mesoderm induction, antero-posterior patterning, limb development, neural induction and neural development. In one embodiment, a preferred FGF for use with the methods described herein is FGF7, which is also known in the art as Keratinocyte Growth Factor (KGF).

In some embodiments, the dosage range useful for FGF7 or FGF2 is between 10 and 200 ng/mL, for example between 10 and 100 ng/mL, between 10 and 50 ng/mL, between 15 and 200 ng/mL, between 20 and 200 ng/mL, between 30 and 200 ng/mL, between 40 and 200 ng/mL, between 50 and 200 ng/mL, between 60 and 200 ng/mL, between 70 and 200 ng/mL, between 80 and 200 ng/mL, between 90 and 200 ng/mL, between 100 and 200 ng/mL, or between 150 and 200 ng/mL.

In some embodiments, the dose of FGF7 or FGF2 is e.g., at least 10 ng/mL, at least 20 ng/mL, at least 30 ng/mL, at least 40 ng/mL, at least 50 ng/mL, at least 60 ng/mL, at least 70 ng/mL, at least 80 ng/mL, at least 90 ng/mL, at least 100 ng/mL, at least 110 ng/mL, at least 120 ng/mL, at least 130 ng/mL, at least 140 ng/mL, at least 150 ng/mL, at least 160 ng/mL, at least 170 ng/mL, at least 180 ng/mL, at least 190 ng/mL, at least 200 ng/mL, at least 225 ng/mL, at least 250 ng/mL or more.

Wnt Pathway Modulation:

Without wishing to be bound by theory, Wnt proteins and their cognate receptors signal through at least two distinct intracellular pathways. The "canonical" Wnt signaling pathway, (referred to herein as the Wnt/β-catenin pathway) involves Wnt signaling via β-catenin to activate transcription through TCF-related proteins (van de Wetering et al. (2002) Cell 109 Suppl: S13-9; Moon et al. (2002) Science 296(5573): 1644-6). A non-canonical alternative pathway exists, in which Wnt activates protein kinase C (PKC), calcium/calmodulin-dependent kinase II (CaMKII), JNK and Rho-GTPases (Veeman et al. (2003) Dev Cell 5(3): 367-77), and is often involved in the control of cell polarity.

Wnt Antagonists:

Provided herein are methods for differentiating human lung progenitor cells to a more differentiated stem cell phenotype by contacting a lung progenitor cell with a Wnt antagonist.

As used herein, the term "Wnt antagonist" or "Wnt inhibitor" refers to any agent that inhibits the Wnt/β-catenin pathway, or enhances the activity and/or expression of inhibitors of Wnt/β-catenin signaling, for example activators or enhancers of GSK-3β activity. A Wnt inhibitory agent as used herein can suppress the Wnt/β-catenin pathway at any point along the pathway, for example, but not limited to decreasing the expression and/or activity of Wnt, or β-catenin or Wnt dependent genes and/or proteins, and increasing the expression and/or activity of endogenous inhibitors of Wnt and/or β-catenin or increasing the expression and/or activity of endogenous inhibitors of components of the Wnt/β-catenin pathway, for example increasing the expression of GSK-3β.

Some non-limiting examples of Wnt antagonists include Wnt pathway inhibitor V (also known as (E)-4-(2,6-Difluorostyryl)-N,N-dimethylaniline), IWR-1 endo, IWP-2, CCT036477, and a peptide comprising the sequence t-Boc-NH-Met-Asp-Gly-Cys-Glu-Leu-CO2H (SEQ ID NO: 1).

In some embodiments, the dosage range useful for a Wnt antagonist (e.g. IWR-1) is between 20 and 200 ng/mL, between 30 and 200 ng/mL, between 40 and 200 ng/mL, between 50 and 200 ng/mL, between 60 and 200 ng/mL, between 70 and 200 ng/mL, between 80 and 200 ng/mL, between 90 and 200 ng/mL, between 100 and 200 ng/mL, or between 150 and 200 ng/mL.

In some embodiments the dose of a Wnt antagonist is e.g., at least 20 ng/mL, at least 30 ng/mL, at least 40 ng/mL, at least 50 ng/mL, at least 60 ng/mL, at least 70 ng/mL, at least 80 ng/mL, at least 90 ng/mL, at least 100 ng/mL, at least 110 ng/mL, at least 120 ng/mL, at least 130 ng/mL, at least 140 ng/mL, at least 150 ng/mL, at least 160 ng/mL, at least 170 ng/mL, at least 180 ng/mL, at least 190 ng/mL, at least 200 ng/mL, or more.

Wnt Agonists:

Provided herein are methods for differentiating a human foregut endoderm cell to a more differentiated cell type, e.g., to a human lung progenitor cell by contacting a cell with a Wnt agonist.

As used herein, the term "Wnt agonist" refers to any agent that activates the Wnt/β-catenin pathway, or inhibits the activity and/or expression of inhibitors of Wnt/β-catenin signaling, for example antagonists or inhibitors of GSK-3β activity. A Wnt activating agent as used herein can enhance signaling through the Wnt/β-catenin pathway at any point along the pathway, for example, but not limited to increasing the expression and/or activity of Wnt, or β-catenin or Wnt dependent genes and/or proteins, and decreasing the expression and/or activity of endogenous inhibitors of Wnt and/or β-catenin or decreasing the expression and/or activity of endogenous inhibitors of components of the Wnt/□-catenin pathway, for example decreasing the expression of GSK-3β.

Some non-limiting examples of Wnt pathway agonists include CHIR9902, 2-amino-4-[3,4-(methylenedioxy)benzyl-amino]-6-(3-methoxyphenyl)pyrimidine, BIO, (2'Z, 3'E)-6-Bromoindirubin-3'-oxime, 5-(Furan-2-yl)-N-(3-(1H-imidazol-1-yl)propyl)-1,2-oxazole-3-carboxamide, and SKL2001.

In some embodiments, the dosage range useful for a Wnt agonist (e.g. CHIR9902) is between 20 and 200 ng/mL, between 30 and 200 ng/mL, between 40 and 200 ng/mL, between 50 and 200 ng/mL, between 60 and 200 ng/mL, between 70 and 200 ng/mL, between 80 and 200 ng/mL, between 90 and 200 ng/mL, between 100 and 200 ng/mL, or between 150 and 200 ng/mL.

In some embodiments the dose of a Wnt agonist is e.g., at least 20 ng/mL, at least 30 ng/mL, at least 40 ng/mL, at least 50 ng/mL, at least 60 ng/mL, at least 70 ng/mL, at least 80 ng/mL, at least 90 ng/mL, at least 100 ng/mL, at least 110 ng/mL, at least 120 ng/mL, at least 130 ng/mL, at least 140 ng/mL, at least 150 ng/mL, at least 160 ng/mL, at least 170 ng/mL, at least 180 ng/mL, at least 190 ng/mL, at least 200 ng/mL, or more.

In some embodiments, the dosage range useful for a Wnt agonist (e.g., CHIR9902) is between 0.1 and 5 µM, for example, between 0.1 and 4 µM, between 0.1 and 3 µM, between 0.1 and 2 µM, between 0.1 and 1 µM, between 0.1 and 0.5 µM, between 0.5 and 3 µM, between 0.5 and 2 µM, between 0.5 and 1 µM, between 1 and 2 µM, between 1.5 and 2 µM, between 1 and 1.5 µM, between 2 and 5 µM, between 3 and 5 µM, between 4 and 5 µM.

In some embodiments, the dose of a Wnt agonist (e.g., CHIR9902) is e.g., at least 0.1 µM, at least 0.5 µM, at least 1 µM, at least 1.1 µM, at least 1.2 µM, at least 1.3 µM, at least 1.4 µM, at least 1.5 µM, at least 1.6 µM, at least 1.7 µM, at least 1.8 µM, at least 1.9 µM, at least 2 µM, at least 2.5 µM, at least 3 µM, at least 4 µM, at least 5 µM or more.

PI3 Kinase Inhibitors:

Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

As used herein, the term "PI3 kinase inhibitor" or "PI3 kinase antagonist" refers to any agent that inhibits the activity of PI3 kinase. Some non-limiting examples of a PI3 kinase inhibitor useful with the methods described herein include LY294002, wortmannin, PIK-75, ZSTK474, and Pp242.

In some embodiments, the dosage range useful for a PI3 kinase inhibitor (e.g., ZSTK474, or PIK-75) is between 0.1 and 5 µM, for example, between 0.1 and 4 µM, between 0.1 and 3 µM, between 0.1 and 2 µM, between 0.1 and 1 µM, between 0.1 and 0.5 µM, between 0.5 and 3 µM, between 0.5 and 2 µM, between 0.5 and 1 µM, between 1 and 2 µM, between 1.5 and 2 µM, between 1 and 1.5 µM, between 2 and 5 µM, between 3 and 5 µM, between 4 and 5 µM.

In some embodiments, the dose of a PI3 kinase inhibitor (e.g., ZSTK474, or PIK-75) is e.g., at least 0.1 µM, at least 0.5 µM, at least 1 µM, at least 1.1M, at least 1.2 µM, at least 1.3 µM, at least 1.4 µM, at least 1.5 µM, at least 1.6 µM, at least 1.7 µM, at least 1.8 µM, at least 1.9 µM, at least 2 µM, at least 2.5 µM, at least 3 µM, at least 4 µM, at least 5 µM or more.

Detection of Human Lung Progenitors

Provided herein are methods for differentiating or redifferentiating a pluripotent stem cell (e.g., an anterior foregut endoderm cell, a definitive endoderm cell, an ES cell or an iPSC) to a human lung progenitor cell, and further isolating human lung progenitors based on a pattern of cell surface markers. Also provided herein are compositions of human lung progenitor cells having particular characteristics, such as the presence of one or more cell surface markers that are lung cell specific (e.g., $CD47^{hi}/CD26^{lo}$). Alternatively, or in addition, the human lung progenitor cell compositions described herein lack markers of embryonic stem cells or induced pluripotent stem cells. In one embodiment of the methods described herein, one or more cell surface markers are used to determine the degree of differentiation along the spectrum of embryonic stem cells or iPSCs to fully differentiated lung cells.

Cells isolated using one or more lung specific markers as described herein are useful in in vitro drug screening assays and in drug development assays. Further, the cells can be personalized by using the subject's own somatic cells, reprogramming them to an induced pluripotent stem cell phenotype and then differentiating the iPSCs along the lung cell lineage. Personalized cells can be used in vitro to determine the degree of drug responsiveness that is specific to the subject from which the cells were derived or the cells can be used in a pharmaceutical or biologic composition for the treatment of lung disease or injury.

Cell surface markers, particularly stem cell surface markers, are useful with the methods and compositions described herein to identify the differentiation or dedifferentiation state of a cell. For example, during reprogramming of a somatic cell to an induced pluripotent stem cell the activation of stem cell markers can be used to confirm that the somatic cell has been dedifferentiated (either partially or completely). Alternatively, during differentiation of an ES cell or an iPSC to a human lung progenitor cell, the activation of lung-specific markers can be used to confirm the degree of differentiation that the stem cell has undergone. In addition, the activation or deactivation of particular lung-specific markers can be used to determine the degree of multipotency of a human lung progenitor cell. This can be achieved by comparing the lung-specific markers present on, or expressed by the cell with the marker profile of lung cells during development and inferring the degree of multipotency of the differentiated cell based on the known degree of multipotency of the corresponding lung cell during embryonic development.

Marker-specific agents can be used to recognize stem cell markers, for instance labeled antibodies that recognize and bind to cell-surface markers or antigens on desired stem cells. Antibodies or similar agents specific for a given marker, or set of markers, can be used to separate and isolate the desired stem cells using fluorescent activated cell sorting (FACS), panning methods, magnetic particle selection, particle sorter selection and other methods known to persons skilled in the art, including density separation (Xu et al. (2002) Circ. Res. 91:501; U.S.S.N. 20030022367) and separation based on other physical properties (Doevendans et al. (2000) J. Mol. Cell. Cardiol. 32:839-851).

Alternatively, genetic selection methods can be used, where a progenitor or stem cell can be genetically engineered to express a reporter protein operatively linked to a tissue-specific promoter and/or a specific gene promoter; therefore the expression of the reporter can be used for positive selection methods to isolate and enrich the desired stem cell. For example, a fluorescent reporter protein can be expressed in the desired stem cell by genetic engineering methods to operatively link the marker protein to a promoter active in a desired stem cell (Klug et al. (1996) J. Clin. Invest. 98:216-224; U.S. Pat. No. 6,737,054). In some embodiments, cells from which the human lung progenitor cells are derived are not modified using genetic means. Other approaches for positive selection include drug selection, for instance as described by Klug et al., supra, involving enrichment of desired cells by density gradient centrifugation. Negative selection can be performed, selecting and removing cells with undesired markers or characteristics, for example fibroblast markers, epithelial cell markers etc.

Undifferentiated ES cells express genes that can be used as markers to detect the presence of undifferentiated cells. The polypeptide products of such genes can be used as markers for negative selection. For example, see U.S.S.N. 2003/0224411 A1; Bhattacharya (2004) Blood 103(8):2956-64; and Thomson (1998), supra., each herein incorporated by reference. Human ES cell lines express cell surface markers that characterize undifferentiated nonhuman primate ES and human EC cells, including, but not limited to, stage-specific embryonic antigen (SSEA)-3, SSEA-4, TRA-1-60, TRA-1-81, and alkaline phosphatase. The globo-series glycolipid GL7, which carries the SSEA-4 epitope, is formed by the addition of sialic acid to the globo-series glycolipid Gb5, which carries the SSEA-3 epitope. Thus, GL7 reacts with antibodies to both SSEA-3 and SSEA-4. Undifferentiated human ES cell lines do not stain for SSEA-1, but differentiated cells stain strongly for SSEA-1. Methods for proliferating hES cells in the undifferentiated form are described in WO 99/20741, WO 01/51616, and WO 03/020920, the contents of which are herein incorporated by reference in their entireties.

Exemplary cell surface markers expressed on lung progenitor cells include, but are not limited to, $CD47^{hi}/CD26^{lo}$, SFTA3, CPM, NFIB, NKX2-1, CRH, JUN, MECOM, SOX2, HES1, HOXA1, FOXA2, FOXA1, GATA6, GRHL2, IRX1, IRX2, ELF3, ELF5, HNFIB, FOXP2, HOXA4, HOXC4, SHH, EPCAM, CD166, CD227, SOX2, SOX9, and/or LAMA2. In other embodiments, the human lung progenitor cells described herein lack markers of differentiated lung cells and cells not committed to the lung lineage (e.g., thyroid progenitor cells, brain/neuronal progenitor cells). Such markers include, but are not limited to, lowSCG1A1, SFTPC, SCGB3A2, SFTPB, TP63, ICAM1, IL8, ASCL1, FOXJ1, SCGB1A1, ITGB6, SIX3, SIX6, OTX1 or PAX8.

In some embodiments, the human lung progenitor cells are an enriched population of cells; that is, the percentage of human lung progenitor cells (e.g., percent of cells) in a population of cells is at least 10% of the total number of cells in the population. For example, an enriched population comprises at least 15% human lung progenitor cells, at least 20%, at least 30%, at least 40%, at least 50%, at least 60%, at least 70%, at least 80%, at least 90%, at least 95%, at least 99% or even 100% of the population comprises human lung progenitor cells. In some embodiments, a population of cells comprises at least 100 cells, at least 500 cells, at least 1000 cells, at least $1\times10^4$ cells, at least $1\times10^5$ cells, at least $1\times10^6$ cells, at least $1\times10^7$ cells, at least $1\times10^8$ cells, at least $1\times10^9$ cells, at least $1\times10^{10}$ cells, at least $1\times10^{11}$ cells, at least $1\times10^{12}$ cells, at least $1\times10^{13}$ cells, at least $1\times10^{14}$ cells, at least $1\times10^{15}$ cells, or more.

In one embodiment, the human lung progenitor cells described herein are not tumor cells or cancer cells. In such embodiments, the human lung progenitor cell can be distinguished from a tumor cell or cancer cell using e.g., a cell marker profile.

Therapeutic Compositions

The methods of administering human lung progenitors to a subject as described herein involve the use of therapeutic compositions comprising lung progenitor cells. Therapeutic compositions contain a physiologically tolerable carrier together with the cell composition and optionally at least one additional bioactive agent as described herein, dissolved or dispersed therein as an active ingredient. In a preferred embodiment, the therapeutic composition is not substantially immunogenic when administered to a mammal or human patient for therapeutic purposes, unless so desired. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset, transplant rejection, allergic reaction, and the like. A pharmaceutically acceptable carrier will not promote the raising of an immune response to an agent with which it is admixed, unless so desired. The preparation of a composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared.

In general, the human lung progenitor cells described herein are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the human lung progenitor cells as described herein using routine experimentation.

A cell composition can also be emulsified or presented as a liposome composition, provided that the emulsification procedure does not adversely affect cell viability. The cells and any other active ingredient can be mixed with excipients which are pharmaceutically acceptable and compatible with the active ingredient and in amounts suitable for use in the therapeutic methods described herein.

Additional agents included in a cell composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions as described herein that is effective in the treatment of a particular disorder or condition will depend on the nature of the disorder or condition, and can be determined by standard clinical techniques.

In some embodiments, the therapeutic compositions described herein are personalized to a particular subject by obtaining a somatic cell, reprogramming the cell, and then redifferentiating the reprogrammed cell along the lung lineage (e.g., using the methods in the working Examples) for generation of a therapeutic composition for the same subject (i.e., somatic cells).

Scaffold Compositions

Biocompatible synthetic, natural, as well as semi-synthetic polymers can be used for synthesizing polymeric particles that can be used as a scaffold material. In general, for the practice of the methods described herein, it is preferable that a scaffold biodegrades such that the lung progenitor cells can be isolated from the polymer prior to implantation or such that the scaffold degrades over time in a subject and does not require removal. Thus, in one embodiment, the scaffold provides a temporary structure for growth and/or delivery of human lung progenitor cells to a subject in need thereof. In some embodiments, the scaffold permits human cell progenitors to be grown in a shape suitable for transplantation or administration into a subject in need thereof, thereby permitting removal of the scaffold prior to implantation and reducing the risk of rejection or allergic response initiated by the scaffold itself.

Examples of polymers which can be used include natural and synthetic polymers, although synthetic polymers are preferred for reproducibility and controlled release kinetics. Synthetic polymers that can be used include biodegradable polymers such as poly(lactide) (PLA), poly(glycolic acid) (PGA), poly(lactide-co-glycolide) (PLGA), and other polyhydroxyacids, poly(caprolactone), polycarbonates, polyamides, polyanhydrides, polyphosphazene, polyamino acids, polyortho esters, polyacetals, polycyanoacrylates and biodegradable polyurethanes; non-biodegradable polymers such as polyacrylates, ethylene-vinyl acetate polymers and other acyl-substituted cellulose acetates and derivatives thereof, polyurethanes, polystyrenes, polyvinyl chloride, polyvinyl fluoride, poly(vinyl imidazole), chlorosulphonated polyolefins, and polyethylene oxide. Examples of biodegradable natural polymers include proteins such as albumin, collagen, fibrin, silk, synthetic polyamino acids and prolamines; polysaccharides such as alginate, heparin; and other naturally occurring biodegradable polymers of sugar units. Alternately, combinations of the aforementioned polymers can be used.

PLA, PGA and PLA/PGA copolymers are particularly useful for forming biodegradable scaffolds. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. Methods of preparing polylactides are well documented in the patent literature. The following U.S. Patents, the teachings of which are hereby incorporated by reference, describe in detail suitable polylactides, their properties and their preparation: U.S. Pat. No. 1,995,970 to Dorough; U.S. Pat. No. 2,703,316 to Schneider; U.S. Pat. No. 2,758,987 to Salzberg; U.S. Pat. No. 2,951,828 to Zeile; U.S. Pat. No. 2,676,945 to Higgins; and U.S. Pat. Nos. 2,683,136; 3,531,561 to Trehu.

PGA is a homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer. PGA polymers and their properties are described in more detail in Cyanamid Research Develops World's First Synthetic Absorbable Suture", Chemistry and Industry, 905 (1970).

Fibers can be formed by melt-spinning, extrusion, casting, or other techniques well known in the polymer processing area. Preferred solvents, if used to remove a scaffold prior to implantation, are those which are completely removed by the processing or which are biocompatible in the amounts remaining after processing.

Polymers for use in the matrix should meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy.

Scaffolds can be of any desired shape and can comprise a wide range of geometries that are useful for the methods described herein. A non-limiting list of shapes includes, for example, hollow particles, tubes, sheets, cylinders, spheres, and fibers, among others. In one embodiment, the scaffold is lung shaped and sized to ensure an appropriate fit within the chest cavity of the subject to be treated. The shape or size of the scaffold should not substantially impede cell growth, cell differentiation, cell proliferation or any other cellular process, nor should the scaffold induce cell death via e.g., apoptosis or necrosis. In addition, care should be taken to ensure that the scaffold shape permits appropriate surface area for delivery of nutrients from the surrounding medium to cells in the population, such that cell viability is not impaired. The scaffold porosity can also be varied as desired by one of skill in the art.

In some embodiments, attachment of the cells to a polymer is enhanced by coating the polymers with compounds such as basement membrane components, agar, agarose, gelatin, gum arabic, collagens types I, II, III, IV, and V, fibronectin, laminin, glycosaminoglycans, polyvinyl alcohol, mixtures thereof, and other hydrophilic and peptide attachment materials known to those skilled in the art of cell culture or tissue engineering. Examples of a material for coating a polymeric scaffold include polyvinyl alcohol and collagen.

In some embodiments, the scaffold can include decellularized lung tissue. Methods for producing decellularized lung tissue are known in the art, see e.g., WO2011/005306. Briefly, the process of decellularization involves chemically stripping lung tissue of its cells and removing the cellular debris, which leaves behind the structure of the extracellular matrix. The extracellular matrix can then be repopulated with human lung progenitor cells as described herein, and optionally with other bioactive agents. Such decellularized scaffolds can be prepared from a portion of the subject's own lung and therefore the risk of rejection or allergic reaction in response to the repopulated and administered scaffold can be minimized.

In some embodiments it can be desirable to add bioactive molecules to the scaffold. A variety of bioactive molecules can be delivered using the matrices described herein. These are referred to generically herein as "factors" or "bioactive factors".

In one embodiment, the bioactive factors include growth factors. Examples of growth factors include platelet derived growth factor (PDGF), transforming growth factor alpha or beta (TGFβ), bone morphogenic protein 4 (BMP4), fibroblastic growth factor 7 (FGF7), fibroblast growth factor 10 (FGF10), epidermal growth factor (EGF/TGFβ), vascular endothelium growth factor (VEGF), some of which are also angiogenic factors.

These factors are known to those skilled in the art and are available commercially or described in the literature. Bioactive molecules can be incorporated into the matrix and released over time by diffusion and/or degradation of the matrix, or they can be suspended with the cell suspension.

Treatment of Lung Disease/Disorders and Lung Injury

The methods and compositions provided herein relate to the generation and use of human lung progenitor cells. Accordingly, provided herein are methods for the treatment and prevention of a lung injury or a lung disease or disorder in a subject in need thereof. The methods described herein can be used to treat, ameliorate, prevent or slow the progression of a number of lung diseases or their symptoms, such as those resulting in pathological damage to lung or airway architecture and/or alveolar damage. The terms "respiratory disorder," "respiratory disease," "lung disease," "lung disorder," "pulmonary disease," and "pulmonary disorder," are used interchangeably herein and refer to any condition and/or disorder relating to respiration and/or the respiratory system, including the lungs, pleural cavity, bronchial tubes, trachea, upper respiratory tract, airways, or other components or structures of the airway system.

Such lung diseases include, but are not limited to, bronchopulmonary dysplasia (BPD), chronic obstructive pulmonary disease (COPD), cystic fibrosis, bronchiectasis, cor pulmonale, pneumonia, lung abcess, acute bronchitis, chronic bronchitis, emphysema, pneumonitis (e.g., hypersensitivity pneumonitis or pneumonitis associated with radiation exposure), alveolar lung diseases and interstitial lung diseases, environmental lung disease (e.g., associated with asbestos, fumes or gas exposure), aspiration pneumonia, pulmonary hemorrhage syndromes, amyloidosis, connective tissue diseases, systemic sclerosis, ankylosing spondylitis, pulmonary actinomycosis, pulmonary alveolar proteinosis, pulmonary anthrax, pulmonary edema, pulmonary embolus, pulmonary inflammation, pulmonary histiocytosis X, pulmonary hypertension, surfactant deficiencies, pulmonary hypoplasia, pulmonary neoplasia, pulmonary nocardiosis, pulmonary tuberculosis, pulmonary veno-occlusive disease, rheumatoid lung disease, sarcoidosis, postpneumonectomy, Wegener's granulomatosis, allergic granulomatosis, granulomatous vasculitides, eosinophilia, asthma and airway hyperreactivity (AHR) (e.g., mild intermittent asthma, mild persistent asthma, moderate persistent asthma, severe persistent asthma, acute asthma, chronic asthma, atopic asthma, allergic asthma or idiosyncratic asthma), allergic bronchopulmonary aspergillosis, chronic sinusitis, pancreatic insufficiency, lung or vascular inflammation, bacterial or viral infection, e.g., *Haemophilus influenzae, S. aureus, Pseudomonas aeruginosa* or respiratory syncytial virus (RSV) infection or an acute or chronic adult or pediatric respiratory distress syndrome (RDS) such as grade I, II, III or IV RDS or an RDS associated with, e.g., sepsis, pneumonia, reperfusion, atelectasis or chest trauma.

Chronic obstructive pulmonary diseases (COPDs) include those conditions where airflow obstruction is located at upper airways, intermediate-sized airways, bronchioles or parenchyma, which can be manifested as, or associated with, tracheal stenosis, tracheal right ventricular hypertrophy pulmonary hypertension, polychondritis, bronchiectasis, bronchiolitis, e.g., idiopathic bronchiolitis, ciliary dyskinesia, asthma, emphysema, connective tissue disease, bronchiolitis of chronic bronchitis or lung transplantation.

The methods described herein can also be used to treat or ameliorate acute or chronic lung diseases/disorders or their symptoms or complications, including airway epithelium injury, airway smooth muscle spasm or airway hyperresponsiveness, airway mucosa edema, increased mucus secretion, excessive T cell activation, or desquamation, atelectasis, cor pulmonale, pneumothorax, subcutaneous emphysema, dyspnea, coughing, wheezing, shortness of breath, tachypnea, fatigue, decreased forced expiratory volume in the 1st second ($FEV_1$), arterial hypoxemia, respiratory acidosis, inflammation including unwanted elevated levels of mediators such as IL-4, IL-5, IgE, histamine, substance P, neurokinin A, calcitonin gene-related peptide or arachidonic acid metabolites such as thromboxane or leukotrienes ($LTD_4$ or $LTC_4$), and cellular airway wall infiltration, e.g., by eosinophils, lymphocytes, macrophages or granulocytes.

Any of these and other respiratory or pulmonary conditions or symptoms are known in the art. See e.g., The Merck Manual, 17th edition, M. H. Beers and R. Berkow editors, 1999, Merck Research Laboratories, Whitehouse Station, N.J., ISBN 0911910-10-7, or in other references cited herein.

As used herein, the terms "administering," "introducing" and "transplanting" are used interchangeably in the context of the placement of cells, e.g. lung progenitor cells, as described herein into a subject, by a method or route which results in at least partial localization of the introduced cells at a desired site, such as a site of injury or repair, such that a desired effect(s) is produced. The cells e.g. lung progenitor cells, or their differentiated progeny (e.g. airway progenitor cells, basal cells, Clara cells, ciliated cells or goblet cells) can be implanted directly to the respiratory airways, or alternatively be administered by any appropriate route which results in delivery to a desired location in the subject where at least a portion of the implanted cells or components of the cells remain viable. The period of viability of the cells after administration to a subject can be as short as a few hours, e.g., twenty-four hours, to a few days, to as long as several years, i.e., long-term engraftment. For example, in some embodiments of the aspects described herein, an effective amount of lung progenitor cells is administered directly to the lungs of an infant suffering from bronchopulmonary dysplasia by intratracheal administration. In other embodiments, lung progenitor cells can be administered via an indirect systemic route of administration, such as an intraperitoneal or intravenous route.

When provided prophylactically, lung progenitor cells described herein can be administered to a subject in advance of any symptom of a lung disorder, e.g., early interstitial disease, an asthma attack or to a premature infant. Accordingly, the prophylactic administration of a lung progenitor cell population serves to prevent a lung disorder, as disclosed herein.

When provided therapeutically, lung progenitor cells are provided at (or after) the onset of a symptom or indication of a lung disorder, e.g., upon the onset of COPD.

In some embodiments of the aspects described herein, the lung progenitor cell population being administered according to the methods described herein comprises allogeneic lung progenitor cells obtained from one or more donors. As used herein, "allogeneic" refers to a lung progenitor cell or biological samples comprising lung progenitor cells obtained from one or more different donors of the same species, where the genes at one or more loci are not identical. For example, a lung progenitor cell population being administered to a subject can be derived from umbilical cord blood obtained from one more unrelated donor subjects, or from one or more non-identical siblings. In some embodiments, syngeneic lung progenitor cell populations can be used, such as those obtained from genetically identical animals, or from identical twins. In other embodiments of this aspect, the lung progenitor cells are autologous cells; that is, the lung progenitor cells are obtained or isolated from a subject and administered to the same subject, i.e., the donor and recipient are the same.

Depending on the disease/disorder or injury to be treated, as well as the location of the lung injury, either an undifferentiated human lung progenitor cell, or a differentiated cell thereof can be administered to the subject.

Administration and Efficacy

Provided herein are methods for treating a lung disease, a lung disorder, or a lung injury comprising administering human lung progenitor cells or differentiated progeny thereof to a subject in need thereof.

Measured or measurable parameters include clinically detectable markers of disease, for example, elevated or depressed levels of a clinical or biological marker, as well as parameters related to a clinically accepted scale of symptoms or markers for a disease or disorder. It will be understood, however, that the total daily usage of the compositions and formulations as disclosed herein will be decided by the attending physician within the scope of sound medical judgment. The exact amount required will vary depending on factors such as the type of disease being treated.

The term "effective amount" as used herein refers to the amount of a population of human lung progenitor cells or their progeny needed to alleviate at least one symptom of the lung injury or the lung disease or disorder, and relates to a sufficient amount of a composition to provide the desired effect, e.g., treat a subject having smoking induced-injury or cystic fibrosis. The term "therapeutically effective amount" therefore refers to an amount of human lung progenitor cells or a composition comprising human lung progenitor cells that is sufficient to promote a particular effect when administered to a typical subject, such as one who has or is at risk for a lung disease or disorder. An effective amount as used herein would also include an amount sufficient to prevent or delay the development of a symptom of the disease, alter the course of a symptom disease (for example but not limited to, slow the progression of a symptom of the disease), or reverse a symptom of the disease. It is understood that for any given case, an appropriate "effective amount" can be determined by one of ordinary skill in the art using routine experimentation.

In some embodiments, the subject is first diagnosed as having a disease or disorder affecting the lung tissue prior to administering the cells according to the methods described herein. In some embodiments, the subject is first diagnosed as being at risk of developing lung disease or disorder prior to administering the cells. For example, a premature infant can be at a significant risk of developing a lung disease or disorder.

For use in the various aspects described herein, an effective amount of human lung progenitor cells, comprises at least $10^2$ lung progenitor cells, at least $5 \times 10^2$ lung progenitor cells, at least $10^3$ lung progenitor cells, at least $5 \times 10^3$ lung progenitor cells, at least $10^4$ lung progenitor cells, at least $5 \times 10^4$ lung progenitor cells, at least $10^5$ lung progenitor cells, at least $2 \times 10^5$ lung progenitor cells, at least $3 \times 10^5$ lung progenitor cells, at least $4 \times 10^5$ lung progenitor cells, at least $5 \times 10^5$ lung progenitor cells, at least $6 \times 10^5$ lung progenitor cells, at least $7 \times 10^5$ lung progenitor cells, at least $8 \times 10^5$ lung progenitor cells, at least $9 \times 10^5$ lung progenitor cells, at least $1 \times 10^6$ lung progenitor cells, at least $2 \times 10^6$ lung progenitor cells, at least $3 \times 10^6$ lung progenitor cells, at least $4 \times 10^6$ lung progenitor cells, at least $5 \times 10^6$ lung progenitor cells, at least $6 \times 10^6$ lung progenitor cells, at least $7 \times 10^6$ lung progenitor cells, at least $8 \times 10^6$ lung progenitor cells, at least $9 \times 10^6$ lung progenitor cells, or multiples thereof. The lung progenitor cells can be derived from one or more donors, or can be obtained from an autologous source. In some embodiments of the aspects described herein, the lung progenitor cells are expanded in culture prior to administration to a subject in need thereof.

Exemplary modes of administration for use in the methods described herein include, but are not limited to, injection, intrapulmonary (including intranasal and intratracheal) infusion, inhalation as an aerosol (including intranasal), and implantation (with or without a scaffold material). "Injection" includes, without limitation, intravenous, intramuscular, intraarterial, intradermal, intraperitoneal, transtracheal and subcutaneous.

In some embodiments, a therapeutically effective amount of lung progenitor cells is administered using intrapulmonary administration, such as an intranasal or intratracheal route. In some aspects of these methods, a therapeutically effective amount of lung progenitor cells are administered using a systemic, such as an intraperitoneal or intravenous route. In other aspects of these methods, a therapeutically effective amount of lung progenitor cells is administered using both intrapulmonary and intraperitoneal administration. These methods are particularly aimed at therapeutic and prophylactic treatments of human subjects having, or at risk of having, a lung disease or disorder. The human lung progenitor cells described herein can be administered to a subject having any lung disease or disorder by any appropriate route which results in an effective treatment in the subject. In some embodiments of the aspects described herein, a subject having a lung disorder is first selected prior to administration of the cells.

In some embodiments, an effective amount of lung progenitor cells are administered to a subject by intrapulmonary administration or delivery. As defined herein, "intrapulmonary" administration or delivery refers to all routes of administration whereby a population of lung progenitor cells, e.g., $CD47^{hi}/CD26^{lo}$ lung progenitor cells, is administered in a way that results in direct contact of these cells with the airways of a subject, including, but not limited to, transtracheal, intratracheal, and intranasal administration. In some such embodiments, the cells are injected into the nasal passages or trachea. In some embodiments, the cells are directly inhaled by a subject. In some embodiments, intrapulmonary delivery of cells includes administration methods whereby cells are administered, for example as a cell suspension, to an intubated subject via a tube placed in the trachea or "tracheal intubation."

As used herein, "tracheal intubation" refers to the placement of a flexible tube, such as a plastic tube, into the trachea. The most common tracheal intubation, termed herein as "orotracheal intubation" is where, with the assistance of a laryngoscope, an endotracheal tube is passed through the mouth, larynx, and vocal cords, into the trachea. A bulb is then inflated near the distal tip of the tube to help secure it in place and protect the airway from blood, vomit, and secretions. In some embodiments, cells are administered to a subject having "nasotracheal intubation," which is defined as a tracheal intubation where a tube is passed through the nose, larynx, vocal cords, and trachea.

In some embodiments, an effective amount of lung progenitor cells is administered to a subject by systemic administration, such as intravenous administration.

The phrases "systemic administration," "administered systemically", "peripheral administration" and "administered peripherally" as used herein refer to the administration of a population of lung progenitor cells other than directly into a target site, tissue, or organ, such as the lung, such that it enters, instead, the subject's circulatory system and, thus, is subject to metabolism and other like processes.

In another embodiment, a composition comprising the human lung progenitor cells and a scaffold are "transplanted" into a subject. Such transplantation can replace one or both lobes of the lungs, or a portion thereof.

In some embodiments of the aspects described herein, one or more routes of administration are used in a subject to achieve distinct effects. For example, lung progenitor cells can be administered to a subject by both intratracheal and intraperitoneal administration routes for treating or repairing lung epithelium and for pulmonary vascular repair and regeneration respectively. In such embodiments, different effective amounts of the isolated or enriched lung progenitor cells can be used for each administration route.

Where aerosol administration is to be used, nebulizer devices require formulations suitable for dispensing the particular composition. The choice of formulation will depend upon the specific composition used and the number of lung progenitors to be administered; such formulations can be adjusted by the skilled practitioner. However, as an example, where the composition is lung progenitor cells in a pharmaceutically acceptable carrier, the composition can be a suspension of the cells in an appropriate buffer (e.g., saline buffer) at an effective concentration of cells per mL of solution. The formulation can also include cell nutrients, a simple sugar (e.g., for osmotic pressure regulation) or other components to maintain the viability of the cells.

Typically, each formulation for aerosol delivery via a nebulizer is specific to the type of device employed and can involve the use of an appropriate propellant material, in addition to the usual diluents, adjuvants and/or carriers useful in therapy.

In some embodiments, additional agents to aid in treatment of the subject can be administered before or following treatment with the lung progenitor cells described herein. Such additional agents can be used to prepare the lung tissue for administration of the progenitor cells. Alternatively, the additional agents can be administered after the lung progenitor cells to support the engraftment and growth of the administered cell in the damaged lung. Such additional agents can be formulated for use with a metered-dose inhaler device, which generally comprises a finely divided powder containing a protein or small molecule suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid can also be useful as a surfactant.

Formulations for dispensing from a powder inhaler device can comprise a finely divided dry powder containing proteins or small molecules and can also include a bulking agent, such as lactose, sorbitol, sucrose, or mannitol in amounts which facilitate dispersal of the powder from the device, e.g., 50 to 90% by weight of the formulation. Protein agents should most advantageously be prepared in particulate form with an average particle size of less than 10 µm (or microns), most preferably 0.5 to 5 m, for most effective delivery to the distal lung.

Nasal delivery of protein or other agents in addition to the lung progenitor cells or progeny thereof is also contemplated. Nasal delivery allows the passage of the protein or other agent to the blood stream directly after administering the therapeutic product to the nose, without the necessity for deposition of the product in the lung. Formulations for nasal delivery include those with dextran or cyclodextran.

The efficacy of treatment can be determined by the skilled clinician. However, a treatment is considered "effective treatment," as the term is used herein, if any one or all of the symptoms, or other clinically accepted symptoms or markers of lung disease, lung injury and/or a lung disorder are reduced, e.g., by at least 10% following treatment with a composition comprising human lung progenitor cells as described herein. Methods of measuring these indicators are known to those of skill in the art and/or described herein.

Indicators of lung disease or lung disorder, or lung injury include functional indicators, e.g., measurement of lung capacity and function, and oxygen saturation (e.g., tissue oxygen saturation or systemic arterial oxygen saturation), as well as biochemical indicators.

For idiopathic pulmonary fibrosis, for example, improved symptoms include an increase of at least 10% of predicted forced vital capacity (FVC) relative to values prior to treatment. FVC is the total volume of air expired after a full inspiration. Patients with obstructive lung disease usually have a normal or only slightly decreased vital capacity. Patients with restrictive lung disease have a decreased vital capacity.

Another measure is FEV1 (Forced Expiratory Volume in 1 Second). This is the volume of air expired in the first second during maximal expiratory effort. The FEV1 is reduced in both obstructive and restrictive lung disease. The FEV1 is reduced in obstructive lung disease because of increased airway resistance. It is reduced in restrictive lung disease because of the low vital capacity.

A related measure is FEV1/FVC. This is the percentage of the vital capacity which is expired in the first second of maximal expiration. In healthy patients the FEV1/FVC is usually around 70%. In patients with obstructive lung disease FEV1/FVC decreases and can be as low as 20-30% in severe obstructive airway disease. Restrictive disorders have a near normal FEV1/FVC.

Where necessary or desired, animal models of lung injury or lung disease can be used to gauge the effectiveness of a particular composition as described herein. As one example, the bleomycin-induced lung injury model of acute lung injury (ALI) can be used. Animal models of lung function are useful for monitoring bronchoconstriction, allergic response, late airway hyperresponsiveness in response to inhaled allergens, among other endpoints and can include, for example, head-out plethysmography or body-plethysmography models (see e.g., Hoymann, H G et al., *J Pharmacol Toxicol Methods* (2007) 55(1): 16-26). Exemplary animal models for asthma, including models of allergic asthma (e.g., acute and chronic allergic asthma), are known in the art. See e.g., Nials and Uddin. (2008) *Dis Model Mech* 1:213-220; Zosky and Sly (2007) *Clin Exp Allergy* 37(7): 973-88; and Kumar and Foster. (2002) *Am J Respir Cell Mol Biol* 27(3):267-72. Animal models of pneumonia are reviewed by Mizgerd and Skerrett (2008) *Am J Physiol Lung Cell Mol Physiol* 294:L387-L398. In addition, small animal imaging can be applied to lung pathophysiologies (Brown R H, et al., *Proc Am Thorac Soc* (2008) 5:591-600).

Kits

Another aspect of the technology described herein relates to kits for treating a lung disease or disorder and/or kits for differentiating a human stem or pluripotent cell to a human lung progenitor cell or for isolating and/or sorting human lung progenitor cells from a population of cells or a tissue. Described herein are kit components that can be included in one or more of the kits described herein.

The kit can include a component for the detection of a marker for human lung progenitor cells, ES cells, iPS cells, thyroid lineage cells, neuronal lineage cells etc. In addition, the kit can include one or more antibodies that bind a cell marker, or primers for an RT-PCR or PCR reaction, e.g., a semi-quantitative or quantitative RT-PCR or PCR reaction. Such components can be used to assess the activation of lung cell-specific markers or the loss of ES cell, iPSC, thyroid lineage, or neuronal lineage markers. If the detection reagent is an antibody, it can be supplied in dry preparation, e.g., lyophilized, or in a solution. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

In one embodiment, the kits described herein can include reagents for isolating a human lung progenitor cell, as that term is used herein. For example, a kit as described herein can comprise an antibody or fragment thereof that binds CD47 and/or CD26. Such kits can optionally include one or more agents that permit the detection of additional lung progenitor cell marker or a lung cell marker or set thereof. The kit can also comprise one or more reagents that permit the detection (or lack thereof) of differentiated lung cells and/or cells of other lineages.

It is envisioned that the methods provided herein can be translated to a clinical setting for the practice of personalized medicine by administering autologous cells differentiated along the lung lineage as described herein to a subject in need thereof. The methods described herein are particularly advantageous in that they can standardize differentiation of iPSCs along the lung lineage, making it directly applicable to any subject in a clinical setting. Thus, in some embodiments, the kits described herein can include standardized amounts of differentiation agents (e.g., CHIR99021, rhFGF, rhKGF, Y-27632, etc.) and an antibody or fragment thereof that binds CD47 and/or CD26 to permit the standardized isolation of "primordial" lung progenitor cells.

In addition, the kit optionally comprises informational material. The informational material can be descriptive, instructional, marketing or other material that relates to the methods described herein and/or the use of a compound(s) described herein for the methods described herein. The informational material of the kits is not limited in its form. In one embodiment, the informational material can include information about the amount of antibody to use in different applications (e.g., IHC, FACS), and so forth. In one embodiment, the informational material relates to methods for using or administering the compound.

In one embodiment, the informational material can include instructions to prepare, sort and administer a human lung progenitor cell as described herein in a suitable manner to effect treatment of a lung injury or a lung disease or disorder., e.g., in a suitable dose, dosage form, or mode of administration (e.g., a dose, dosage form, or mode of administration described herein).

In addition to antibody binding reagents as described herein, the composition of the kit can include other ingredients, such as a solvent or buffer, a stabilizer, a preservative, and/or an additional agent, e.g., for differentiating stem cells (e.g., in vitro), isolating or sorting human lung progenitor cells or for treating a condition or disorder described herein.

The kit will typically be provided with its various elements included in one package, e.g., a fiber-based, e.g., a cardboard, or polymeric, e.g., a Styrofoam box. The enclosure can be configured so as to maintain a temperature differential between the interior and the exterior, e.g., it can provide insulating properties to keep the reagents at a preselected temperature for a preselected time.

EXAMPLES

It has been postulated that during human fetal development all cells of the lung epithelium derive from embryonic endodermal NKX2-1+ precursors, however, this hypothesis has not been formally tested due to an inability to purify or track these progenitors for detailed characterization. Provided herein are methods to engineer and developmentally differentiate NKX2-1GFP reporter pluripotent stem cells (PSCs) in vitro to generate and isolate human primordial lung progenitors that express NKX2-1 but are initially devoid of markers of differentiated lung lineages. After sorting to purity, primordial lung progenitors retain proliferative capacity and exhibit lung epithelial maturation. In the absence of mesenchymal co-culture support, these primordial progenitors can generate epithelial-only spheroids in defined 3D cultures, or can recapitulate epithelial-mesenchymal developing lung interactions when recombined with fetal mouse lung mesenchyme. As these progenitors move through the earliest moments of lung lineage specification from definitive endoderm they can be imaged in real time or isolated for time-series global transcriptomic profiling and single cell RNA sequencing. These profiles indicate that evolutionarily conserved, stage-dependent gene signatures of early lung development are expressed in primordial human lung progenitors and reveal a cell surface phenotype, $CD47^{hi}/CD26^{lo}$, that allows their prospective isolation from untargeted patient-specific PSCs for further in vitro lung directed differentiation in 3D culture and future applications in regenerative medicine.

Example 1: Prospective Isolation and Single Cell Profiling of NKX2-1+/CD47+ Human Lung Progenitors Derived from Pluripotent Stem Cells Little is known about the early stages of human lung development, preventing an understanding of whether successful healing from adult lung injury involves recapitulation of embryonic mechanisms and limiting approaches for generating lung progenitors from pluripotent cells in vitro. Inbred mouse models have begun to define the mechanisms regulating lung specification and patterning but how this breadth of work applies to human lung development is unknown. Current claims suggest that all cells of the postnatal mammalian lung epithelium derive from embryonic NKX2-1+ progenitors, however scant literature exists formally testing this hypothesis either in mice or humans. Support for this paradigm derives mainly from the observation that Nkx2-1 is the first gene locus known to be activated in cells of the endodermal lung primordium (1, 2). In addition, Nkx2-1-null mutant mice have hypoplastic lungs that fail to mature (3) and human children with NKX2-1 mutations develop respiratory insufficiency, hypothyroidism and neurological impairment, but these observations do not necessarily indicate that all lung epithelial cells derive from NKX2-1+ progenitor intermediates. Since lung lineage specification is thought to occur in relatively few endodermal cells during a narrow developmental time period in vivo it has been difficult to gain access to these cells in human embryos or to follow their cell fate decisions in real time. Hence it was sought to interrogate the earliest moments of human lung lineage specification by engineering an in vitro system that would allow the isolation and differentiation of pure populations of NKX2-1+ putative human lung progenitors. Given the known capacity of mouse PSCs to form all cell types, including lung lineages, after transfer into mouse blastocyst embryos and the known broad differentiation repertoire of human PSCs in vitro, this system was based on the in vitro differentiation of PSCs.

Initial published attempts at deriving lung epithelium from PSCs relied on the presence of drug-resistance genes or used incompletely defined media (4-6) resulting in inefficient induction of selected lung markers. Subsequently a number of groups have had more success by broadly attempting to recapitulate the key milestones of embryonic lung development in vitro through the exogenous addition of sequential combinations of growth factors (7-11). By differentiating iPSCs into definitive endoderm, patterning this endoderm via inhibition of TGFβ and BMP signaling, and then adding various combinations of Wnts, FGFs, BMPs, and retinoic acid these groups demonstrated the in vitro derivation of cultures expressing a broad array of lung epithelial markers. However, the characterization of the cells derived at different stages of these protocols was restricted to a selection of predominantly non-specific markers and suggested heterogeneous cell types were present (12, 13). The most recently published directed differentiation protocols describe variable efficiencies of induction of NKX2-1+ cells from ESCs or iPSCs ranging from approximately 36 to 86% (9, 10, 14). Such heterogeneity limits the utility of these cultures for downstream applications and has caused uncertainty as to whether subsequent lung lineages derive directly from these early endodermal NKX2-1+ precursors. To derive more mature lung cell types from iPSCs, some groups have employed prolonged in vitro cultures, murine kidney capsule or subcutaneous transplantations, or co-culture with lung mesenchyme (9-11, 14-16). These results indicate that at some point during differentiation of iPSCs progenitors, cells with competence to form mature lung cells likely emerge. However, it has not previously been possible to isolate these cells for characterization or to properly test their differentiation repertoire.

To perform a detailed profiling of candidate human lung progenitors the NKX2-1 human locus was targeted with a fluorescent reporter, enabling isolation of the earliest identifiable putative lung-lineage committed cells derived from PSCs. In addition, this same reporter iPSC line facilitates the derivation and purification of alternate developing human progenitors that express NKX2-1, such as endodermal thyroid and ectodermal forebrain-like lineages. After directed differentiation of these PSCs in defined media designed to promote lung rather than thyroid or forebrain development, it was demonstrated that the NKX2-1+ endodermal population is highly enriched in undifferentiated (primordial) progenitors competent to express a broad repertoire of lung epithelial marker genes, supporting the paradigm that the human lung epithelium derives from embryonic NKX2-1+ progenitors. Provided herein are population-based as well as single-cell global transcriptomic profiles that define developmental stage-specific gene signatures of iPSC-derived lung progenitors. These signatures indicate that an evolutionarily conserved lung developmental program exists in both mice and humans.

Furthermore, these signatures reveal that NKX2-1+ human lung progenitors can be prospectively isolated from patient-specific iPSCs based on the cell surface phenotype $CD47^{hi}/CD26^{lo}$ Ultimately, the detailed characterization and purification of human lung progenitors presented here provide access to a nearly inexhaustible supply of these cells for disease modeling, cell-based therapies, and basic developmental studies.

Results

Figure 8A:
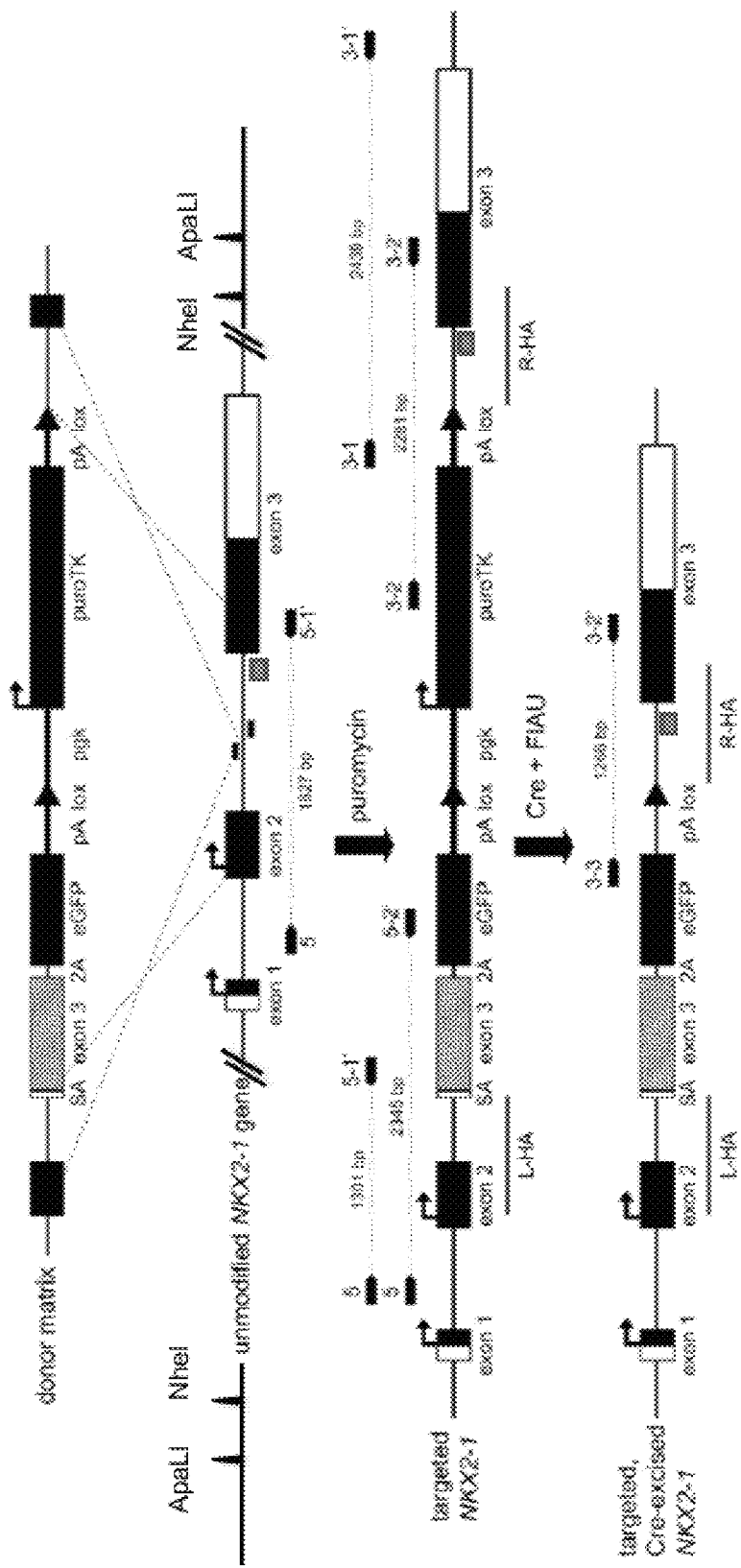
FIG. 8A-FIG. 8H Gene editing of the human NKX2-1 locus to engineer NKX2-1$^{GFP}$ reporter iPSC lines.
Figure 8B:
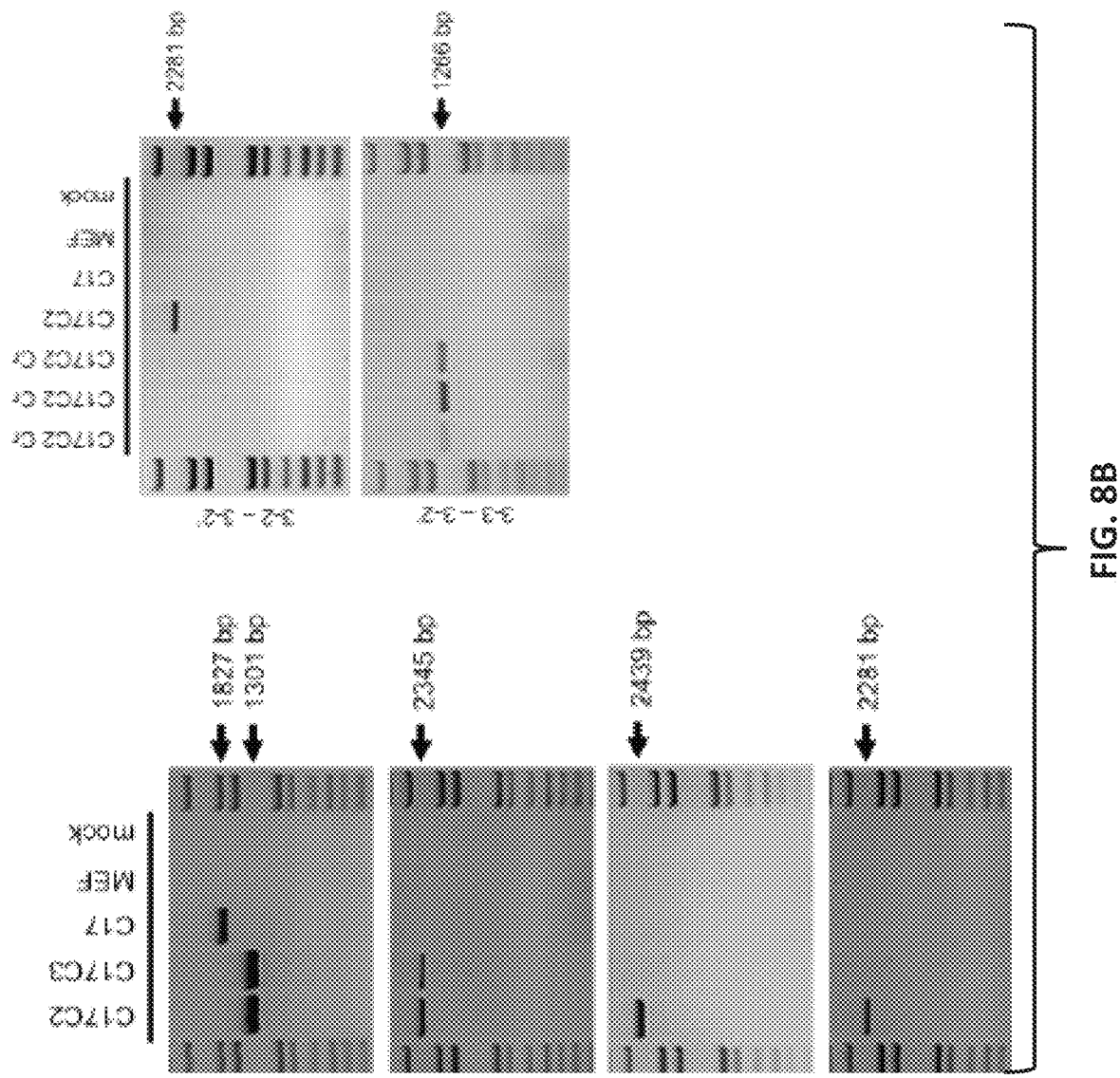
Figure 8C:
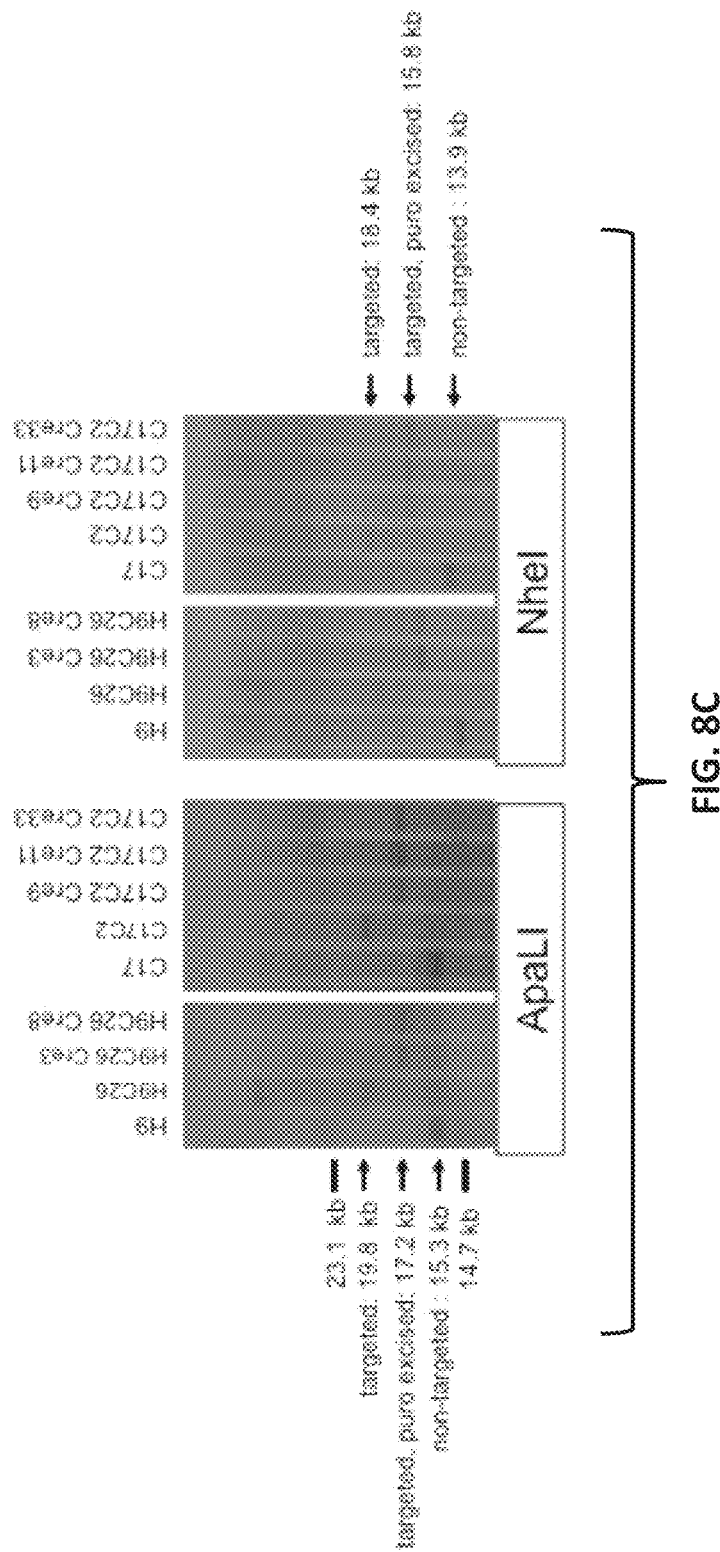

An NKX2-1GFP Reporter Enables Purification of Human Lung, Thyroid, and Forebrain Lineages In order to generate a tool for the identification and purification of candidate human lung progenitors, gene editing technologies were used to target an enhanced green fluorescence reporter gene (GFP) to the endogenous human NKX2-1 locus in multiple human PSC lines. Prior reports of targeting GFP to the NKX2-1 locus in human PSCs for the derivation of forebrain lineages resulted in NKX2-1 haploinsufficiency (17). Hence, pursuing a strategy designed to retain intact expression of targeted loci without haploinsufficiency (FIGS. 1A, 8A), the inventors targeted an exon3-2A-GFP cassette to the second intron of NKX2-1 using either TALENs or CRISPR-Cas9 tools deployed in ESCs (H9) or in previously published iPSC lines: cystic fibrosis patient-specific C17 iPSCs (C17; FIGS. 1 and 8)(17) and normal BU3 iPSCs (18). The resulting NKX2-1$^{GFP}$ reporter PSC clones (hereafter H9NKX2-1$^{GFP}$ BU3NKX2-1$^{GFP}$, and C17NKX2-1$^{GFP}$) demonstrated successful mono and bi-allelic integration of the donor template by PCR (FIG. 8B). For further profiling, one homozygous targeted clone was selected for each of the TALENs-targeted lines (H9 and C17) as well as one homozygous CRISPR-Cas9 targeted BU3 clone (FIGS. 8B and 8C).

Figure 1B:
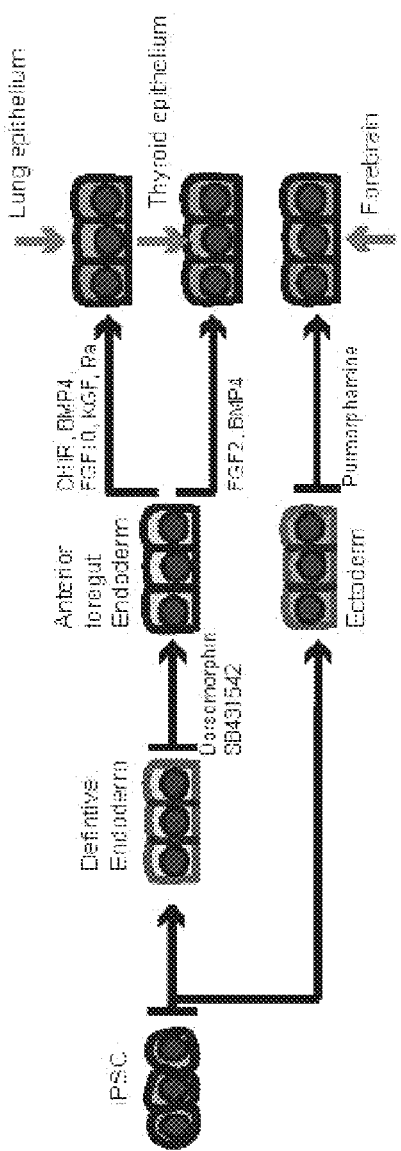
Figure 1C:
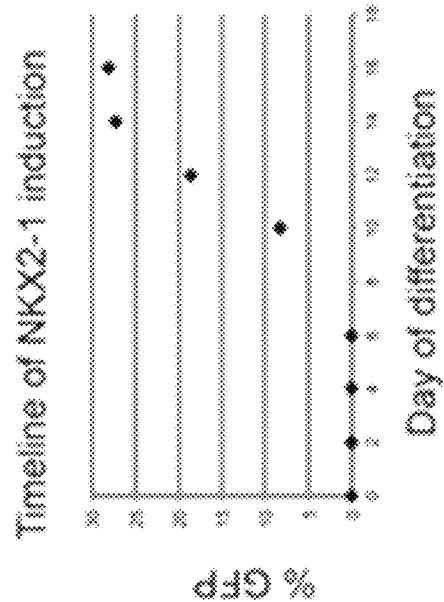
Figure 1D:
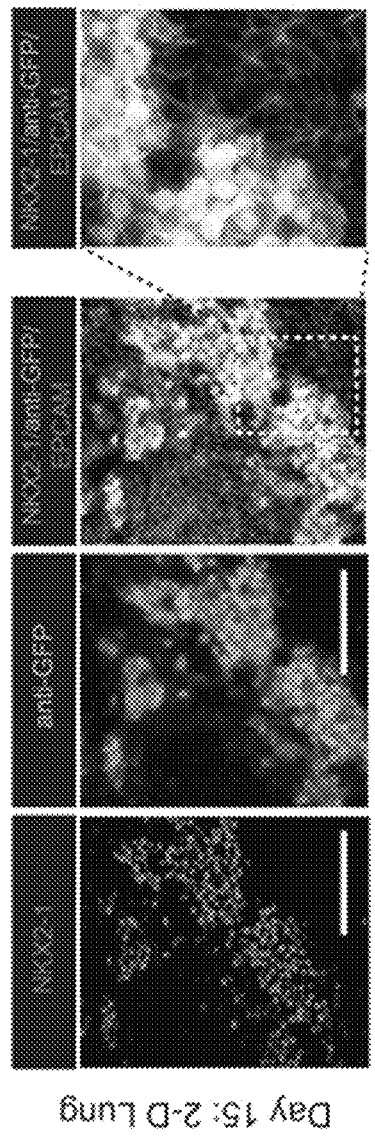
Figure 1E:
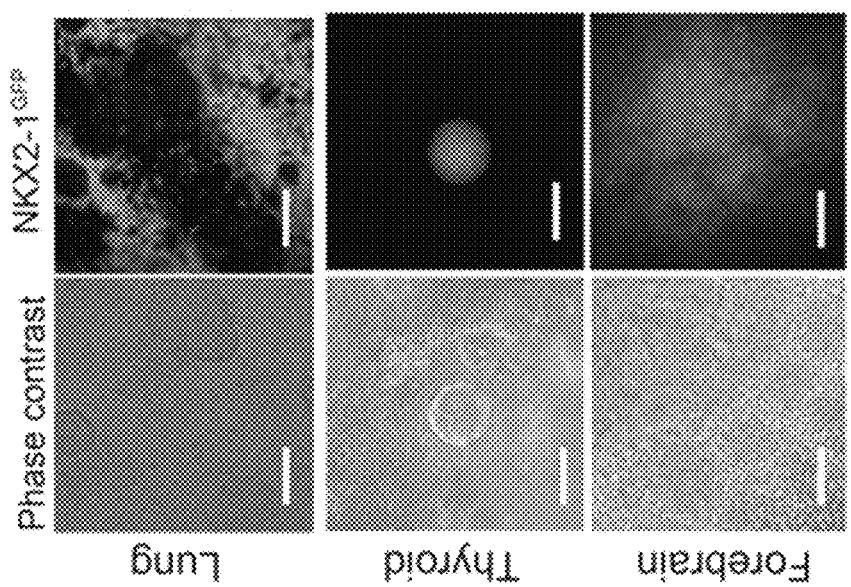
Figure 8E:
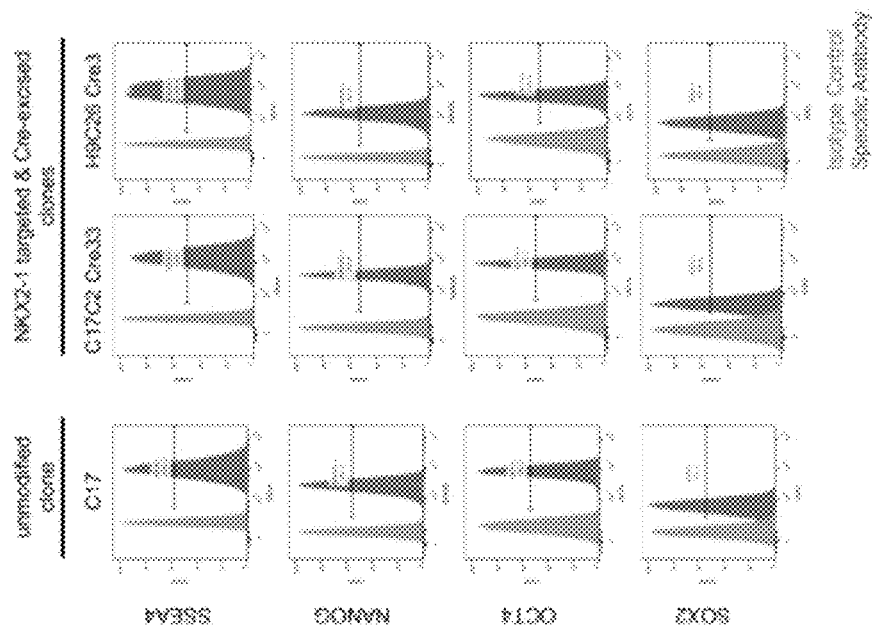
Figure 8D:
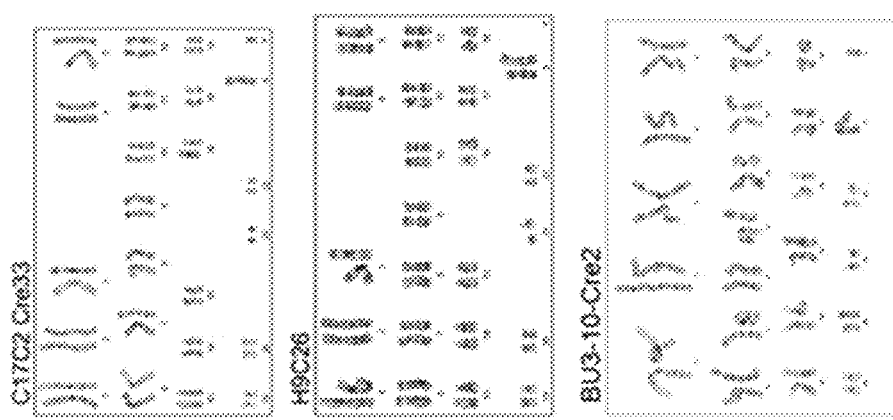
Figure 8G:
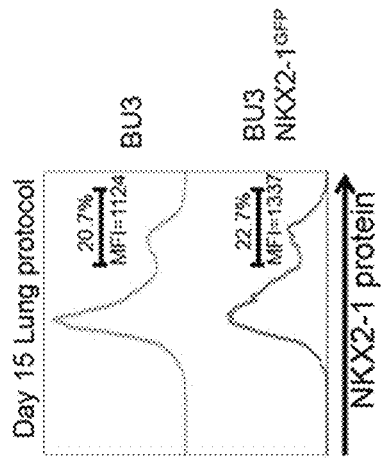
Figure 8H:
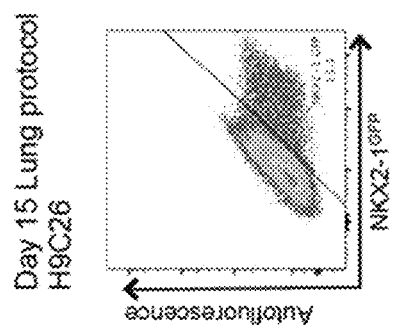
Figure 8F:
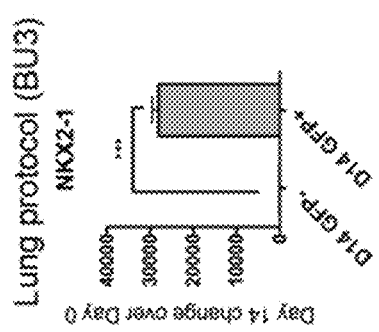
Figure 9A:
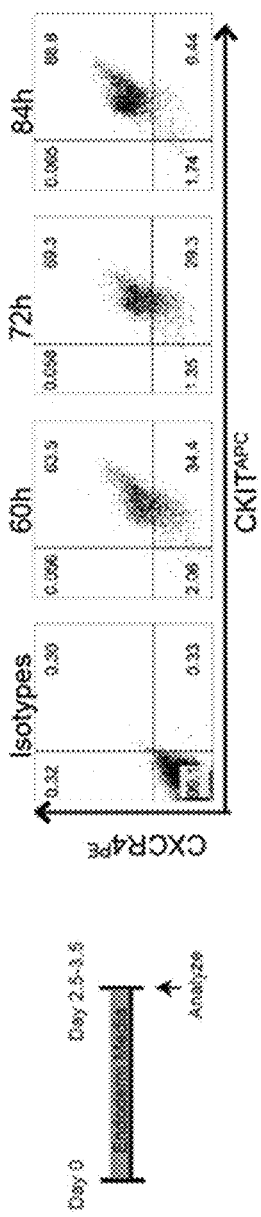
Figure 9B:
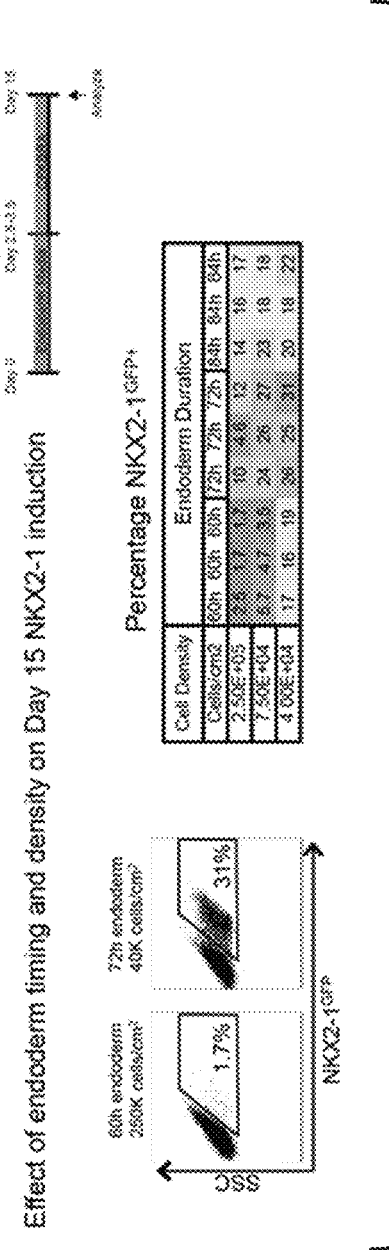
Figure 9E:
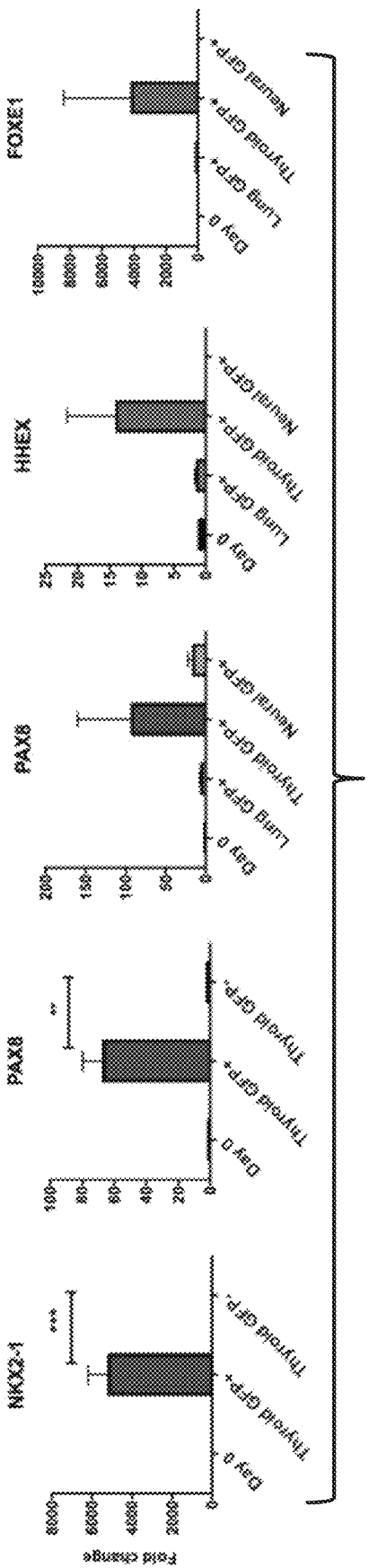

To differentiate each targeted PSC line, several different protocols were tested for in vitro directed differentiation of human PSCs into the three lineages known to express NKX2-1: neural/forebrain (19, 20), lung (7-9) or thyroid (18) (FIG. 1B). Protocols for lung and thyroid both required generating anterior foregut-like endoderm followed by the addition of Chir99021(Chir), BMP4, KGF, FGF10 and retinoic acid for lung vs. BMP4 and FGF2 for thyroid. Consistent with prior publications (9) the percentage of NKX2-1+ cells on day 15 of the lung directed differentiation was typically 41±21% (mean±SD) when using the ESC line "RUES2" (data not shown). However, when other cells lines including H9 and C17 were differentiated the percentage of NKX2-1 expressing cells was typically less than 1% (data not shown). Thus a methodology was developed for the optimization of lung differentiation for each cell line by altering the duration of endoderm induction, the cell density of replated endoderm, and the duration of TGF-β/BMP inhibition in order to augment the percentage of NKX2-1+ cells emerging by day 15 (FIGS. 8H, 9A-9B). In contrast to prior published experience for some PSC lines (9), it was found that the inhibition of Wnt signaling for 24 hours during the TGF-β/BMP inhibition stage did not consistently increase the efficiency of NKX2-1 induction. Employing the new lung differentiation protocol optimized for each clone, GFP expression was first detected between day 8 and 10 of differentiation and the percentage of GFP+ cells peaked between day 12-16 with an efficiency of ~25.6±9.5% for C17NKX2-1$^{GFP}$ (FIGS. 1C and 1F) and 25.6±4.4%% for BU3NX2-1$^{GFP}$(data not shown). Day 15 of differentiation was selected for further characterization of GFP+ cells in the lung protocol. Immunostaining for cytoplasmic GFP and nuclear NKX2-1 protein indicated faithful and specific expression of the GFP reporter in NKX2-1+ cells (FIG. 1D). It was confirmed that NKX2-1 protein levels were not significantly perturbed by the targeting strategy used in this study by comparing homozygously targeted BU3 NKX2-1$^{GFP}$ iPSCs to non-targeted parental control iPSCs (FIG. 8G).

Figure 1G:
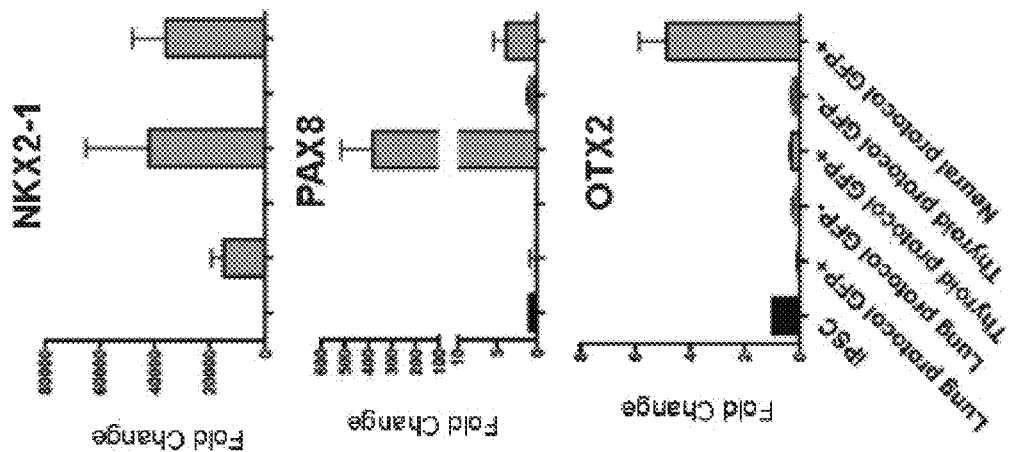
Figure 1F:
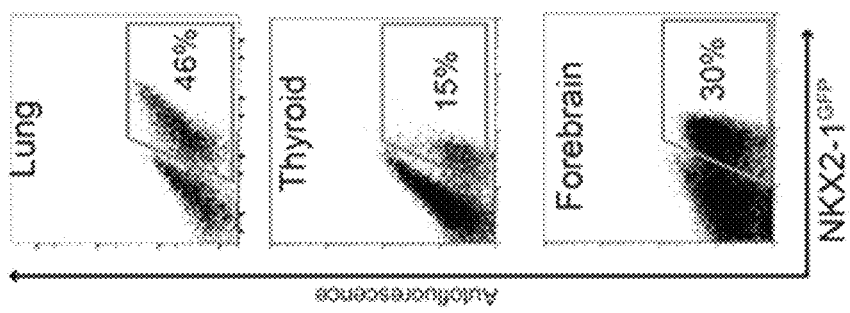

Sorting GFP+ cells from each of the three differentiation protocols enriched for cells expressing NKX2-1 mRNA (FIGS. 1F & 1G). GFP+ cells from thyroid and forebrain protocols were selectively enriched in expression of early lineage markers: PAX8, HHEX and FOXE1 for thyroid and OTX2, OTX1, SOX1, PAX6 and SIX3 for forebrain (FIG. 1G, 9C-9E and data not shown). The NKX2-1$^{GFP+}$ cells isolated on day 15 in the lung protocol were NKX2-1+/PAX8- (FIG. 9E) and importantly lacked detectable expression of markers of lung epithelial differentiation (e.g., SFTPC or SCGB1A1; data not shown) indicating that they may have undergone lung lineage specification but were still undifferentiated or "primordial." Lung-specific progenitor markers or transcriptomic signatures are not known at this primordial developmental stage. Hence, to test the hypothesis that day 15 NKX2-1$^{GFP+}$ cells represented lung epithelial progenitors their competence to express markers of more differentiated lung epithelium was investigated.

Figure 2A:
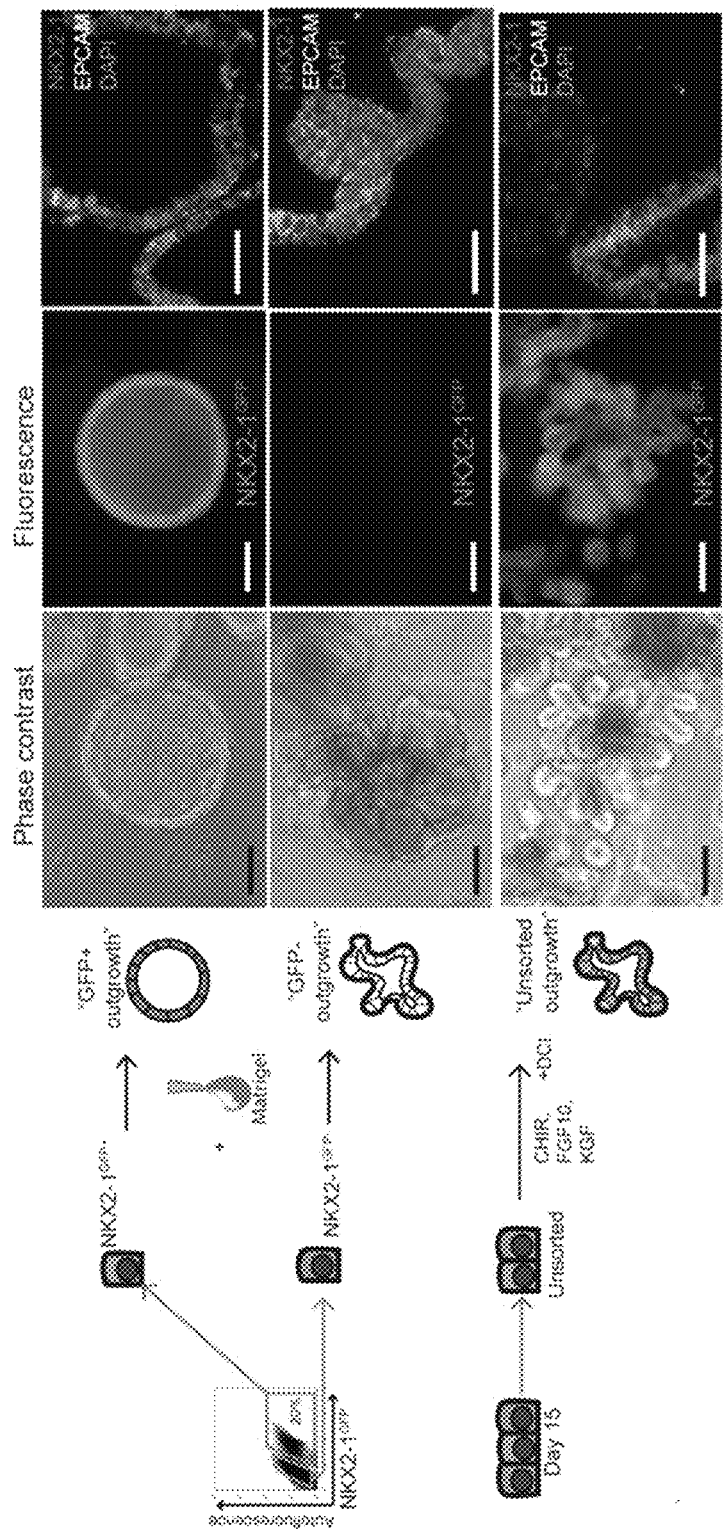
FIG. 2A-FIG. 2D Purified iPSC-derived NKX2-1$^{GFP+}$ cells exhibit lung progenitor potential and ability to form epithelial spheroids in 3D culture.
Figure 2B:
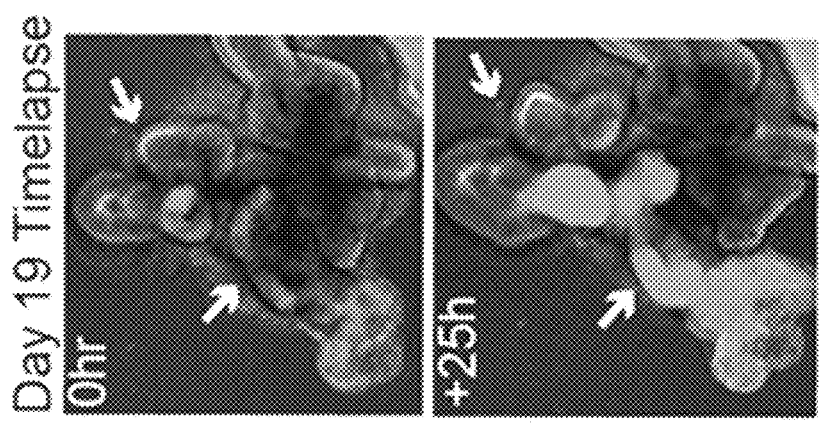

Purified IPSC-Derived NKx2-1$^{GFP+}$ Cells Exhibit Lung Progenitor Potential Employing the human lung directed differentiation protocol described herein and the C17NKX2-1$^{GFP+}$ iPSC line it was tested whether differentiated lung epithelial cells derive directly from NKX2-1+ progenitors. NKX2-1$^{GFP+}$ vs. NKX2-1$^{GFP-}$ cells were sorted on day 15 and each population was plated (vs. unsorted controls) in 3D MATRIGEL™ in serum-free media supplemented with factors that have been previously shown to support lung epithelial differentiation (8,9): Chir, KGF and FGF10 for seven days followed by the addition of dexamethasone, cAMP and IBMX until day 36 (FIG. 2A) (8, 9). The outgrowth of proliferating cell aggregates was observed over the next 2-3 weeks (hereafter "organoids") (FIG. 2A). Unsorted day 15 cells plated as clumps gave rise to lobular organoids with GFP+ and GFP- areas on day 36 (FIG. 2A) and GFP+ cells were followed in real-time in these unsorted cultures by time-lapse photography (FIG. 2B and data not shown). In contrast, when unsorted cells were plated as single cell suspensions simpler spherical organoids formed (data not shown).

Figure 2C:
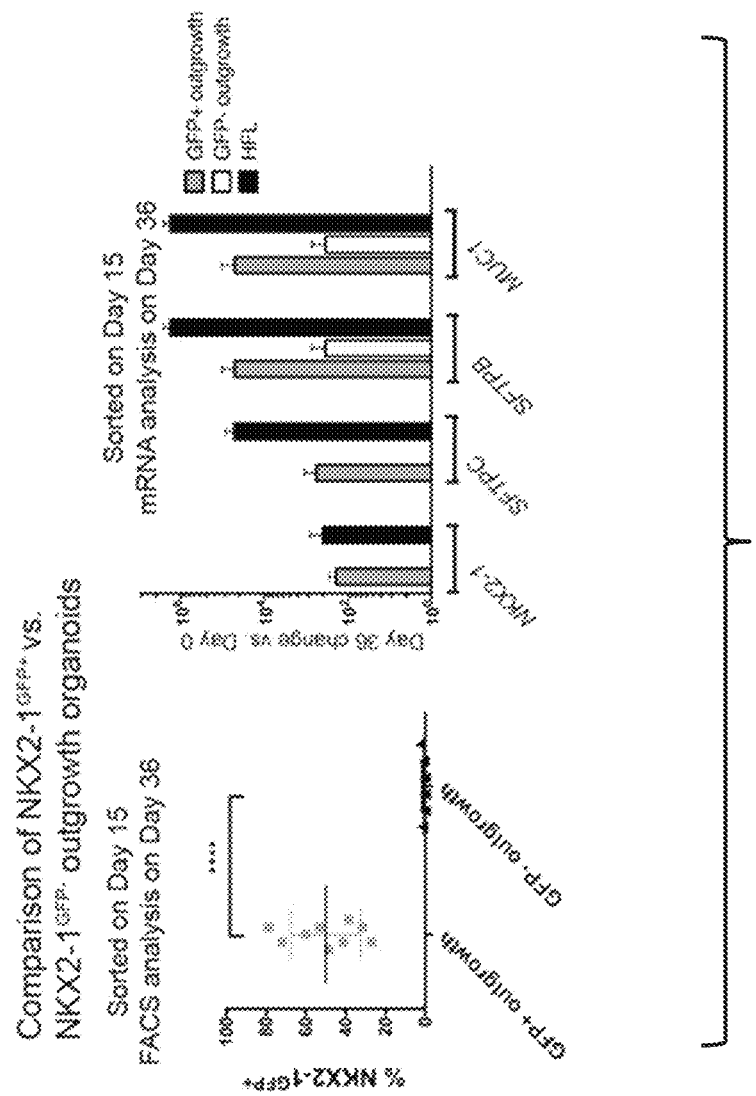
Figure 2D:
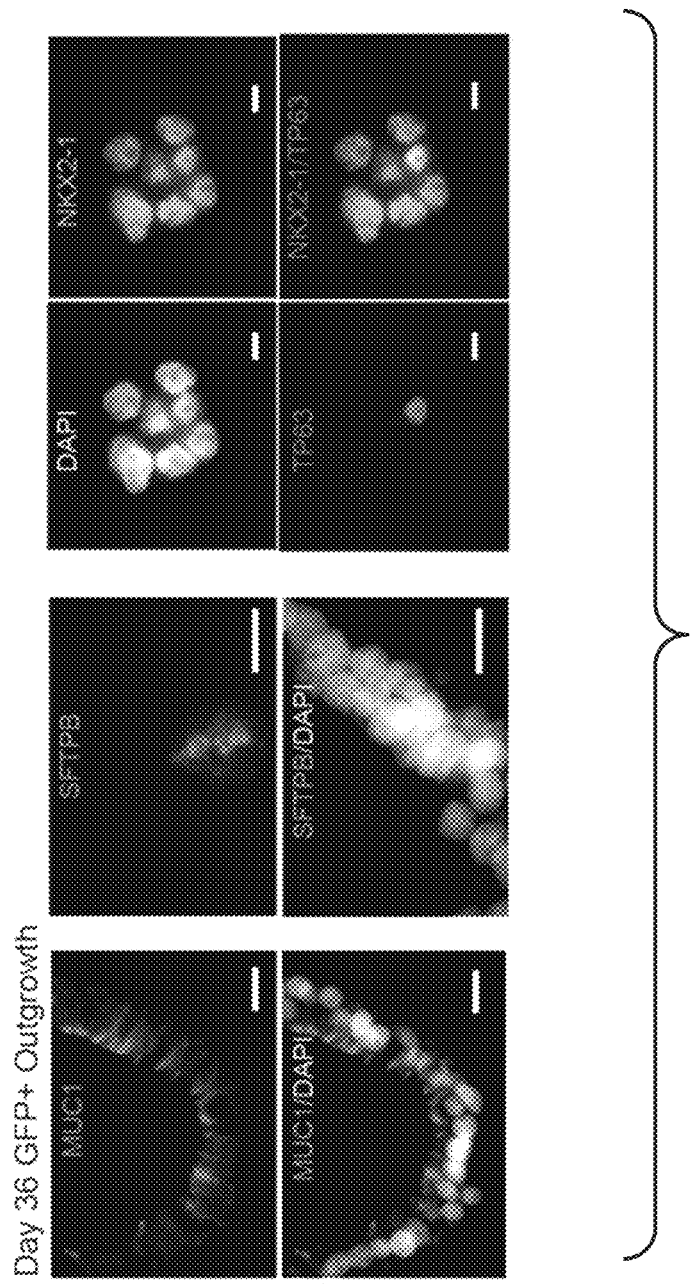
Figure 10A:
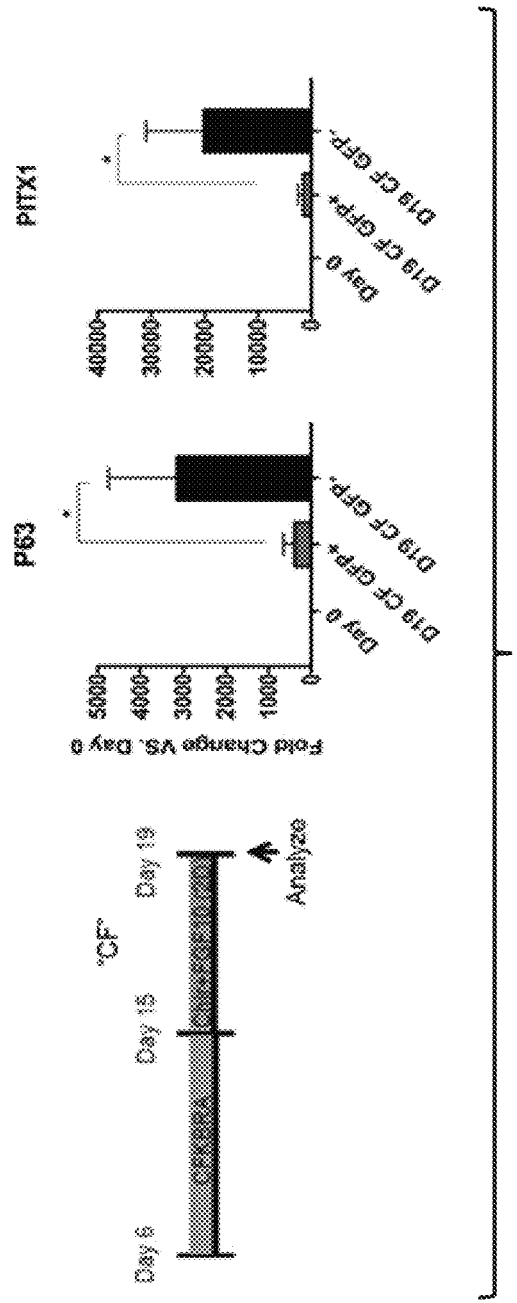
FIG. 10A-FIG. 10E Further characterization of iPSC-derived cells on days 15-19 of differentiation and after recombination with E12 mouse lung mesenchyme.
Figure 10B:
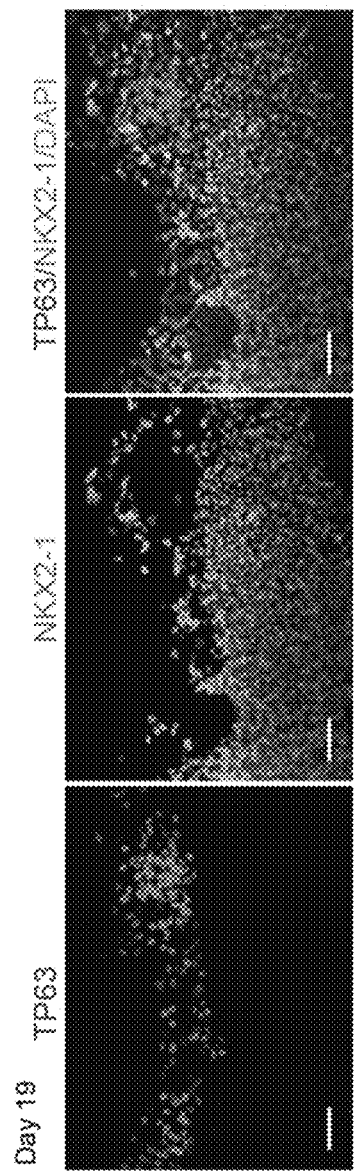
Figure 10C:
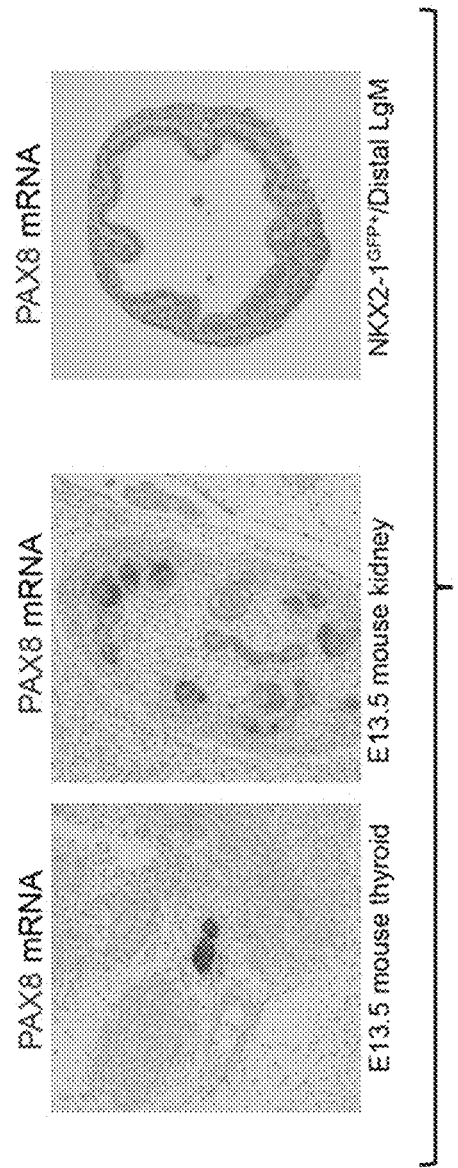
Figure 10E:
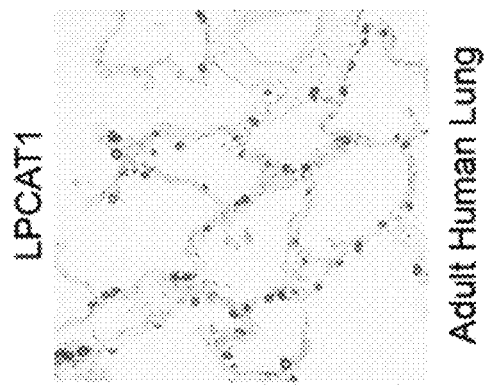

Immunostaining of these unsorted organoids demonstrated areas of monolayered NKX2-1+/EPCAM+ epithelium surrounding an inner lumen but also areas and organoids that were NKX2-1-(FIG. 2A). GFP+ cells could be followed in real-time in the unsorted cultures by time-lapse photography (FIG. 2B and data not shown). Sorted day 15 GFP+ cells gave rise to GFP+ aggregates in 3D culture, with 50.1±17.6% (mean±/-S.D; n=6 runs) of the progeny remaining GFP+ by flow cytometry on day 36 ("GFP+ outgrowth") (FIG. 2C). Sorted day 15 GFP-cells remained GFP- on day 36 (99.8±0.2%) ("GFP- outgrowth") (FIG. 2C). The GFP+ outgrowth formed predominantly NKX2-1+/EPCAM+ spheroids whereas GFP- outgrowth formed EPCAM+ and EPCAM- organoids that were uniformly NKX2-1- (FIG. 2A). The sorted NKX2-1$^{GFP+}$ progenitors on day 15 comprised the entirety of cells competent to subsequently express the lung-specific marker SFTPC by day 36 (FIG. 2C and data not shown), indicating this population contained lung progenitors. The GFP+ outgrowth was also highly enriched for cells competent to express lung markers SFTPB and MUC1, although these markers are known to have less lung specificity than SFTPC (FIG. 2C). Immunostaining confirmed discrete populations of cells expressing SFTPB and MUC1 proteins in the GFP+ outgrowth (FIG. 2D). In contract TP63+ cells were present in both GFP+ and GFP- outgrowths but were more prevalent in GFP- outgrowths, indicating TP63 is not a lung-specific marker in this system. Consistent with this interpretation, TP63+ cells in the GFP+ outgrowth co-expressed NKX2-1, whereas TP63+ cells in the GFP- outgrowth did not express NKX2-1 (FIGS. 2D, 10A). RT-qPCR confirmed significantly higher levels of TP63 and the esophageal marker, PITX1, in the GFP– outgrowth, indicating that NKX2-1/TP63+ cells may represent alternative foregut derivatives, such as developing esophageal epithelium (FIG. 10B).

Figure 3A:
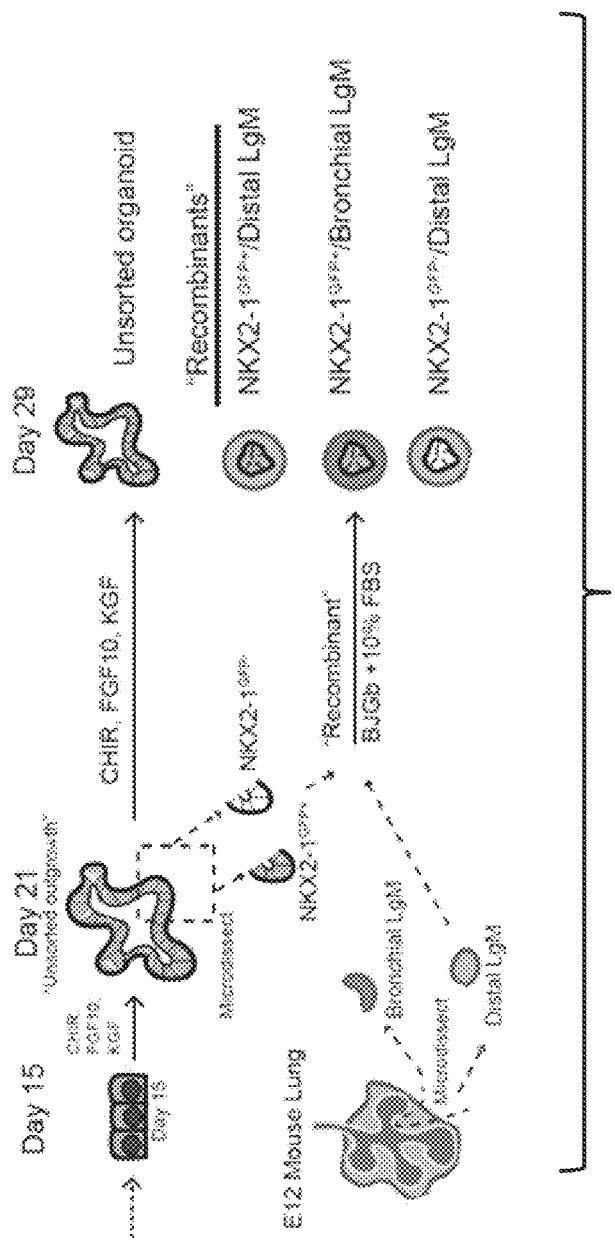
FIG. 3A-FIG. 3F Mouse-human "recombinant" cultures demonstrate fetal mouse lung mesenchyme augments distal lung differentiation in iPSC-derived human lung organoids.
Figure 3B:
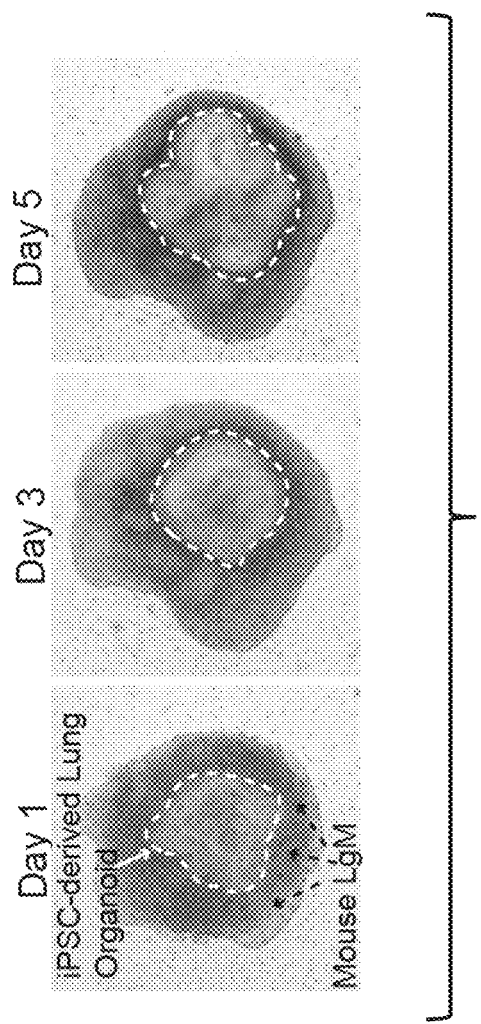

Fetal Lung Mesenchyme Augments Distal Lung Differentiation in iPSC-Derived Lung Organoids Having established that NKX2-1+ primordial progenitors can be induced to upregulate markers of lung epithelial lineages without mesenchymal co-culture support, it was next sought to determine whether these progenitors might also respond to developmental cues provided by primary embryonic lung mesenchyme. Lung epithelial-mesenchymal interactions are essential for lung epithelial growth, branching and differentiation (21-23). For example, separating and recombining rat embryonic lung epithelium and mesenchyme ("recombinants") has previously revealed both the importance of lung mesenchyme and the stage-specific plasticity of the developing lung epithelium in response to mesenchymal signals (21). Hence, it was asked whether iPSC-derived NKX2-1+ cells are competent to respond to developing mouse lung mesenchyme and if distal lung epithelial gene expression might be induced by distal lung mesenchyme compared with bronchial mesenchyme or standard directed differentiation conditions without mesenchyme (FIG. 3A). Lung organoids generated from day 15 human iPSCs were cultured in 3D conditions until day 21. Either NKX2-1$^{GFP+}$ or NKX2-1$^{GFP-}$ areas were microdissected and recombined with E12 mouse lung distal or bronchial mesenchyme (FIG. 3A).

Figure 3C:
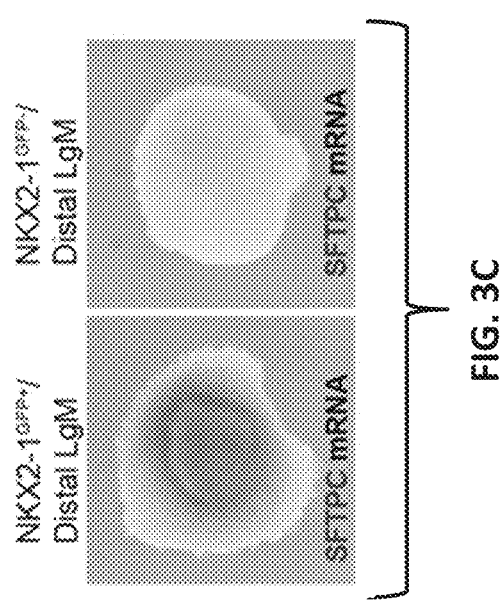
Figure 3D:
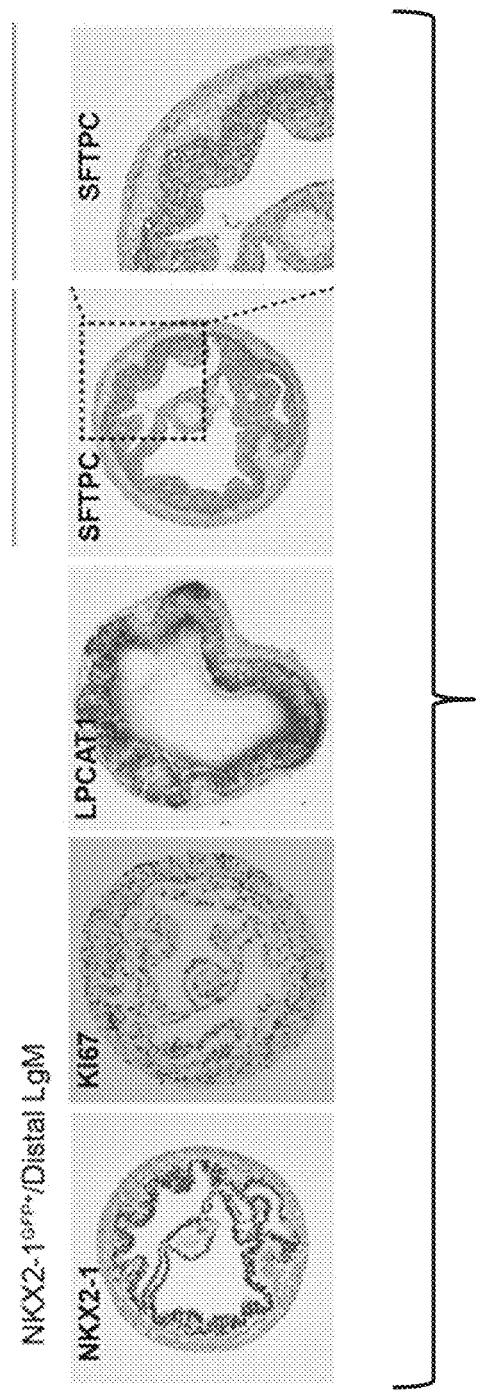
Figure 10D:
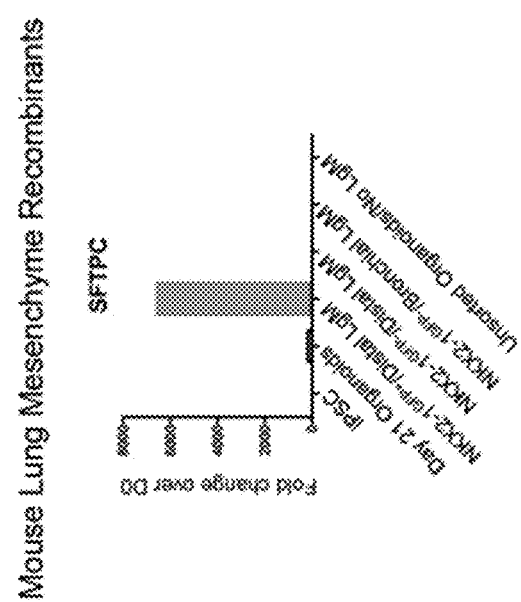

After 5-7 further days in culture as recombinants, continued growth of the human GFP+ aggregates in response to mouse distal lung mesenchyme, continued robust expression of nuclear human NKX2-1 protein, expression of proliferation marker Ki67, and no detectable expression of thyroid markers was observed (FIGS. 3B-3D and 10C). Importantly, induction of cytoplasmic human pro-SFTPC and LPCAT1 protein expression was noted in the majority of the human iPSC-derived cells by immunostaining, with validation of human SFTPC mRNA expression by both in situ hybridization as well as RT-qPCR (FIGS. 3B-3D and 10D-10E). Levels of SFTPC induction were higher in organoids recombined with distal lung mesenchyme than in those continued solely through directed differentiation without recombination (FIG. 3D). Since E12 mouse lung mesenchyme presumably lacks the signals needed for full maturation of the alveolar epithelium, which normally begins in mouse at E18.5, human cells in these recombinants did not exhibit robust induction of transcripts associated with mature lamellar body biogenesis, such as LAMP3 (data not shown), and did not appreciably display lamellar body-shaped inclusions by microscopy, as expected. Bronchial mesenchyme did not induce SFTPC expression or proximal lung epithelial markers (SOX2, TP63 or SCGB3A1) in NKX2-1GFP+ cells (FIG. 10D and data not shown). In addition, control recombinants generated using GFP negative organoids were not competent to induce either human NKX2-1 or SFTPC expression (FIGS. 3C and 10D).

These results indicate that human iPSC-derived NKX2-1+ lung progenitors respond to developing lung mesenchymal cues, findings in keeping with prior observations that recombining rat distal lung mesenchyme with isolated early proximal or distal primary lung epithelium induces distal alveolar marker gene expression (25).

Figure 3F:
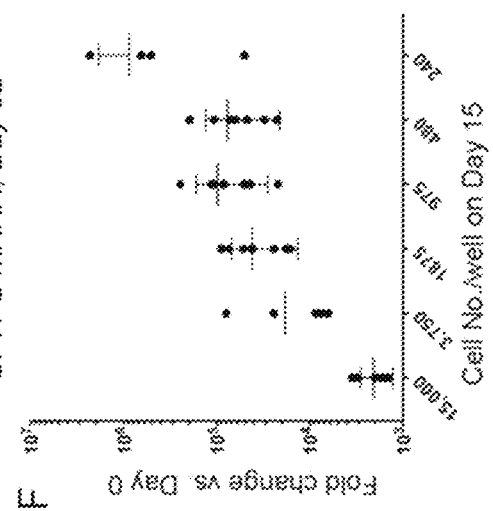
Figure 3E:
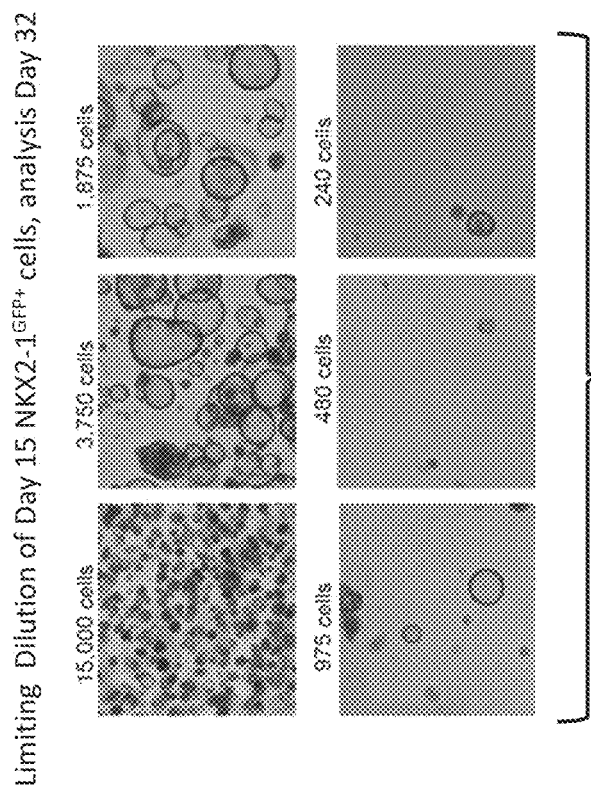

The expression of SFTPC in response to lung mesenchyme in the majority of epithelial cells analyzed raised the question of whether SFTPC+ cells were being derived by the selective outgrowth of rare distal lung-competent day 15 precursors vs. the possibility that distal lung-competent progenitors might be common within the NKX2-1+ day 15 population. To distinguish these possibilities day 15 NKX2-1GFP+ cells were purified and replated in increasingly dilute numbers of cells (15,000 cells down to 240 cells per well of a 96 well plate) for further directed differentiation from day 15 to day 32 in 3D cultures without mesenchymal co-culture support. This limiting dilution assay should result in declining SFTPC competence with dilution if only rare distal progenitors are present within the day 15 NKX2-1+ population (FIGS. 3E, 3F). On day 32 it was observed that lower cell numbers, plated at limiting dilution, resulted in stable to increased SFTPC mRNA expression consistent with the existence of common rather than rare distal lung-competent progenitors within the NKX2-1+ day 15 population and indicating inhibition of distal differentiation in increasingly dense replating conditions in epithelial-only sphere outgrowths.

Figure 4A:
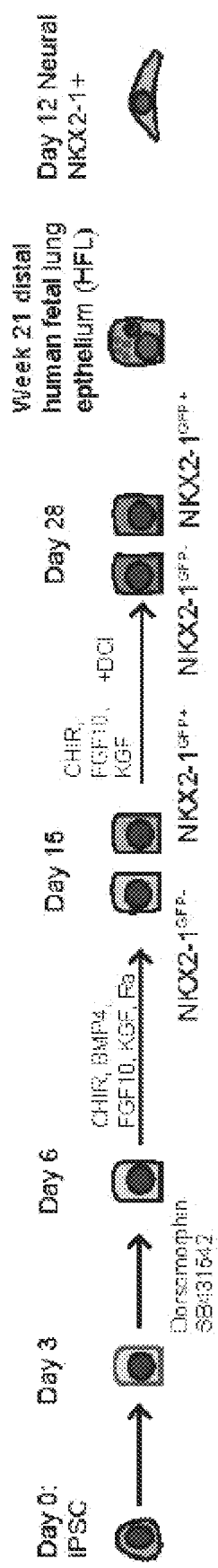
FIG. 4A-FIG. 4F Time series global transcriptomic profiling of human iPSCs undergoing lung directed differentiation.

Global Gene Expression Kinetics of Early Human Lung Development Modeled by Directed Differentiation of Human PSCs It was next sought to define the fundamental programs of early human NKX2-1+ lung progenitors and their global gene expression kinetics during the course of in vitro directed differentiation. Time series microarray expression profiles were prepared representing the following 5 key stages of iPSC lung-directed differentiation (FIG. 4A): undifferentiated iPSC (day 0), definitive endoderm (day 3), anterior foregut-like endoderm (day 6), sorted NKX2-1$^{GFP+}$ and NKX2-1$^{GFP-}$ primordial progenitors (day 15), sorted NKX2-1$^{GFP+}$ and NKX2-1$^{GFP-}$ differentiated cells (day 28). For positive and negative controls primary distal fetal lung epithelial cells (21 weeks of human gestation) and forebrain-like iPSC-derived neural NKX2-1$^{GFP+}$ cells (as shown in FIG. 1B) included, respectively (data not shown; Gene Expression Omnibus, GEO Series ID GSE83310).

Figure 4C:
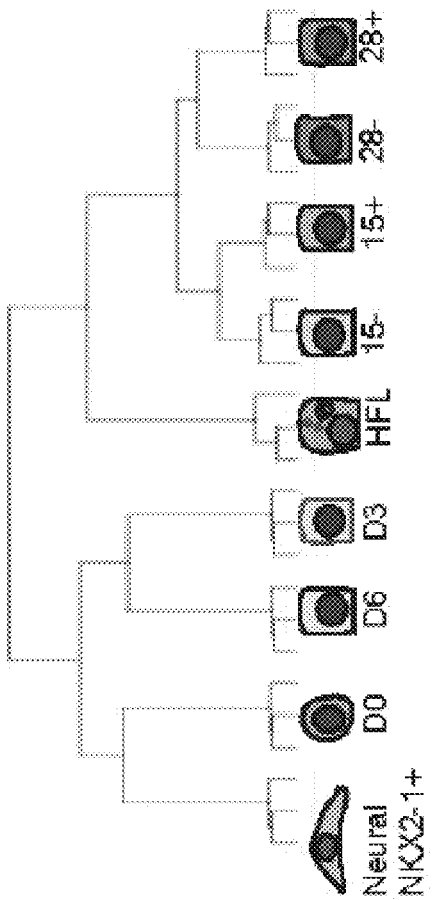
Figure 4B:
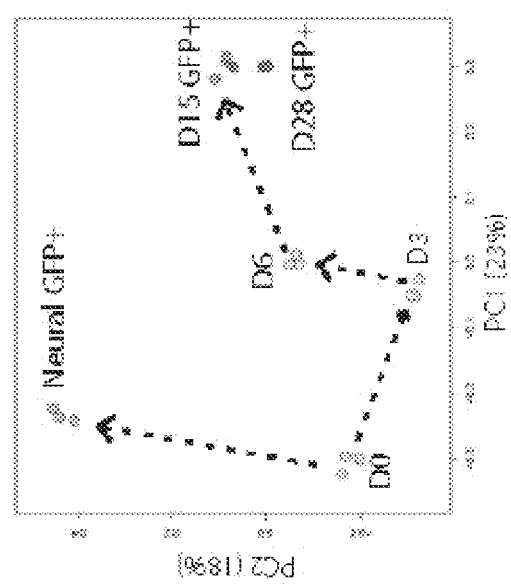
Figures 4D, 4E:
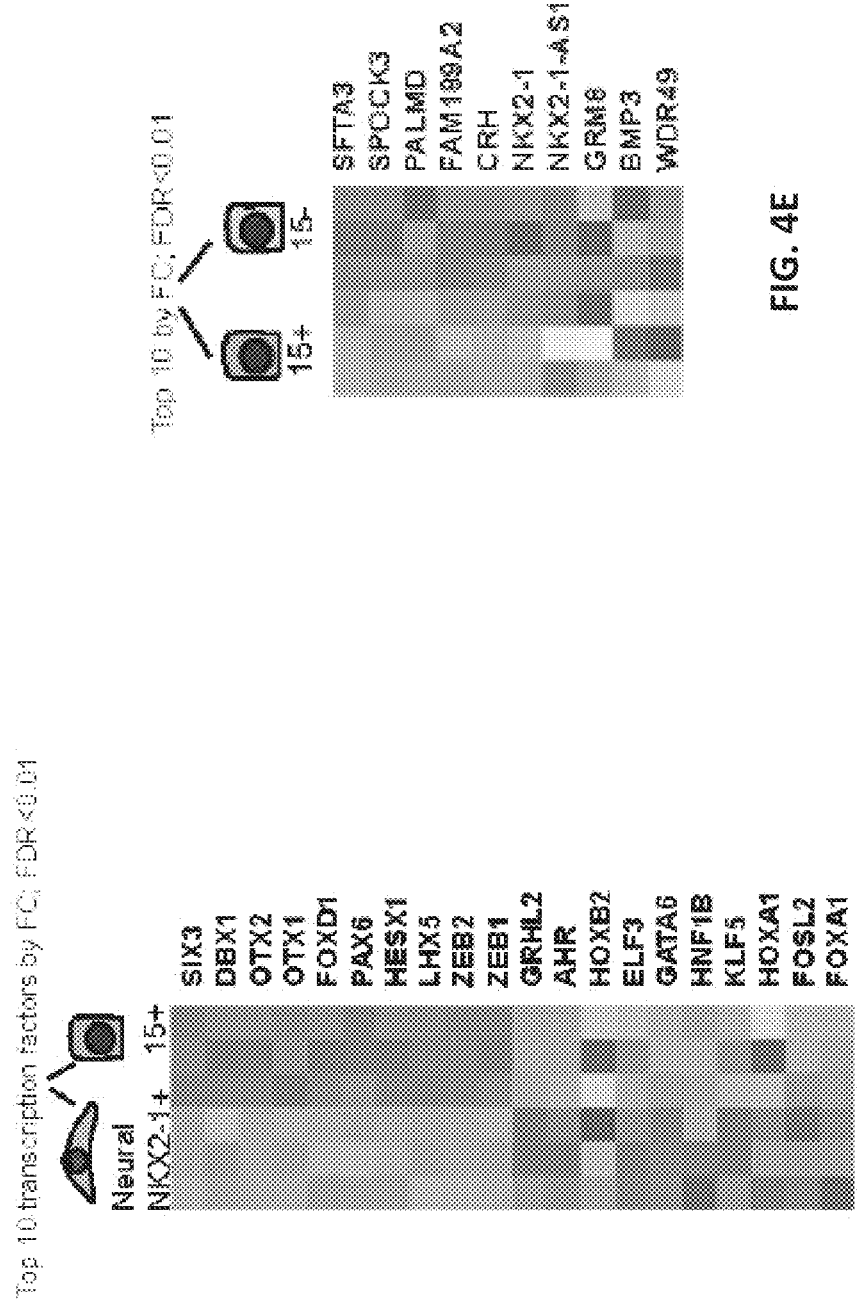

Principal components analysis (PCA) indicated the global transcriptome of NKX2-1$^{GFP+}$ lung cells was easily distinguished from NKX2-1$^{GFP+}$ neural cells (FIG. 4B). Unsupervised hierarchical clustering of all 27 samples based on the top ~1000 transcripts differentially expressed by ANOVA (1032 genes at $p<5\times10^{-13}$) revealed that day 15 and 28 cells prepared in the lung directed differentiation protocol clustered closer to distal fetal lung epithelial controls than to endoderm or neural NKX2-1+ cells (FIG. 4C). The transcriptional profile of neural NKX2-1$^{GFP+}$ cells compared to lung NKX2-1$^{GFP+}$ cells (day 15) included 4329 differentially expressed transcripts (FDR-adjusted $p<0.01$) and a distinct set of transcription factors including SIX3, DBX1, OTX1, OTX2, FOXD1, PAX6, and LHX5 (Ranked by fold change, filtered by FC>5, FDR<0.01 and GO:0003700: "transcription factor activity, sequence-specific DNA binding"; FIG. 4D) further emphasizing the marked differences between these early NKX2-1+ forebrain and lung progenitors. Directed differentiation protocols have previously used FOXA2 expression as a marker to define an NKX2-1 population as endodermal and TUJ1 to indicate neuroectodermal fate, but it was found that FOXA2 is expressed in both neuronal and lung populations (FIG. 4F), and that TUJ1 is not highly expressed in the neuronal NKX2-1+ population indicating neither marker is useful in distinguishing NKX2-1+ neural from lung lineages. In contrast, the top 10 transcription factors differentially expressed in Day 15 lung NKX2-1$^{GFP+}$ vs. neuronal NKX2-1$^{GFP+}$ cells include 6 genes expressed in the developing lung (GRHL2, ELF3, GATA6, HNF1B, HOXA1 and FOXA1 (FIG. 4D) (26-28)

indicating a constellation of transcripts better able to distinguish these two iPSC-derived populations.

Figure 11A:
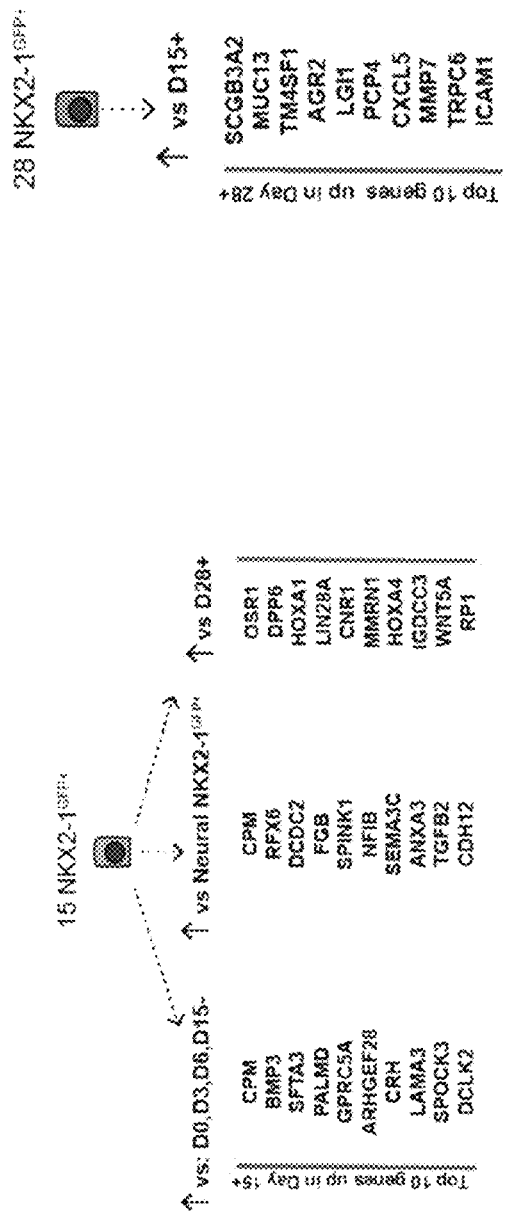
FIG. 11A-FIG. 11D Gene signature of iPSC-derived lung progenitors and a kinetic of foregut and early lung transcription factors.
Figure 11B:
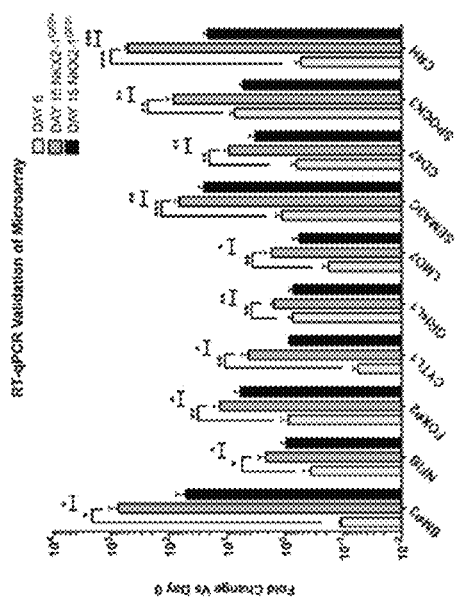

To interrogate the differences between day 15 NKX2-1$^{GFP+}$ and NKX2-1$^{GFP-}$ cells at the primordial progenitor stage, the top 10 differentially expressed genes were ranked by fold change (FIG. 4E). NKX2-1 as well as neighboring lncRNAs SFTA3 and NKX2-1AS were highly upregulated in the GFP+ population. Also in this top 10 list were genes (BMP3, CRH and SPOCK3) previously described in lung development (FIG. 4E) (26-32) and validated using RT-qPCR in FIG. 11B. The finding that SFTA3 (aka NANCI: NKX2-1 associated non-coding intergenic RNA) is the top differentially expressed transcript in the genome distinguishing day 15 NKX2-1$^{GFP+}$ cells is in keeping with recent publications that in developing mouse lungs this transcript is co-expressed with Nkx2-1 and shares the same regional and temporal expression pattern (33). Four genes in this list (PALMD, FAM189A2, GRM8, WDR49) have not been previously identified in the lung epithelium.

Figures 4F, 5:
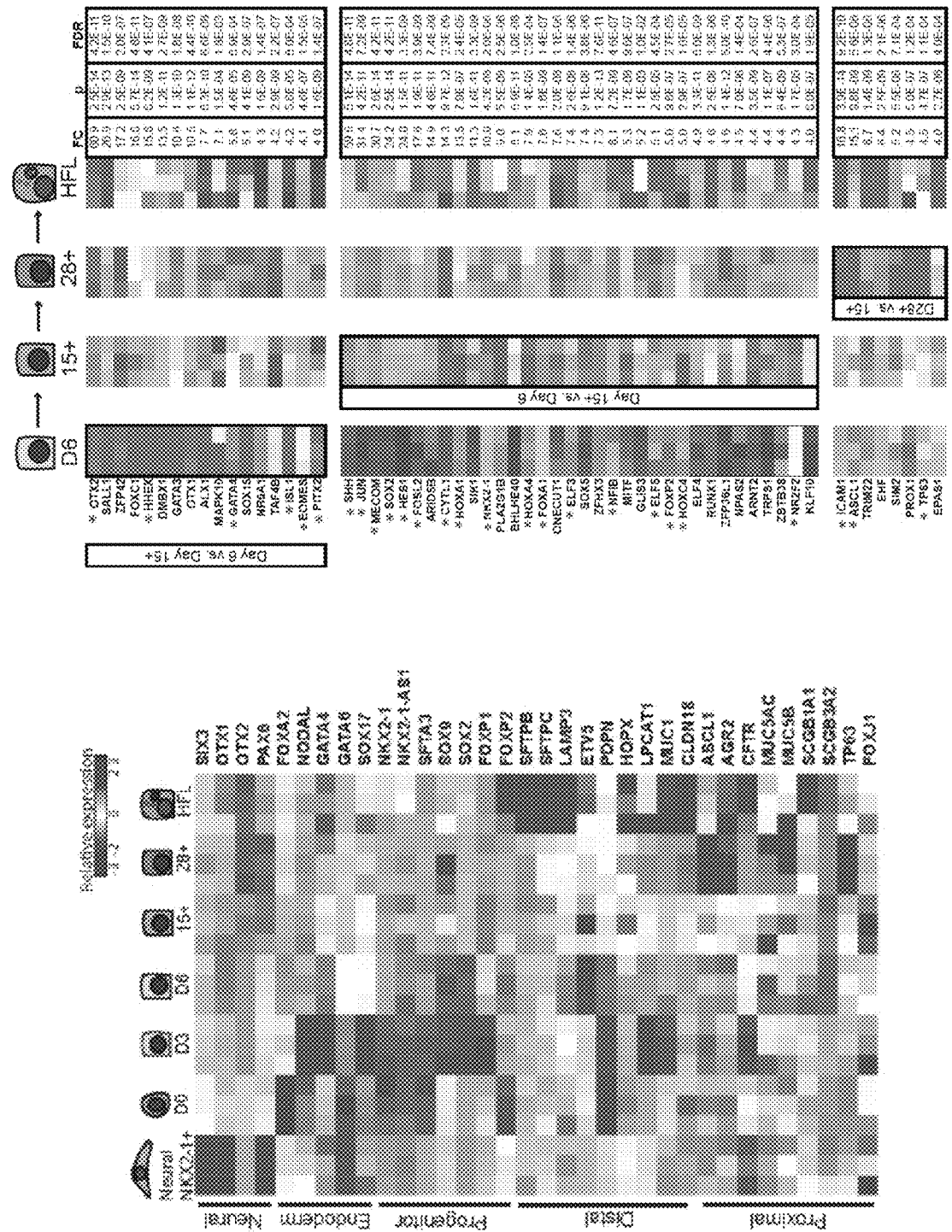
FIG. 5 Transcriptomic signatures of iPSC-derived anterior foregut endoderm and lung progenitors, focused on genes associates with transcription factor activity. Heatmap of the top transcription factors or genes with transcription factor activity GO terms that are differentially expressed (filtered by FC>4) between successive stages of lung differentiation starting from day 6 and compared to human fetal lung. Vertical text box and heatmap with black outline identify the signature of each stage being analyzed. See also FIG. 11 and Table 2.

From the microarray datasets known markers of definitive endoderm, forebrain and 24 genes of known importance were selected in the developing lung epithelium and their expression patterns were profiled over the course of directed differentiation in comparison to human fetal epithelial lung control cells (HFL) (FIG. 4F). Endodermal markers, such as GATA4, GATA6, SOX17, NODAL and FOXA2 were upregulated early during endodermal differentiation with retained expression of GATA6 and FOXA2 in Day 15 and Day 28 NKX2-1$^{GFP+}$ cells. In contrast the transcripts NKX2-1, SFTA3, SOX9, and FOXP family members were low or absent prior to day 6, and their clear emergence in the day 15 GFP+ population is consistent with their published expression during the early lung progenitor period in mouse lung development (35, 36). These findings together with the lack of mature lung marker gene expression in day 15 GFP+ cells (low SCGB1A1, SCGB3A2, TP63, SFTPB and SFTPC) further indicate the day 15 GFP+ population represents a relatively undifferentiated or "primordial" lung progenitor population, as has been observed in early Nkx2-1+ progenitors in developing mouse cells in vivo (28). In contrast to day 15, by day 28 the GFP+ population had begun to express markers known to be enriched in maturing alveolar epithelial cells (ETV5, CLDN18, LPCAT1, MUC1, SFTPB, low SFTPC) or in airway epithelia, such as basal (TP63), secretory (SCGB3A2, MUC5B, MUC5AC, AGR2), ciliated (FOXJ1, CFTR) and neuroendocrine (ASCL1) cells. PDPN, which has occasionally been referred to as a PSC-derived type 1 pneumocyte marker in prior publications (8, 9), was actually expressed in day 0 as well as day 15 GFP+ cells, consistent with its expression patterns in developing mice where it is robustly expressed in both the foregut endoderm and the developing pseudoglandular lung epithelium prior to the emergence of type 1 cells (37).

Next the inventors sought to identify unbiased gene signatures of primordial (day 15) and maturing (day 28) NKX2-1$^{GFP+}$ cells. Lists of the top 100 differentially expressed genes (ranked by fold change, filtered by FDR<0.01) of each sample were generated across multiple comparisons and a common gene set was identified for each sample (FIG. 11, Table 1). The day 28 GFP negative population was enriched for diverse but predominantly liver (APOA2, FGB, AFP, CDH17 and TF) and intestinal (CDX2, CDH17 and GIF) markers (Table 1). In addition to NKX2-1, SFTA3, CPM, NFIB, and CRH, which are all expressed in primordial lung progenitors, the maturing lung cells (day 28 GFP+) expressed higher levels of SCGB3A2, SFTPB, TP63, ICAM1, IL8 and ITGB6 (FIG. 11, Table 1). SCGB3A2 was the most differentially expressed transcript of 23,786 probe sets ranked by fold change (day 28 GFP+vs. GFP- groups; FC=76.6; FDR adjusted p=$1.6 \times 10^{-9}$). SFTPC was upregulated by day 28 (GFP+) but not yet at levels equivalent to HFL, findings in keeping with the recombinant experiments, which indicated that current differentiation protocols without the use of primary mesenchyme have not yet optimized for efficient and full distal alveolar maturation (FIG. 3C-3D, 10D, 4F and Table 1).

TABLE 1

The top 100 differentially expressed genes (ranked by fold change, filtered by FDR <0.01) of day 15 NKX2-1$^{GFP+}$, day 28 NKX2-1$^{GFP+}$ and day 28 NKX2-1$^{GFP-}$ samples (top row indicates sample being analyzed) across multiple comparisons (second row indicates sample being compared to)

| | Day 15 NKX2-1$^{GFP+}$ vs. | | | | | |
|---|---|---|---|---|---|---|
| | Day 0 (iPSC) | Day 3 (Definitive Endoderm) | Day 6 (Ant. Foregut Endoderm) | Day 15 NKX2-1$^{GFP-}$ | Neural NKX2-1$^{GFP+}$ | Day 28 NKX2-1$^{GFP+}$ |
| 1 | CPM | CPM | CPM | SFTA3 | CPM | OSR1 |
| 2 | LINC00261 | RFX6 | SHH | SPOCK3 | RFX6 | DPP6 |
| 3 | RFX6 | EFEMP1 | FGB | PALMD | DCDC2 | HOXA1 |
| 4 | SFTA3 | DCDC2 | RFX6 | FAM189A2 | FGB | LIN28A |
| 5 | FAM198B | SFTA3 | FAM198B | CRH | SPINK1 | CNR1 |
| 6 | SHH | FAM198B | SPINK1 | NKX2-1 | NFIB | MMRN1 |
| 7 | FGB | TGFB2 | CLIC6 | NKX2-1-AS1 | SEMA3C | HOXA4 |
| 8 | CDH12 | FGB | BMP3 | GRM8 | ANXA3 | LOC100996304 |
| 9 | SEMA3C | SEMA3C | SEMA3C | BMP3 | TGFB2 | IGDCC3 |
| 10 | DCDC2 | MBNL1 | SULT1E1 | WDR49 | CDH12 | WNT5A |
| 11 | LOC400043 | SHH | SFTA3 | TPPP3 | LOC400043 | RP1 |
| 12 | MECOM | CLDN4 | ALDH1A1 | LRRC7 | CCDC68 | LPPR3 |
| 13 | NR2F2 | SPINK1 | MACC1 | GPC4 | GPR126 | B3GALT1 |
| 14 | BMP3 | NR2F2 | DCDC2 | KAL1 | CLIC6 | PRTG |
| 15 | FOXA1 | MACC1 | PLEKHG1 | LOC100996304 | HNF1A-AS1 | EFHC2 |
| 16 | TPPP3 | MIR181B1 | JUN | WNT7B | SULT1E1 | LRAT |
| 17 | SULT1E1 | CTNND2 | LOC100131234 | ACADL | BMP3 | METRN |
| 18 | RNASE4 | MET | MECOM | PLA2G1B | FGG | SLC6A4 |
| 19 | TGFB2 | LOC400043 | TPPP3 | C1orf192 | SEMA3D | ARMC3 |
| 20 | SPINK1 | EFNB2 | LOC400043 | LAMA3 | SLC44A3 | ZBTB16 |
| 21 | RARB | PROM1 | MIR181B1 | CEACAM6 | SNORA72 | TSHZ1 |
| 22 | ERP27 | SULT1E1 | CTNND2 | ANKRD29 | GRHL2 | DAB1 |

TABLE 1-continued

The top 100 differentially expressed genes (ranked by fold change, filtered by FDR <0.01) of day 15 NKX2-1$^{GFP+}$, day 28 NKX2-1$^{GFP+}$ and day 28 NKX2-1$^{GFP-}$ samples (top row indicates sample being analyzed) across multiple comparisons (second row indicates sample being compared to)

Day 15 NKX2-1$^{GFP+}$ vs.

| | Day 0 (iPSC) | Day 3 (Definitive Endoderm) | Day 6 (Ant. Foregut Endoderm) | Day 15 NKX2-1$^{GFP-}$ | Neural NKX2-1$^{GFP+}$ | Day 28 NKX2-1$^{GFP+}$ |
|---|---|---|---|---|---|---|
| 23 | FGG | SOX2 | GPRC5A | GFRA1 | TMPRSS2 | LPPR1 |
| 24 | HNF1A-AS1 | PLEKHG1 | MBNL1 | LOC145837 | AHR | DSCAM |
| 25 | TTR | FOXA1 | SOX2 | ADRA2A | PALMD | ALPL |
| 26 | MEIS2 | BMP3 | HES1 | EEF1DP3 | FAM3B | LOC100873065 |
| 27 | PALMD | ANXA1 | FGG | GPRC5A | S100A10 | LOC400043 |
| 28 | PLEKHG1 | LOC100131234 | ARHGEF28 | PION | EPSTI1 | SPG20OS |
| 29 | HOX62 | CCDC68 | GFRA1 | LOC100505659 | TTR | KRT4 |
| 30 | GPRC5A | SUSD4 | RBMS3 | ABCA8 | ARHGEF28 | CA14 |
| 31 | ARID5B | HNF1A-AS1 | THBS1 | CPM | OSR1 | COL2A1 |
| 32 | MIR181B1 | ARHGEF28 | CFI | PPP1R14C | SNORA75 | SLIT1 |
| 33 | ARHGEF28 | ERP27 | CDH12 | NELL1 | GPRC5A | TRPC4 |
| 34 | ALDH1A1 | CD47 | RP1 | RDH10 | MACC1 | CXorf22 |
| 35 | NKX2-1 | TTR | LOC100996304 | CHRDL1 | LOC100996304 | METTL24 |
| 36 | CCDC92 | FREM2 | HNF1A-AS1 | LOC100505676 | SPOCK3 | HULC |
| 37 | SI | EGR1 | OSR1 | CELSR1 | RP1 | RFX6 |
| 38 | C5 | RND3 | NPNT | RP1 | HOXB2 | CXorf30 |
| 39 | GPR126 | FGG | SI | LRRTM1 | LMO7 | ANKRD29 |
| 40 | CCDC68 | EDN1 | FOSL2 | NRK | SNORA14A | LOC100506013 |
| 41 | LOC100131234 | PALMD | CCDC68 | CRLF1 | LAMA3 | DENND3 |
| 42 | CTNND2 | CDH12 | CRH | DSCR6 | ALDH1A1 | STC1 |
| 43 | MIR27B | LOC100996304 | LAMA3 | HORMAD2 | SI | MIR181B1 |
| 44 | CLIC6 | AHR | PALMD | SLC16A12 | ERBB3 | SLC7A3 |
| 45 | TBC1D9 | DHRS3 | DCLK2 | MIR614 | ELF3 | DLGAP2 |
| 46 | OSR1 | NKX2-1 | LYPD1 | PRMT8 | ST14 | HOXC5 |
| 47 | RP1 | SI | C14orf105 | WIF1 | LOC100131234 | GREB1 |
| 48 | LOC100996304 | OSR1 | CDH6 | PAQR5 | CRH | FAM46B |
| 49 | CFI | LRRTM1 | CHRDL1 | SDPR | GATA6 | HOXC4 |
| 50 | GATA6 | GPRC5A | ARID5B | IFI6 | ACSL1 | SMAD9 |
| 51 | EP5TI1 | GPC3 | IGFBP7 | MUC1 | CFI | C3orf15 |
| 52 | SPOCK3 | GFRA1 | PLAGL1 | CFI | MET | ZNF703 |
| 53 | C14orf105 | SPTLC3 | CYTL1 | HHLA2 | MPZL2 | CECR2 |
| 54 | LOC100507319 | CDH6 | IGSF10 | SLCO2A1 | LOC100507319 | ODZ3 |
| 55 | HNF1B | CLIC6 | CXCR7 | PIK3AP1 | CLDN4 | TEKT3 |
| 56 | CRH | CAPN6 | MIR100HG | SLC6A4 | LCP1 | SCMH1 |
| 57 | KREMEN1 | ALDH1A1 | ANKRD29 | STK32B | FAM198B | GABRB1 |
| 58 | H19 | COL2A1 | HOXA1 | ELF5 | IGSF10 | TMEM178A |
| 59 | RBMS3 | LOC400706 | RDH10 | KREMEN1 | MIR181B1 | CCDC136 |
| 60 | MBNL2 | NDNF | GRM8 | PRDM16 | HNF1B | TUBB4A |
| 61 | MYOF | SPOCK3 | SPOCK3 | DENND3 | DSP | FBN3 |
| 62 | SULT1C4 | BICC1 | FAM3B | ZDHHC14 | C1orf116 | KCNIP1 |
| 63 | HORMAD2 | C3orf15 | CPA6 | CP | TPPP3 | RBM20 |
| 64 | RNASE1 | CDH11 | ABCA8 | PTPRZ1 | MIR27B | PRMT8 |
| 65 | PLCE1 | THBS1 | LGALS3 | MAP2 | RNASE1 | LRRC7 |
| 66 | LAMA3 | CRH | SORBS2 | FRY | CDH1 | ST8SIA2 |
| 67 | SNORA60 | LEF1 | SLIT1 | CLIC6 | C17orf110 | LOC100996452 |
| 68 | NPNT | DPP6 | H19 | CYTL1 | MYOF | ABCA8 |
| 69 | ABCA8 | C14orf105 | RND3 | ARHGEF28 | C14orf105 | IGDCC4 |
| 70 | ZFHX3 | MAP2 | PRDM16 | RNASE1 | KLF5 | SYTL5 |
| 71 | DCLK2 | SCUBE3 | KCNIP1 | KCNH7 | TES | ARHGAP24 |
| 72 | NDNF | LRP2 | CNR1 | DPP6 | ATP8B1 | CRHBP |
| 73 | TNFRSF19 | TMPRSS2 | GUCY1A3 | MAPK8IP1 | ABCA8 | ILDR2 |
| 74 | TSHZ1 | SLC44A3 | HHLA2 | NMU | SLCO4C1 | GPM6A |
| 75 | GUCY1A3 | LAMA3 | CDH17 | DSCAM | SNORA65 | RNF157 |
| 76 | SLC40A1 | DCLK2 | SIK1 | KRT4 | NPNT | RDH10 |
| 77 | FRMD4B | CFI | NRK | DCLK2 | FAM189A2 | DPEP1 |
| 78 | CPA6 | MIR21 | MTTP | SOX2 | GALNT3 | SCUBE3 |
| 79 | HSBP1L1 | GRHL2 | FAM189A2 | NPAS2 | MAN1A1 | MEGF10 |
| 80 | SLC44A3 | MECOM | HORMAD2 | NEDD9 | HOXA1 | AIM2 |
| 81 | PRDM16 | MIR100HG | GUCY1A2 | PCDH20 | RDH10 | TRIM71 |
| 82 | SLIT1 | B3GALT1 | TNS1 | FLVCR2 | EDN1 | LINC00348 |
| 83 | FRK | IGSF10 | CD47 | BAAT | ARAP2 | LOC650368 |
| 84 | ZNF703 | RP1 | CAPN6 | CAPN6 | LGALS3 | POPDC3 |
| 85 | IGSF10 | MEI52 | KREMEN1 | ARMC3 | CDH17 | GNG7 |
| 86 | CDH17 | CHRDL1 | ADAMTS16 | IRX1 | FRK | GADL1 |
| 87 | HOXA1 | FOSL2 | NKX2-1 | LOC283070 | TGFB3 | FZD8 |
| 88 | SNORA11 | IGFBP7 | ANXA1 | KCNH8 | LOC400706 | RAB38 |
| 89 | MEIS1 | ABCA8 | PHLDA1 | SP110 | TPD52L1 | WFIKKN1 |
| 90 | C17orf110 | MPZL2 | NKX2-1-AS1 | ADAMTSL1 | DSCR6 | KCTD15 |
| 91 | TGFB3 | RAB27B | LMO7 | LURAP1L | FOSL2 | SALL4 |
| 92 | NKX2-1-AS1 | HOXA1 | EDN1 | TBC1D2 | HORMAD2 | ENO4 |

TABLE 1-continued

The top 100 differentially expressed genes (ranked by fold change, filtered by FDR <0.01) of day 15 NKX2-1$^{GFP+}$, day 28 NKX2-1$^{GFP+}$ and day 28 NKX2-1$^{GFP-}$ samples (top row indicates sample being analyzed) across multiple comparisons (second row indicates sample being compared to)

Day 15 NKX2-1$^{GFP+}$ vs.

| | Day 0 (iPSC) | Day 3 (Definitive Endoderm) | Day 6 (Ant. Foregut Endoderm) | Day 15 NKX2-1$^{GFP-}$ | Neural NKX2-1$^{GFP+}$ | Day 28 NKX2-1$^{GFP+}$ |
|---|---|---|---|---|---|---|
| 93 | RHOBTB3 | RDH10 | HOXA2 | SYT17 | VTRNA1-1 | SNED1 |
| 94 | LOC100128893 | H19 | RAB27B | AQP7 | SNORD90 | MTL5 |
| 95 | JUN | ARID5B | HOXB2 | LEPREL1 | ANKRD29 | FLVCR2 |
| 96 | HHLA2 | ELF3 | BICC1 | TMC5 | PLCE1 | PBX1 |
| 97 | SOX5 | CDH17 | TMEM117 | GPM6A | GRB14 | WDR86 |
| 98 | SEMA3D | SLC4A4 | TMPRSS2 | PDE1A | SPG20OS | ZDHHC8P1 |
| 99 | MPZL2 | GRM8 | DHRS3 | ADAMTS16 | FOXA1 | COL18A1 |
| 100 | COL2A1 | RBMS3 | BCL11A | EPHA7 | CPA6 | SEPT3 |

Figure 11C:
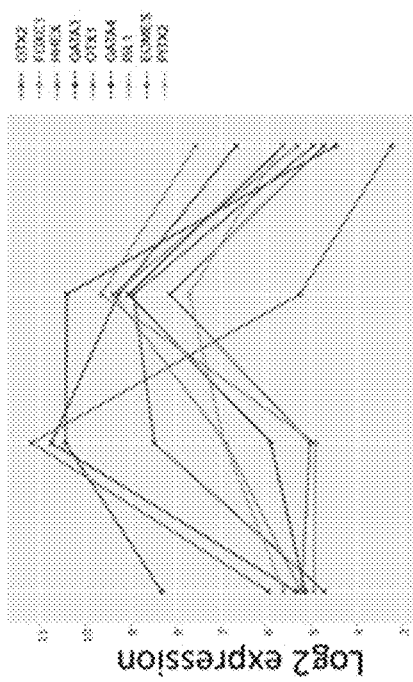
Figure 11D:
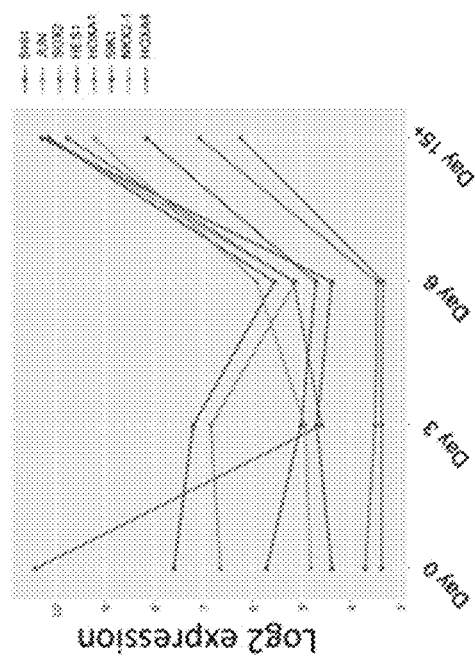

Transcription factors play critical roles in organogenesis including in lung development (27). To identify candidate genes that control human lung specification and development, enrichment of transcription factors or regulators of transcription were screened for prior to lung specification (day 6) and at different stages of lung maturity (day 15 NKX2-1$^{GFP+}$, day 28 NKX2-1$^{GFP+}$ and HFL; FIG. 5). To identify genes of interest the significantly differentially expressed genes were ranked by fold change (FC>4; FDR<0.01) and filtered genes based on gene ontology (GO) classification for transcription factor activity (GO:0003700, "transcription factor activity"). The majority of the most highly differentially expressed genes in day 6 anterior foregut-like endoderm were known transcription factors of the foregut endoderm previously described in *xenopus* and mouse model systems; HHEX, GATA3, GATA4, FOXC1, EOMES, OTX1, OTX2, ISL1 and PITX2 (28, 38, 39) (FIGS. 5, 11C, Table 2). In comparison to day 6, the day 15 NKX2-1GFP+ population was enriched for many transcription factors known to be present in the developing mouse lung (JUN, MECOM, SOX2, HES1, HOXA1, NKX2-1, FOXA1, ELF3, ELF5, NFIB, FOXP2) (24-26, 37-43) (FIG. 5, 11D, Table 2). In addition to HOXA1 a number of other HOX genes were upregulated in day 15 NKX2-1$^{GFP+}$ samples (HOXA4, HOXC4). SHH, essential for normal lung development in mice (27), was the most highly expressed gene in the day 15 samples in the analysis (fold change 60, p=5×10$^{-14}$, FDR 4.8×10$^{-11}$). Day 28 NKX2-1$^{GFP+}$ cells expressed higher levels of transcription factors associated with basal cells (TP63) and neuroendocrine cells (ASCL1). Taken together these time series data provide unbiased stage-dependent signatures of the putative transcriptomic programs of human lung progenitors and their differentiated progeny as they emerge during developmental directed differentiation. Moreover these signatures reveal that many evolutionarily conserved transcription factors, previously observed in developing *xenopus* and mouse lung endoderm in vivo, are also differentially expressed in the iPSC human lung development model system.

TABLE 2

| Gene | Publications |
|---|---|
| Otx2 | (Rankin et al., 2011) |
| Hhex | (Herriges et al., 2012; Rankin et al., 2011; Zorn and Wells, 2009) |
| Gata4 | (Zorn and Wells, 2009) |
| Isl1 | (Millien et al., 2008) |

TABLE 2-continued

| Gene | Publications |
|---|---|
| Eomes | (Zorn and Wells, 2009) |
| Pitx2 | (Millien et al., 2008) |
| Shh | (Maeda et al., 2007; Zorn and Wells, 2009) |
| Jun | (Maeda et al., 2007) |
| Mecom | (Perkins et al., 1991) |
| Sox2 | (Herriges et al., 2012; Zorn and Wells, 2009) |
| Hes1 | (Maeda et al., 2007) |
| Fosl2 | Eurexpress.org |
| Cytl1 | Eurexpress.org |
| Hoxa1 | (Herriges et al., 2012; Millien et al., 2008) |
| Nkx2-1 | (Herriges et al., 2012; Millien et al., 2008; Zorn and Wells, 2009) |
| Hoxa4 | (Millien et al., 2008) |
| Foxa1 | (Herriges et al., 2012) |
| Elf3 | (Maeda et al., 2007) |
| Nfib | (Millien et al., 2008) |
| Elf5 | (Herriges et al., 2012; Metzger et al., 2007) |
| Foxp2 | (Lu et al., 2002) |
| Hoxc4 | (Millien et al., 2008) |
| Nr2f2 | (Maeda et al., 2007) |
| Icam1 | (Attar et al., 1999) |
| Ascl1 | (Li and Linnoila, 2012) |
| Tp63 | (Millien et al., 2008) |

Single Cell RNA Sequencing and Surface Marker Profiling of Day 15 iPSC-Derived Lung Progenitors.

Figure 6A:
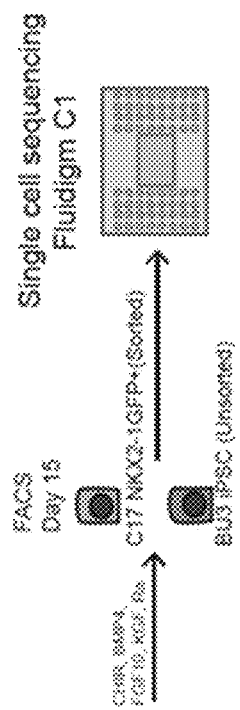
FIG. 6A-FIG. 6G Single cell RNA sequencing of sorted and unsorted iPSC-derived cells reveals NKX2-1+"lung" and NKX2-1− non-lung lineages and indicates markers for their identification.
Figure 6B:
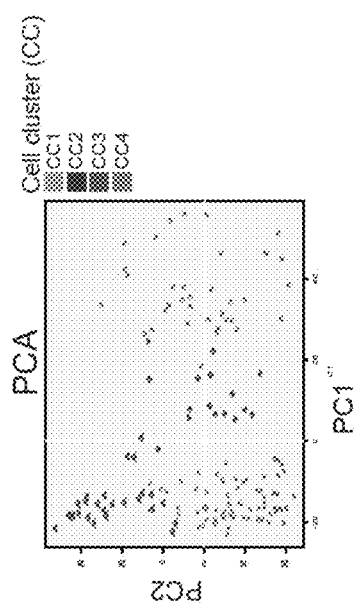

While transcriptomic profiles of purified groups of cells allow a deep understanding of the genetic program of the NKX2-1+ progenitor population, it does not allow interrogation of the heterogeneity of these programs at the individual cell level. Hence, it was next sought to profile the transcriptomic programs of individual iPSC-derived cells at the day 15 stage of lung differentiation employing the C17 NKX2-1$^{GFP}$ targeted line as well as the untargeted iPSC line (BU3) (19). RNA sequencing was performed on 84 BU3 iPSC-derived cells without any cell sorting and 69 C17 iPSC-derived cells, sorted based on NKX2-1$^{GFP+}$ expression (FIG. 6A). PCA (FIG. 6B) of gene expression variance as well as unsupervised hierarchical clustering analysis (FIG. 6C) both indicated 4 broad clusters of cells (hereafter CC1-CC4) were present on day 15. Notably, three of the four clusters (CC1, CC2, and CC4) expressed high levels of NKX2-1 (FIG. 6C) whereas cluster CC3 exhibited an absence of transcripts encoded by the NKX2-1 locus or its neighboring locus, SFTA3. NKX2-1 expressing clusters were most robustly distinguished by whether they exhibited mitotic (CC1 and CC2) or non-cycling (CC4) gene signatures. For example, CC1 and CC2 were highly enriched for the expression of genes associated with mitosis or cytokinesis (e.g. KIF11, KIF14, KIF22, KIF23, CDC20, and AURKB). Thus, CC1 was labeled "mitotic" and CC2 was labeled "pre-mitotic" based on slightly lower expression levels of these markers in the latter cluster, whereas CC3 and CC4 did not appear to be in active cycle at the time of analysis.

Figure 6C:
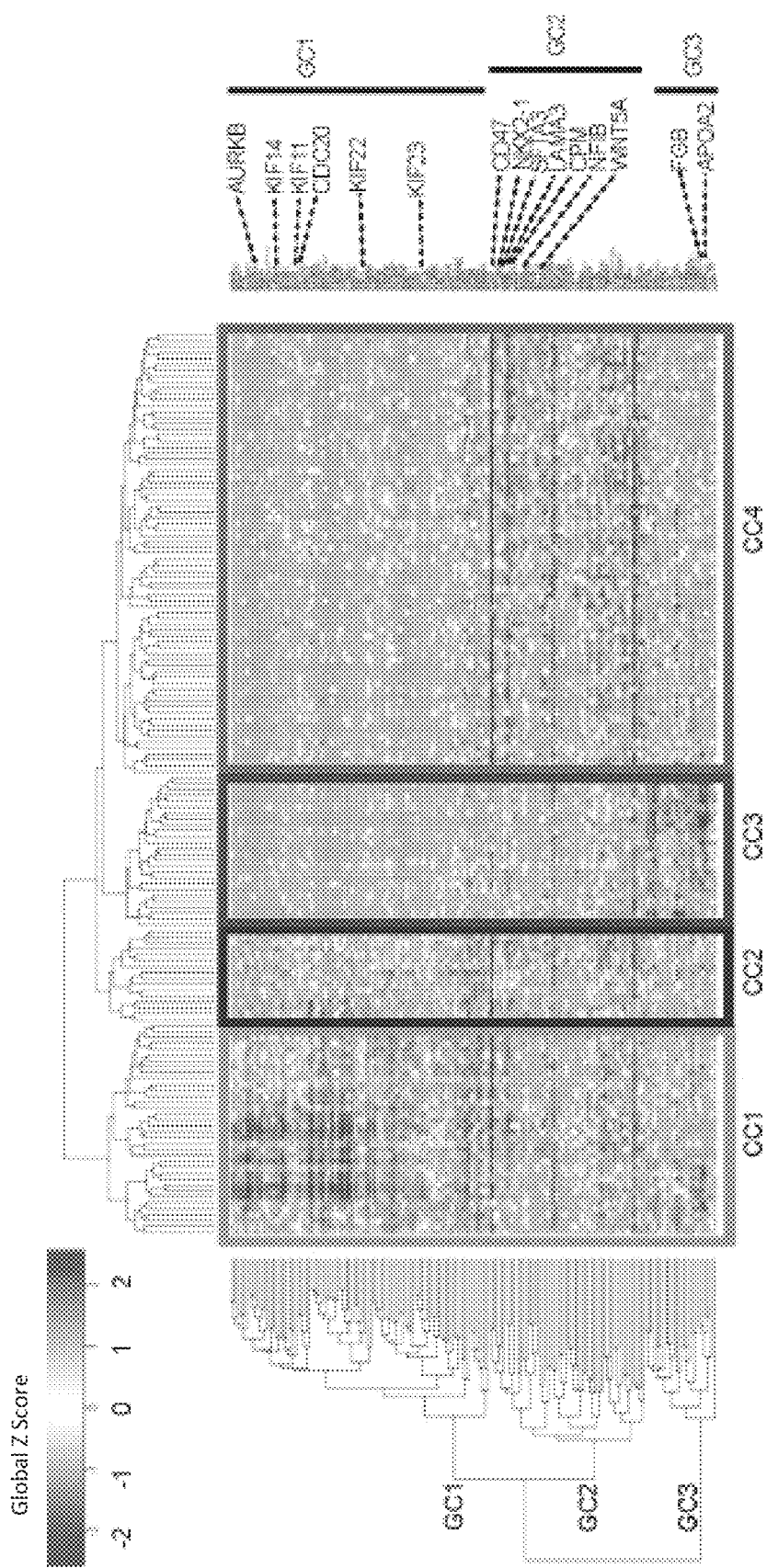

Importantly NKX2-1+ cells clustered together (CC4) regardless of whether they were sorted GFP+C17 iPSCs or unsorted BU3 iPSCs. Furthermore, only 1 GFP+ sorted cell could be found "misclustering" amongst the 26 cells that comprised the NKX2-1 negative cluster (SC2) and as expected 25 out of 26 cells found in this NKX2-1 negative cluster derived from the unsorted BU3 iPSCs (FIG. 6C).

Figures 6D, 6E:
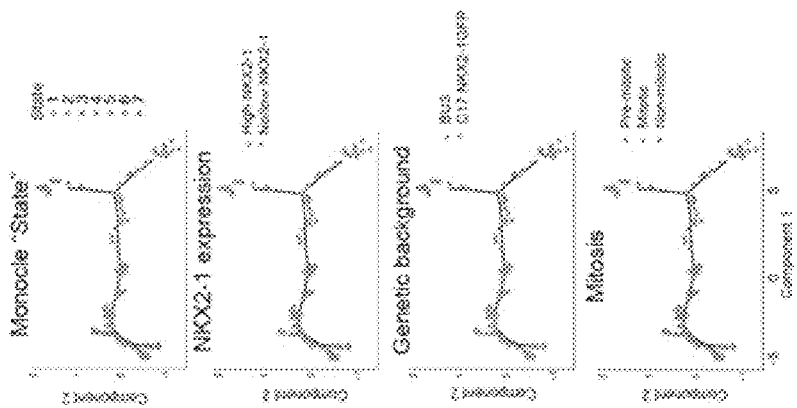
Figure 6G:
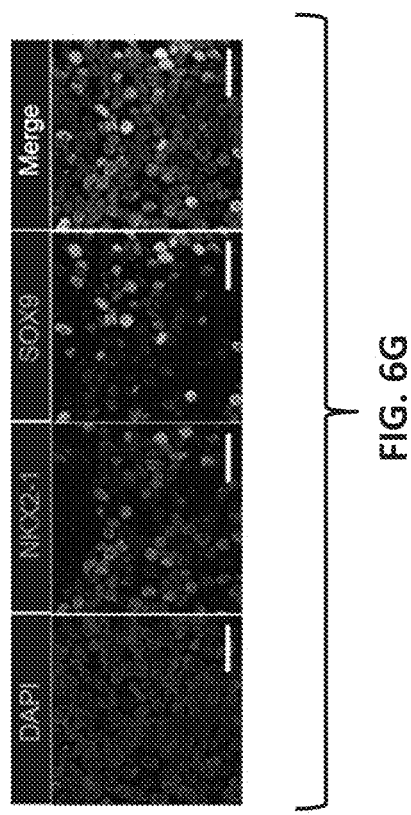
Figure 12A:
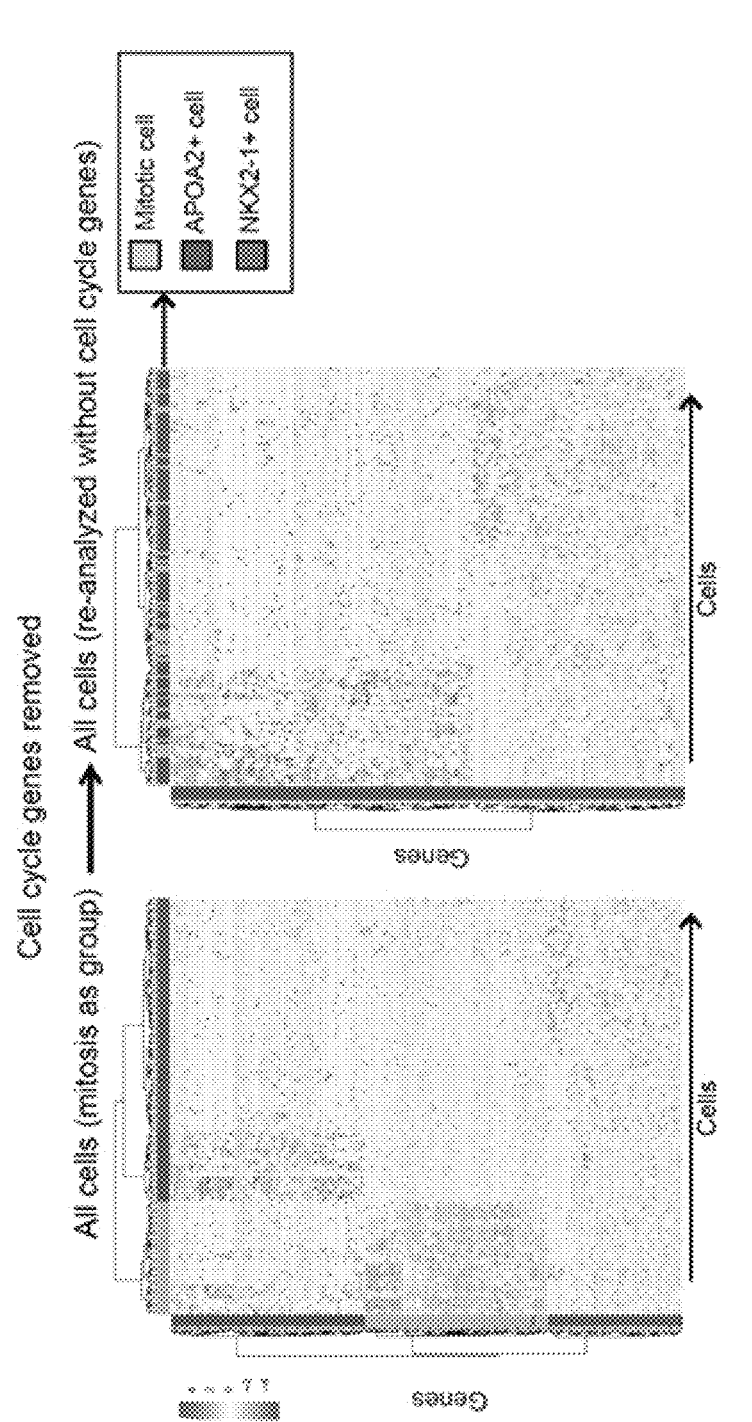
FIG. 12A-FIG. 12D Single cell RNA-Seq analysis of 153 iPSC-derived cells on day 15 of differentiation.

Three approaches were taken to interrogate the gene expression differences that distinguished each cell cluster. First, unsupervised hierarchical clustering of the top 150 most differentially expressed genes was used (FIG. 6C; y-axis dendrograms; hereafter gene clusters GC1-3). It was found that GC1 was highly enriched for cell-cycle regulation genes (including AURKB, BIRC5, BUB1, CCNB1, CCNB2, CENPE, CENPF, KIF11, KIF14, KIF22, KIF23, KIF22c, MELK, TOP2A; FIG. 6C) further supporting the interpretation that changes in genes of cytokinesis and cell cycle dominate the first level of clustering of day 15 cells. However, two additional distinct gene clusters were also apparent, most notably GC2, including NKX2-1, SFTA3, NFIB, CD47, WNT5A, CPM and LAMA3; and GC3 which was associated with the NKX2-1 negative/SFTA3 negative cells of CC3 (FIG. 6C). This analysis identified GC2 genes as potential markers associated with NKX2-1+ lung cells, and GC3 genes as potential markers associated with "nonlung" (NKX2-1 negative) cells. Consistent with this observation, the top 10 genes most highly correlated with NKX2-1 expression across individual cells were GC2 genes, including CD47, SFTA3, CPM, and LAMA3 (FIG. 6D). In contrast, GC3 was enriched in liver lineage genes (APOA2 and FGB) as well as non-specific mesenchymal genes (COL19A1 and S100A10). The inventors have previously published that in iPSC-derived hepatic cells, FGB represents the most upregulated transcript in the genome during hepatic directed differentiation. Furthermore, in postnatal human tissues both APOA2 and FGB are transcripts specifically enriched in liver cells. Significantly all NKX2-1 negative cells of putative hepatic lineage (20 out of 20 APOA2+ cells; FIG. 6C) were solely comprised of unsorted BU3 iPSCs indicating that sorting on the NKX2-1$^{GFP+}$ marker successfully depleted any contaminating hepatic cells in this protocol. The majority of cells (23/37) in the "mitotic" and "pre-mitotic" groups clustered with NKX2-1+/CD47+ cells when hierarchical clustering was re-run after cell cycle genes were removed (FIG. 12A).

Figure 6F:
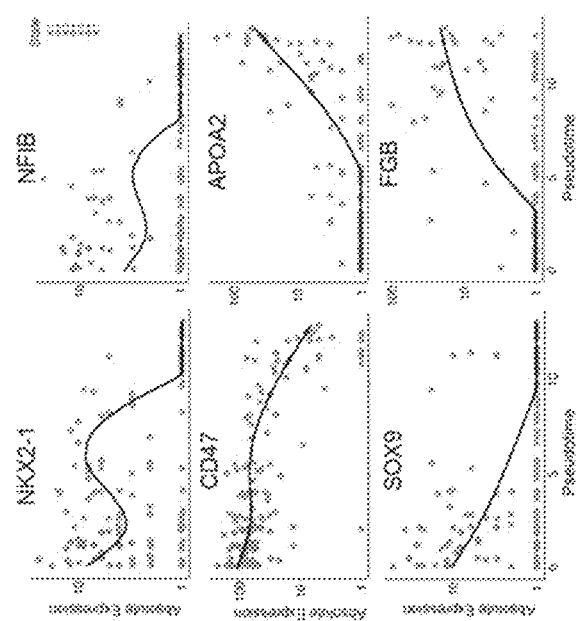
Figure 12C:
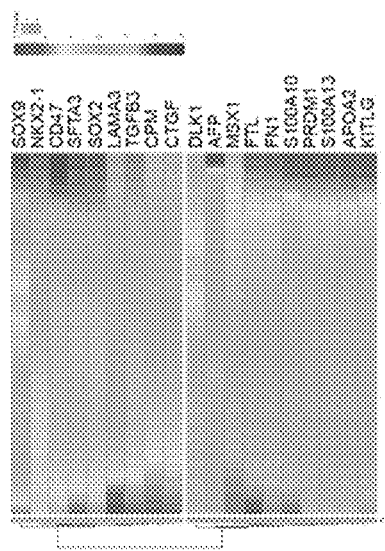
Figure 12B:
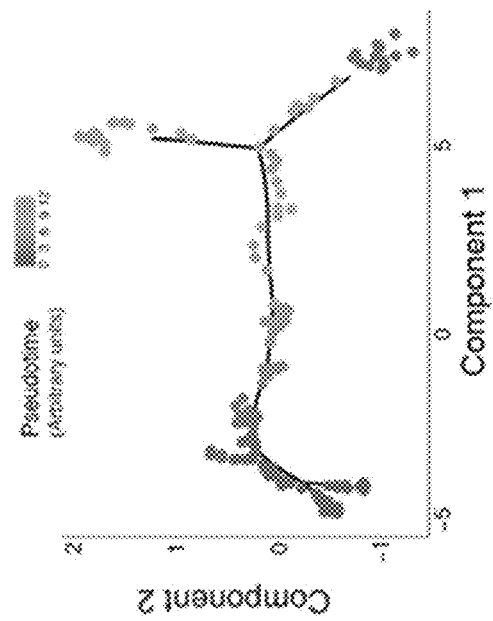
Figure 12D:
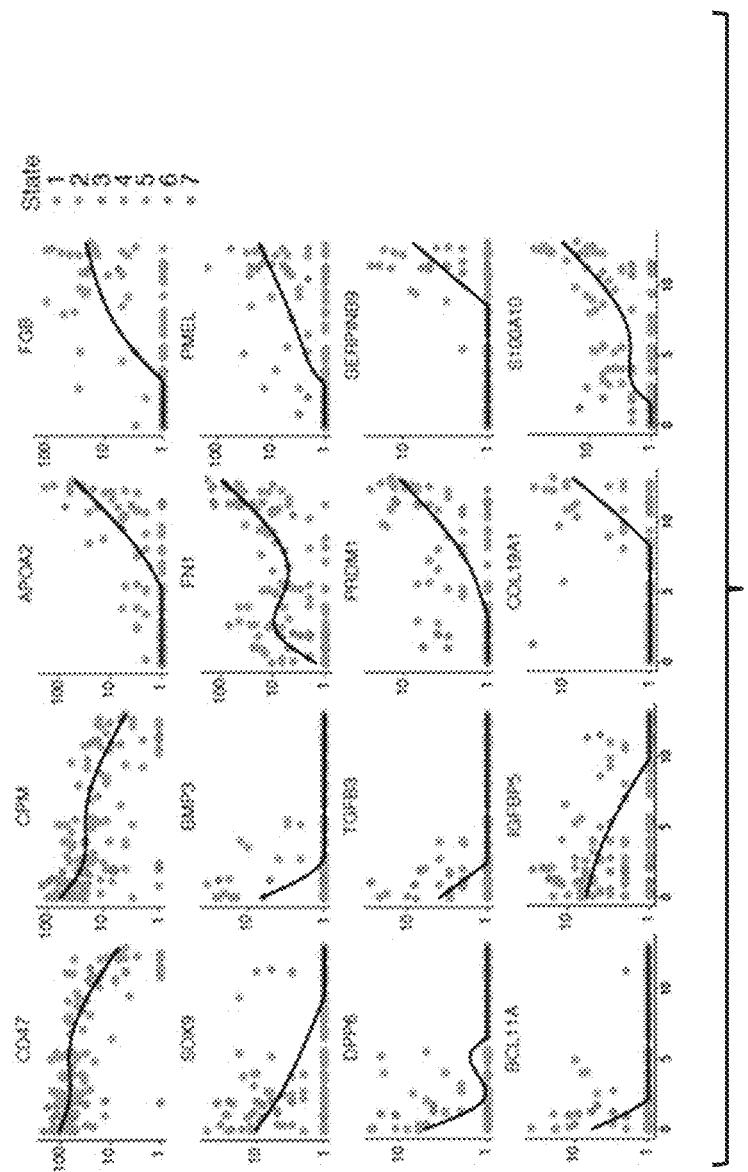
Figure 13A:
FIG. 13A-FIG. 13E Further bioinformatic analysis of cell clusters and differentially expressed genes identified by single cell RNA-seq.

Second, the Monocle computational algorithm was applied (47) to the single cell dataset in an effort to identify, in an unbiased manner and irrespective of cell cycle, cell subtypes or intermediate states. Because a particular challenge in single-cell RNA-Seq experiments is the high cell-to-cell variation observed in most genes, including key developmental regulators, during differentiation (48-51), Monocle was developed to improve the resolution of individual transcriptomes and allow the ordering of cells by potential progress through a biological process without relying on known lineage markers (47). Hence, Monocle was used to order all day 15 cells in pseudotime: an abstract, semi-quantitative measure of progress through a biological process (FIG. 12B). In this analysis, pseudotime represents a computational, high-dimensional ordering of the transcriptional spectrum of differentiating cells, accounting for the likelihood that day 15 cultures contain diverse cell types at various stages of differentiation. In light of the dominant effect of proliferation on the first level analysis (FIG. 6C) cell-cycle genes were excluded from the Monocle analysis. Unsupervised cell clustering revealed 7 Monocle "States" (labeled states 1-7; FIGS. 6E and 12B), composed of 24, 8, 10, 57, 21, 13 and 12 cells, respectively. Next, cells were labeled in each state based on expression levels of NKX2-1 (high vs no/low expression; FIG. 6E) and determined that cells in states 5 and 6 clustered separately because they expressed no or low levels of NKX2-1, whereas cells in state 1, 2, 4 and 7 were almost entirely "NKX2-1 high". In contrast, most states were neither defined by cell cycle effects (mitotic state) nor genetic background (cell origin) of each iPSC line, with the exception of States 5 and 6, which were entirely composed of unsorted BU3 cells, as expected (FIG. 6E). Consistent with FIG. 6C clustered heat map results, States 1, 2, 4 and 7 cells were found to express higher levels of NKX2-1, CD47 and SFTA3 consistent with a lung signature, whereas State 5 cells were enriched for APOA2 and FGB, consistent with a fetal liver signature (FIG. 6, 12D and data not shown). The lineage identity of State 6 cells, enriched for transcription factors including MSX1, EGLN3 and OTX2, was uncertain. The presence of discrete NKX2-1+ states indicated some degree of either temporal or lineage heterogeneity within the overall NKX2-1 population. For example, SOX9 expression varied across cells in CD47+/NKX2-1+ states. State 1 and 2 cells were significantly enriched for SOX9 expression, whereas state 4 cells were not. State 3 cells were highly enriched for SOX9 but expressed lower levels of NKX2-1. Using Monocle to examine genes that follow similar expression trends when cells are ordered in pseudotime genes with increasing expression towards a lung phenotype (including SOX9, NKX2-1, CD47, NFIB, LAMA3, and SFTA3) and conversely genes with increasing expression towards a liver phenotype were identified (DLK1, AFP, MSX1, FTL1, FN1, FGB, and APOA2) (FIGS. 6F and 12C, 12D). The expression of SOX9 at variable but easily detected levels in the majority of NKX2-1+ putative lung cells was confirmed at the protein level by immunostaining (FIG. 6G), and only a minor subset of NKX2-1+ cells expressed high levels of the proximal airway patterning marker SOX2 without SOX9 (either by immunostaining or by supervised hierarchical clustering of single cell transcriptomes; FIG. 13A). This predominance of the distal progenitor marker, SOX9, in day 15 NKX2-1+ cells is consistent with the efficient distal alveolar differentiation competence of the NKX2-1+ progenitor population observed in the "recombinant" cultures in FIG. 3. Importantly, mature distal or proximal markers (e.g., SFTPC and SCGB1A1) were not detected in any cell on day 15 (FIG. 13A).

Figure 13B:
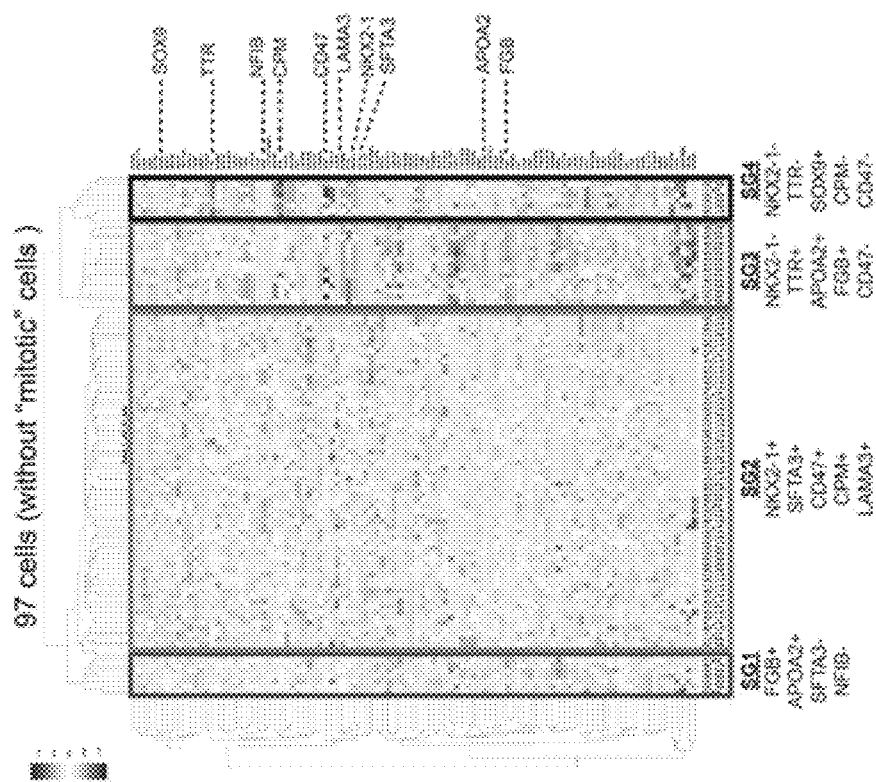
Figure 13D:
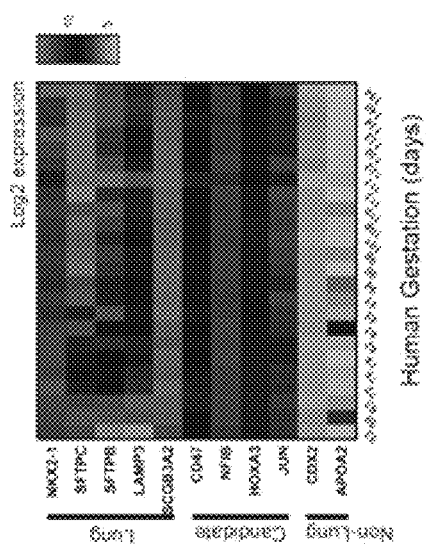
Figure 13C:
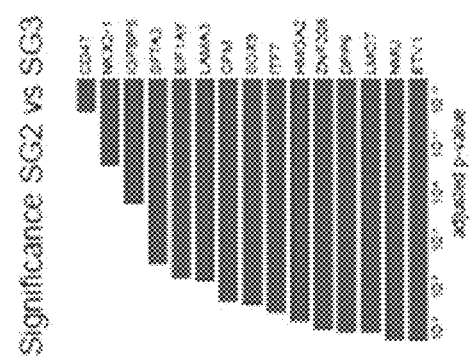

Finally, repeat ANOVA with hierarchical cell and gene clustering of the 97 cells that were not in active mitosis was performed (focusing solely on CC3 and CC4; FIGS. 6C and 13B). This analysis identified four cell subgroups (SG1-SG4; FIG. 13B). The largest subgroup of cells, hereafter SG2, expressed key genes of the early developing lung (SFTA3, NFIB and WNT5A) and, in keeping with the population-based transcriptomic profiles described herein, they lacked detectable expression of markers of lung maturation (SFTPC, SFTPB, SCGB3A2, ASCL1, FOXJ1 or SCGB1A1)(FIG. 13B). In the three remaining minor subgroups (SG1, SG3, and SG) comprising predominantly NKX2-1 negative BU3 cells), differentially expressed genes suggestive of non-lung endoderm or undetermined identity were found. Gene sets most significantly correlated with SG1 and SG3 were consistent with hepatic lineages (FIG. 13B). Significance testing of SG2 vs SG3 demonstrated CD47 was the most highly differentially expressed gene in SG2 (ranked by either p-value or correlation with NKX2-1 expression; FIG. 13C), followed by IGFBP5, SFTA3, EIF1AY, LAMA3, CPM, SOX9, and LMO7 (FIG. 13C). LMO7 is a known target of FGF10 that is upregulated in early developing mouse lung epithelium (52) and NKX2-1, SFTA3, CPM, and SOX9 are all known to be enriched in developing mouse and human lung epithelia.

Figure 13E:
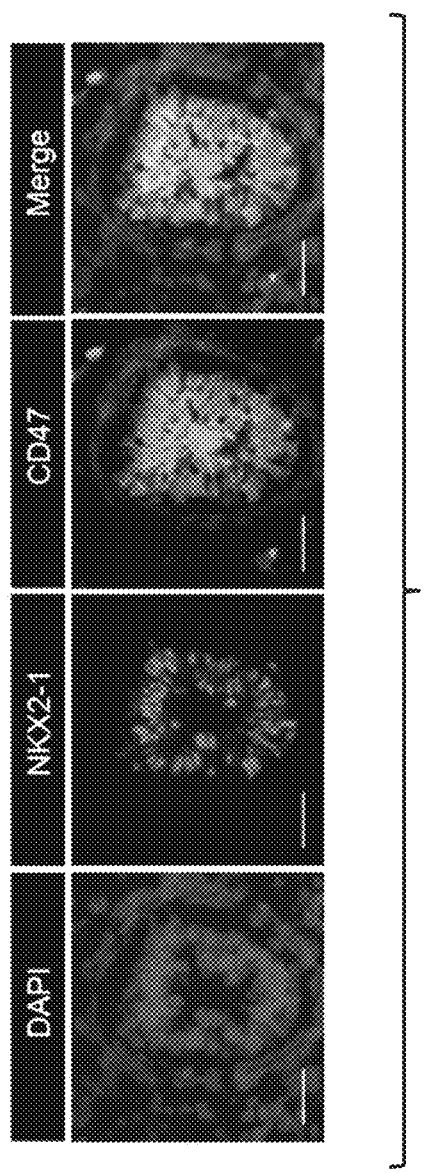

To determine whether key markers identified in the single-cell RNA-Seq or microarray analyses are expressed in the developing human lung epithelium in vivo, available microarray data of human fetal lungs ranging from 53 to 154 days of gestation was analyzed (53). Consistent with the PSC in vitro model system described herein, increasing in vivo expression with time of known lung differentiation markers, SFTPC, SFTPB, and LAMP3), absence at any time point of "non-lung markers," APOA2 and CDX2, and early, unchanging expression of NKX2-1, CD47, NFIB, HOXA3, and JUN (FIG. 13D) was observed. In addition, early developmental CD47 protein expression was confirmed in NKX2-1+ epithelial cells in vivo by immunostaining week 10 human fetal lung (FIG. 13E).

Taken together these results provided an improved understanding of the heterogeneity of iPSC-derived cells emerging with lung directed differentiation, supported the utility of NKX2-1GFP+ sorting to deplete non-lung endodermal lineages that contribute to this heterogeneity, and indicated transcripts associated with NKX2-1+ cells in this in vitro model system.

Figure 7A:
Figures 14A, 14B:
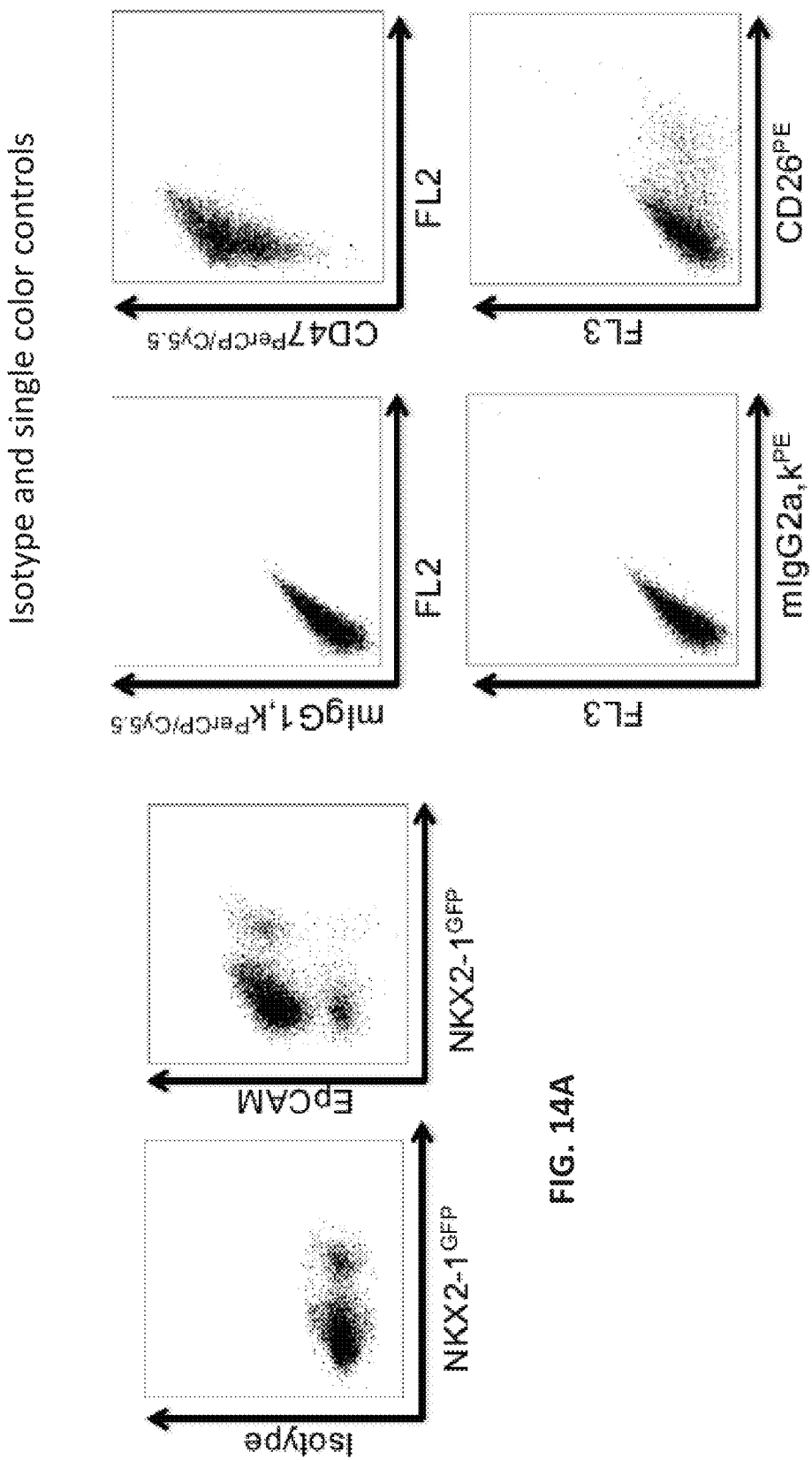
FIG. 14A-FIG. 14E Further cell surface profiling and prospective isolation of iPSC-derived NKX2-1+ primordial lung progenitors by CD47$^{hi}$/CD26$^{lo}$ cell sorting.

Prospective Isolation of iPSC-Derived NKX2-1+ Primordial Lung Progenitors by CD47$^{hi}$ Cell Sorting Because the single cell RNA sequencing profiles revealed that CD47 was the transcript in the genome most highly correlated with NKX2-1 (FIG. 6D), it was sought to determine whether NKX2-1+ primordial progenitor cells could be prospectively isolated based on cell surface protein expression of CD47 without the need for a GFP knock-in reporter. Using both immunofluorescence microscopy as well as FACS of day 13-15 unsorted PSCs (C17, BU3, and RUES2 lines), the brightest CD47+ cells were observed to selectively co-express NKX2-1 nuclear protein as well as the NKX2-1$^{GFP}$ reporter (FIGS. 7A,7B and 14).

Figure 7B:
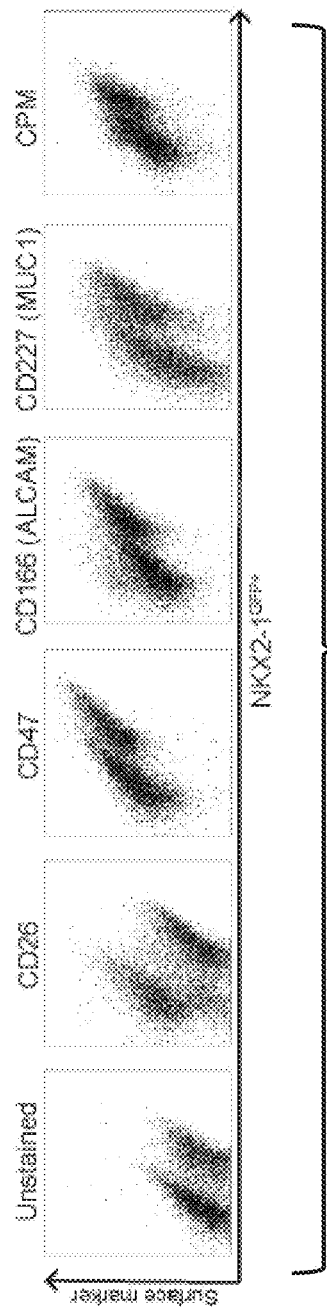
Figure 7G:
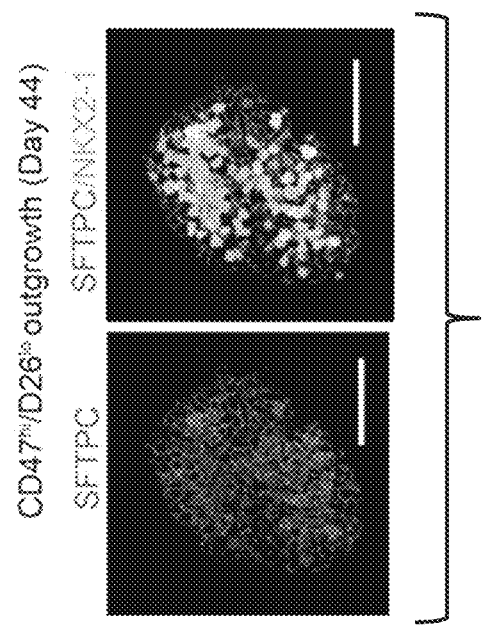
Figure 7F:
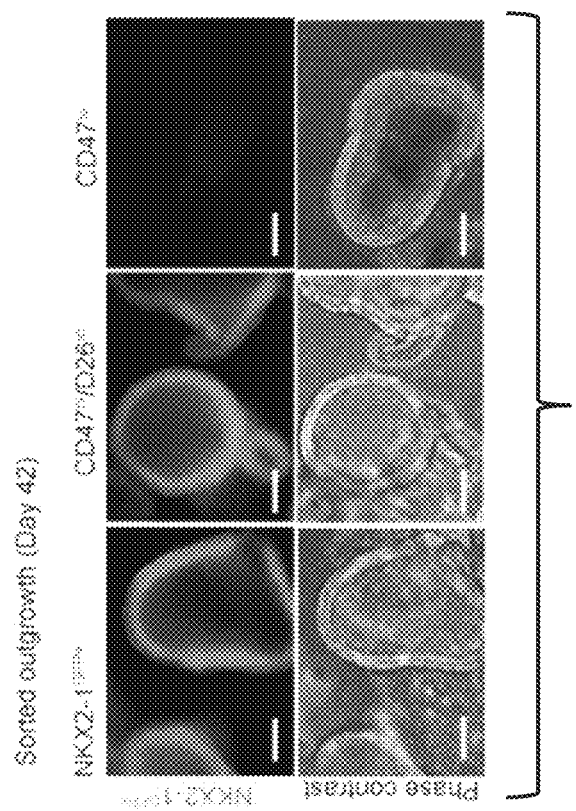
Figure 14C:
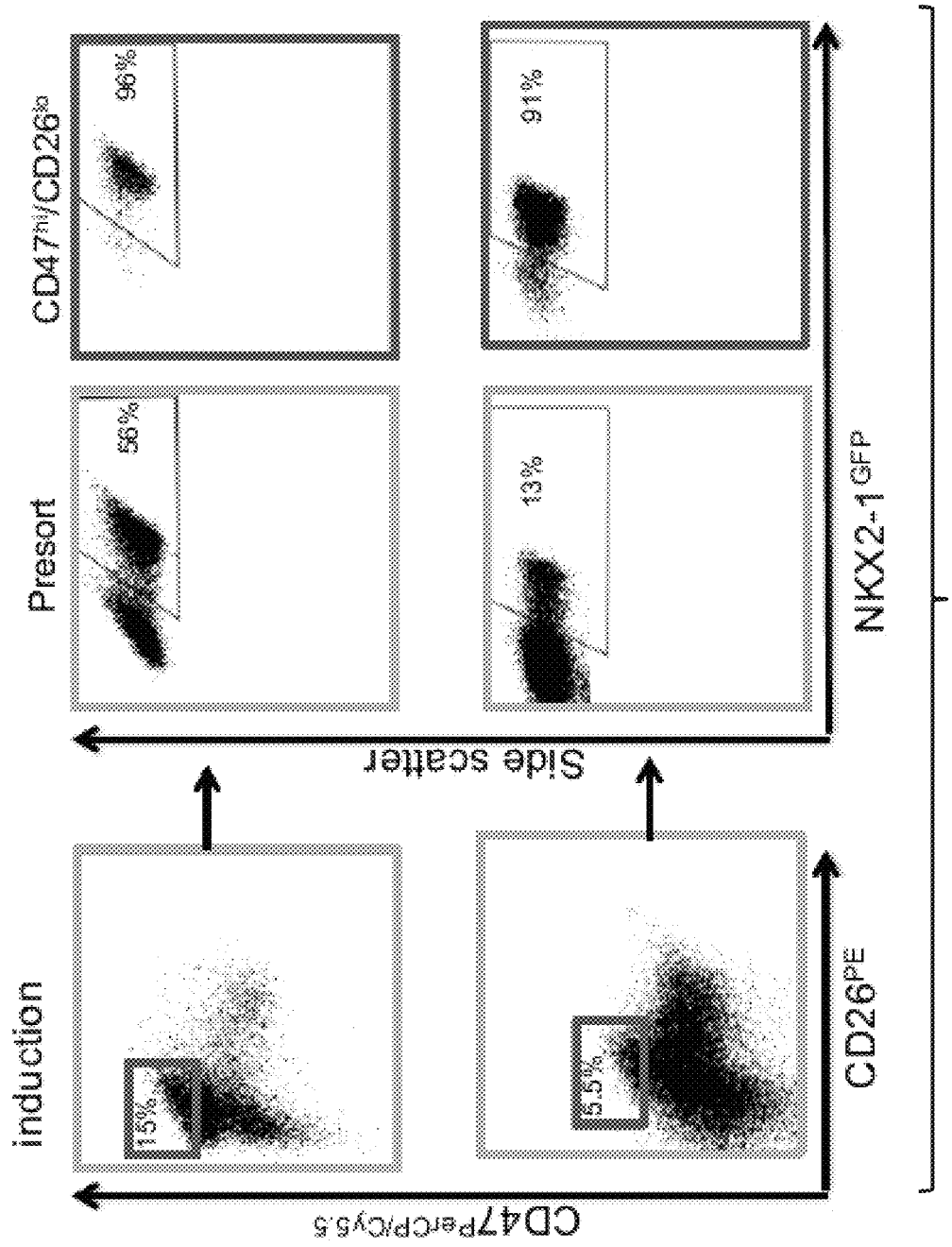
Figures 14D, 14E:
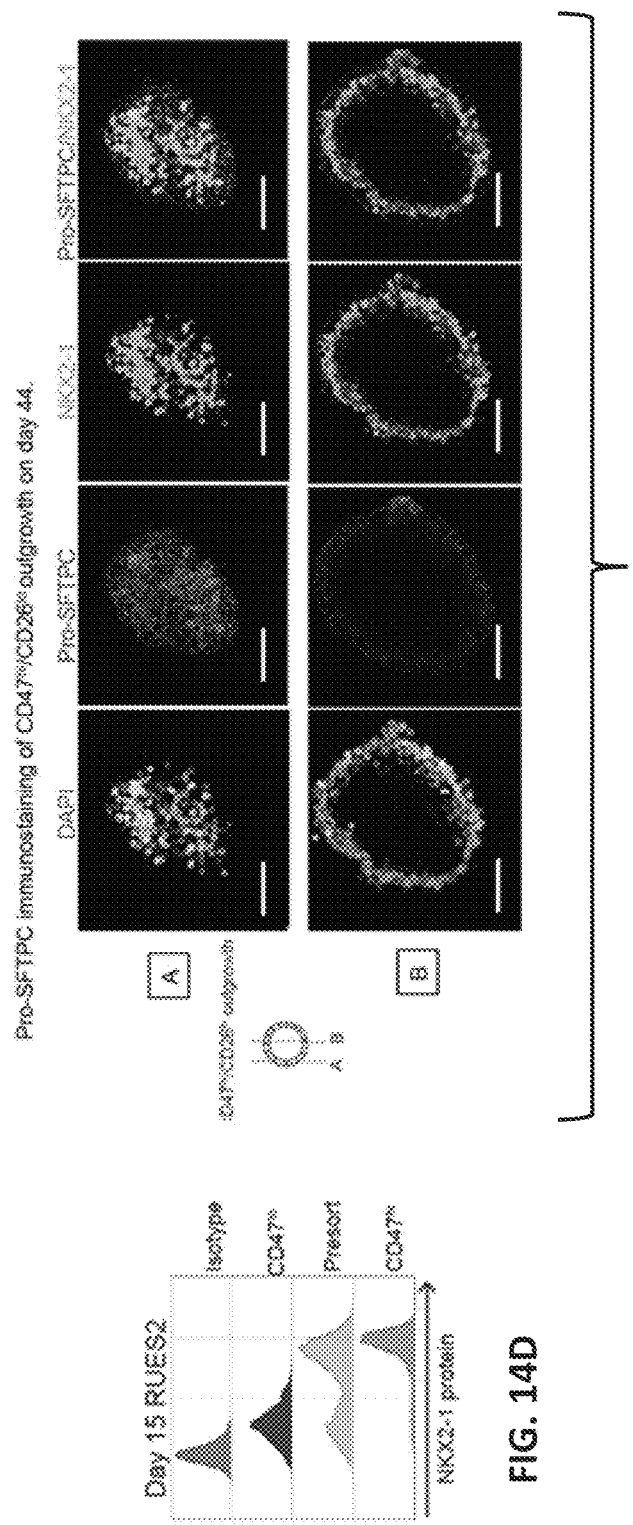

In independent experiments day15 iPSC-derived NKX2-1$^{GFP+}$ progenitors were screened by FACS using a panel of 243 antibodies, validating that CD47 was in the top 4 cell surface markers most associated with GFP+ expression (FIG. 7B). Notably this screen also confirmed that: a) NKX2-1$^{GFP+}$ cells are EPCAM positive (FIG. 14A), b) CPM, recently published as a marker of iPSC-derived NKX2-1+ cells (16) and highly associated with NKX2-1 in the single cell sequencing (FIG. 6D), indeed costains most NKX2-1$^{GFP+}$ cells (FIG. 7B), although it is also associated with NKX2-1− hepatic cells (47) that emerge at low levels in this protocol (FIGS. 6F, 12B, and 13D), and c) ALCAM (CD166), and MUC1 (CD227) are two additional candidate markers that selectively identify NKX2-1$^{GFP+}$ cells at this stage (FIG. 7B). Importantly the antibody screen also identified CD26 as a "negative selection" marker since the brightest CD26+ cells were lower in expression of the NKX2-1$^{GFP}$ reporter (FIG. 7B). When sorting day 13-15 cells based solely on CD47$^{hi}$/CD26$^{lo}$ gating, significant enrichment for NKX2-1+ cells was observed: 89%+/−4.1 of cells (mean±−S.D; n=11 runs) expressed NKX2-1 nuclear protein as well as the NKX2-1$^{GFP}$ reporter compared to CD47$^{lo}$ cells, which were depleted of NKX2-1 expression (FIGS. 7C-7F). These findings were validated for both hESCs (RUES2) as well as multiple iPSC lines (C17, BU3, 100-3, RC202 and RC204 (18, 19, 55 and data not shown) despite varying efficiencies of NKX2-1+ induction in any given differentiation run (FIGS. 14C-14D). For example, regardless of whether a line differentiated to lung with low or high efficiency (e.g., 13% vs. 56% NKX2-1+ in 3 separate runs for C17; or 50% for RUES2), in each case CD47$^{hi}$/CD26$^{lo}$ gating provided significant enrichment in NKX2-1+ cells (7-fold vs. 2-fold enrichment for C17 and 2-fold for RUES2) resulting in populations approximately 90% pure for NKX2-1 expression in each run. Furthermore, hESCs or hiPSCs sorted solely on CD47$^{hi}$/CD26$^{lo}$ gating produced predominantly NKX2-1+ spheroids in 3D culture that expressed lung differentiation markers including pro-SFTPC protein and SFTPC mRNA at levels similar to sorted NKX2-1$^{GFP+}$ cells (FIGS. 7D,7G).

The results shown herein indicate that iPSC-derived lung epithelial cells originate from identifiable NKX2-1+ progenitors. Through the use of a novel NKX2-1 targeted GFP reporter these progenitors can be sorted and then further differentiated without mesenchymal co-culture support in 3D MATRIGEL™ culture. Importantly, human NKX2-1+ progenitors derived with the methods described herein undergo efficient distal SFTPC+ differentiation and proliferation after "recombinant" culture with primary distal embryonic mouse lung mesenchyme. NKX2-1+ cells that emerge between days 8 and 15 of iPSC differentiation are labeled as "primordial progenitors," because they express a transcriptome that includes the earliest transcripts known to emerge during the endodermal and primary lung bud stages of mammalian development (NKX2-1, SFTA3, SOX9, and SOX2) but they are otherwise lacking in transcripts associated with differentiated/maturing lung epithelia, most of which emerge during the later pseudoglandular stage of lung development.

These findings support a paradigm in which the human lung epithelium derives directly from NKX2-1+ endodermal progenitors rather than from alternate cells, because sorting human NKX2-1+ cells at the primordial stage highly enriches for cells competent to further differentiate into lung epithelia, while depleting this population significantly depletes cells competent to form lung. Given the difficulty accessing and tracking live human fetal cells in vivo during the earliest stages of lung development (approximately 1 month of human gestation) the in vitro model described herein enables the purification, tracking, and visualization of cells undergoing the earliest moments of human lung cell fate decisions, a time period in human lung development that remains elusive to scientific study.

Evidence is provided herein that the genetic control of early human lung development is similar to mouse. Indeed, the finding that human iPSC-derived lung epithelial progenitors respond to inductive differentiation cues provided by developing mouse lung mesenchyme indicates that an evolutionarily conserved biology is common to early mouse and human lung development. Furthermore, the stage dependent transcription factor signatures for developing lung, thyroid, and forebrain revealed by the in vitro iPSC model provides important validation in a human system of many of the gene ensembles previously identified in mice. For example, many genes and transcription factors of murine lung development were found to be expressed in iPSC-derived human lung progenitors, including NKX2-1, SHH, FOXA2, FOXA1, GATA6, SOX2, SOX9, GRHL2, IRX1, IRX2, NFIA, NFIB, FOXP2, HNFIB, ELF3 and ELF5. The developmental stage-dependent signatures provided herein also indicate novel genes requiring further study, and the ability to employ the human iPSC model system should now provide a tractable developmental human system to examine the roles of these and other genes in human lung lineage specification. Partnered future work focused on this early period of lung lineage specification in in vivo mice is likely to provide a further understanding of the phenotype and biology of primordial lung progenitors across mammalian species, and should enable isogenic head-to-head comparisons of iPSC-derived progenitors with their in vivo counterparts. It is important to point out that the differentiation kinetics of the human iPSC in vitro model described herein is generally faster than that observed in vivo in developing human endoderm and lungs. Thus, the possibility that cells in the in vitro developmental model take a slightly different or alternate path towards lung cell fates cannot be excluded.

Given the primordial nature of early NKX2-1+ lung progenitors, whether derived from iPSCs/ESCs or emerging in vivo in embryos (2, 56), specific lung progenitor markers have not been previously identified with certainty to enable their prospective isolation. While Foxp2 in mice has been proposed as a lung primordial marker (56) and CPM has been proposed as a cell surface marker for sorting NKX2-1+ cells derived from human iPSCs (16), the previous lack of any available tool for specifically tracking or purifying live NKX2-1+ cells has left uncertainty regarding the specificity of those markers for prospective lung progenitor isolation. The profiling of NKX2-1$^{GFP+}$ primordial progenitors by microarrays, single cell RNA sequencing, and FACS-based screens reveals a cell surface phenotype, CD47$^{hi}$/CD26$^{lo}$, which can be used to prospectively isolate NKX2-1+ progenitors when derived from iPSCs in culture. These findings validate the utility of CPM, recently published by Gotoh et al., to also serve as a cell sorting marker (16), although CPM is also expressed in NKX2-1− hepatic cells which emerge in this lung directed differentiation protocol. While FOXP2 is enriched in the NKX2-1+ progenitor population, the results in this study indicate it lacks lung specificity and is also expressed elsewhere in the protocol, for example, in day 15 NKX2-1− cells (data not shown; Gene Expression Omnibus, GEO Series ID GSE83310).

Like other published markers for the purification of iPSC-derived endoderm (e.g., CKIT/CXCR4) CD47 is broadly expressed in many tissues. However, in the iPSC model system it has particular utility as a marker that allows sorting of NKX2-1+ lung progenitors with ~90% purity based on its unexpectedly high levels of cell surface expression compared to other cells. CD47 is a broadly expressed cell surface glycoprotein with diverse roles in cellular processes including apoptosis, proliferation and migration. The extracellular domain of CD47 acts as a Thrombospondin-1 (TSP-1) receptor but also interacts with integrins and SIRPα (50). CD47 is expressed in lung epithelial cells in vivo and in vitro where it has a role ascribed to regulating leukocyte migration into the lung (51).

Just as the results described herein provide an increased understanding of the level of heterogeneity present in iPSCs undergoing initial lung lineage specification in culture, further work is needed to interrogate the increasing heterogeneity that appears to emerge with each subsequent lung differentiation step. Similar to the NKX2-1$^{GFP+}$ tool used herein, engineering multicolored reporters that become activated in more differentiated lung epithelial lineages should gradually facilitate this understanding and enable purification of subsets of increasingly mature cells in order to understand and overcome this obvious heterogeneity. These approaches will facilitate modulations of later lung differentiation stages in order to efficiently pattern cells into proximal vs. distal lineages and their downstream progeny.

In summary, the inventors have purified human lung progenitors derived from iPSCs, and these cells are reminiscent of early stages of lung developmental differentiation. The profiling of these cells as well as their precursors and progeny during the time course of directed differentiation has resulted in an understanding of their global transcriptomic programs at the single cell level and provides a validated set of cell surface markers and transcription factors selectively enriched in these cells. Now it is possible to test whether cells of similar primordial lung progenitor phenotype remain in the lung post-natally or can be re-derived in patients during responses to injury. Given the broad differentiation repertoire of the primordial progenitors, the inventors anticipate that access to pure populations of these cells should facilitate basic developmental studies as well as clinical applications focused on disease modeling, drug development, and potentially future regenerative therapies.

Experimental Procedures

Human PSC Maintenance and Gene Editing

Previously published PSC lines "iPSC17" (18), "BU3" (19) and WA09 (H9 ESC) were maintained in feeder-free conditions on MATRIGEL™ (Corning) in mTeSR1 (Stem Cell Technologies) and passaged with Gentle Cell Dissociation Reagent (Stem Cell Technologies). All studies using human cells were approved by the institutional review boards of Boston University and the University of Texas Health Science Center. In order to generate NKX2-1$^{GFP}$ reporter PSC lines, Transcription Activator Like Effector Nucleases (TALEN) or CRISPR based technologies were employed to introduce a DNA double stranded break into the second intron of NKX2-1 (FIG. 8A). A donor matrix containing a splice acceptor, NKX2-1 exon 3, 2A-eGFP and loxP-flanked PGK-puroΔTK selection cassette was integrated by homologous recombination and targeted PSC clones resistant to puromycin underwent Cre-mediated excision of the loxP-flanked puroΔTK selection cassette (FIG. 8B, right panel) followed by confirmation of cassette excision, karyotyping and characterization as detailed in the supplement.

Human iPSC Directed Differentiation

Neuroectodermal NKX2-1$^{GFP+}$ cells were generated using STEMDdiff Neural Induction Medium (Stem Cell Technologies) according to the manufacturer's protocol. On day 6 of differentiation, 2 μM of purmorphamine (Stemgent) was added to the base media. NKX2-1+ cells were sorted on Day 12-14. Thyroid NKX2-1$^{GFP+}$ cells were derived using a recently published protocol (18) and lung NKX2-1$^{GFP+}$ cells were generated by adapting published protocols (8, 9). For both lung and thyroid differentiations the definitive endoderm was first induced using STEMDiff definitive endoderm kit (STEMCELL Technologies) according to the accompanying protocol. After approximately 72 to 84 hours cells were harvested and analyzed by flow cytometry for efficiency of definitive endoderm induction by the co-expression of the surface markers C-kit and CXCR4. After definitive endoderm induction cells were plated in small clumps at approximately 50-150,000 cells/cm² on MATRIGEL™-coated plates in complete serum-free differentiation media (CSFDM) supplemented with 2 μM Dorsomorphin (Stemgent), 10 μM SB431542 (Tocris) for 72 hours. 10 μM Y-27632 (Tocris) was added for the first 24 hours. To specify thyroid epithelium, differentiation media was changed on day 6 to CSFDM supplemented with 250 ng/ml rhFGF2

(R&D Systems), 100 ng/ml of rhBMP4 (R&D) and 100 ng/ml Heparin Salt (Sigma) according to published methods (19). To specify lung epithelium, differentiation media was changed on day 6 to "CFKBRa"; CSFDM supplemented with 3 µM CHIR99021 (Tocris), 10 ng/ml rhFGF10, 10 ng/ml rhKGF, 10 ng/ml rhBMP4 (all from R&D Systems), 50-100 nM Retinoic acid (Sigma) (9). Day 15 cells were dissociated with 0.05% trypsin (ThermoFisher Scientific) followed by resuspending as small clumps in CSFDM supplemented with 3 uM CHIR99021, 10 ng/ml rhFGF10 and 10 ng/ml rhKGF ("CFK" media) and plated on freshly-coated MATRIGEL (Corning 354277) plates. 10 µM Y-27632 was added to "CFK" media for the first 24 hours. On day 22 media was changed to "CFK+DCI": "CFK" media plus 50 nM dexamethasone (Sigma), 0.1 mM 8-Bromoadenosine 3',5'-cyclic monophosphate (8-Br-cAMP) sodium salt (Sigma) and 0.1 mM 3-Isobutyl-1-methylxanthine (IBMX) (Sigma).

Sorting iPSC-Derived Lung Progenitors and Organoid Generation

On day 15, live cells identified by propidium iodide (PI) exclusion were sorted by flow cytometry based on GFP expression for downstream applications including RNA analysis and generating organoids. To generate unsorted organoids day 15 cells were dissociated with trypsin and pelleted cells were resuspended in MATRIGEL (Corning 356230). "CFK" media was then added to each well, supplemented with 10 µM Y-27632 media for the first 24 hours. To generate sorted NKX2-1$^{GFP+}$ or NKX2-1$^{GFP-}$ organoids the inventors resuspended the relevant sorted populations in MATRIGEL™ at a density of 50,000 cells per 50-100 µL MATRIGEL™ and allowed to gel as above.

Single Cell RNA-Seq Analysis of Day 15 iPSC-Derived Lung Progenitors

Day 15 NKX2-1$^{GFP+}$ and BU3 unsorted cells were generated using the lung protocol, dissociated and sorted as described above. Fluidigm C1 integrated fluidics circuits (IFCs) were used to capture individual live cells, lyse, convert polyA+RNA into full length cDNA, amplify cDNA and generate cDNA according to the manufacturer's protocol ("Using C1 to Generate Single-Cell cDNA Libraries for mRNA Sequencing", Fluidigm, PN 100-7168). The modified Illumina Nextera XT DNA library preparation protocol was used to prepare bar-coded cDNA libraries, which were sequenced by Elim BioPharm (Oakland, Calif.) on 2 lanes of an Illumin HiSeq Flow cell. In total 570 million 50 bp reads were sequenced for each end and 515 million reads were aligned with an average of 2.8 million reads per cell per end. Aligned, mapped reads were statistically analyzed using methods detailed elsewhere herein. The clustering, PCA and significance testing were performed using SCICAST (details and a walkthrough can be found at github.com/iandriver/SCICAST) with additional hierarchical clustering linkage, Pearson's correlation coefficients, ANOVA and FDR-adjusted p value calculation methods detailed elsewhere herein. Unbiased cell clustering was performed and cells ordered in pseudotime using Monocle 2 (47).

Isolation of Primary Human Fetal Lung Epithelium

Week 10 and 21 human lung tissues were obtained under regulatory oversight of the Institutional Review Board at the Children's Hospital of Philadelphia with subsequent review by Vanderbilt University. "Uncultured naïve distal lung epithelial cells" or primary "differentiated alveolar type 2 (AT2) cells" were then isolated from these tissues in the Guttentag lab using methods detailed in the supplement and previously published (59, 60).

Microarray Analysis

Biological triplicates of all samples except human fetal lung were prepared. Biological duplicates from one embryo ("uncultured naïve lung epithelium") and a singlicate from a different embryo ("differentiated AT2 cells") were prepared for the human fetal lung sample controls. Global gene expression in all 27 samples was analyzed by Affymetrix GeneChip Human Gene 2.0 ST arrays using methods and computational analyses detailed in the supplement. Differential gene expression with respect to experimental group across all samples was assessed by performing a one-way ANOVA with correction for multiple hypothesis testing using the Benjamini-Hochberg false discovery rate (FDR). All raw data gene expression files can be downloaded from the Gene Expression Omnibus, GEP Series ID GSE83310).

Recombination with Mouse Embryonic Lung Mesenchyme

Recombinations were performed essentially as previously described (25). Briefly, small GFP– positive or GFP-negative fragments of day 21 hiPSC organoids were recombined with 10-12 pieces of mouse embryonic day 12 (E12) lung mesenchyme (LgM) manually dissected free of any epithelial as published. The LgM rudiments were teased into close apposition to the human fragments with microsurgery knives (Fine Science Tools, Inc). After overnight culture to promote tissue adherence, the recombinants were transferred to the surface of a 8 µm pore size Whatman nucleopore filter and cultured for 5-7 days in BGJb medium containing 20% FBS, 0.2 mg/ml vitamin C (Sigma), and 5 µg/ml recombinant mouse amino-terminal SHH (R&D Systems) to promote mesenchyme viability (61). The recombinants were maintained for 7 days, with medium changes every other day. Dexamethasone (50 nM) was added to the medium for the final 48 hours to promote lung epithelial differentiation.

Reverse Transcription Quantitative Polymerase Chain Reaction (RT-qPCR)

RNA extracts were converted to cDNA and analyzed during 40 cycles of real time PCR using TAQMAN™ probes (Applied Biosystems). Relative gene expression, normalized to 18S control, was calculated as fold change in 18S-normalized gene expression, over baseline, using the $2^{(-\Delta\Delta CT)}$ method. Unless otherwise specified in the text, baseline, defined as fold change=1, was set to undifferentiated stem cell levels, or if undetected, a cycle number of 40 was assigned to allow fold change calculations.

Immunostaining of Tissue Sections or Cells

For cell immunophenotype screening, the BD Lyoplate Human Cell Surface Marker Screening Panel was used to stain day 15 CFNKX2-1$^{GFP}$ iPSCs followed by flow cytometry analysis for the expression of 242 cell surface markers according the manufacturer's instructions. Immunostaining of paraffin sections of fixed tissues was performed using methods described elsewhere herein, employing antibodies against: NKX2-1 (rabbit monoclonal, Abcam, Ab76013, 1:250), NKX2-1 (mouse monoclonal, Abcam, Ab72876, 1:100), EPCAM (mouse monoclonal, Abcam, GR224588-1, 1:250), GFP (polyclonal chicken IgY, AVES, GFP 1020, 1:10,000), Pro-SPC (polyclonal rabbit, Seven Hills, WRAB-9337, 1:100) and PAX8 (polyclonal rabbit, Abcam, Ab 122944 1:50-1:100).

mRNA In Situ Hybridization and gDNA Southern Blotting

A full-length cDNA encoding human SFTPC was isolated by RT-PCR and cloned into vector pcDNA3, which was then used to transcribe digoxigenin-labeled antisense riboprobe. Whole mount in situ hybridization on tissue recombinants was performed according to the protocol described by Wilkinson (55). Southern blotting of genomic DNA extracts was performed using digoxigenin (DIG)-labeled hybridization probes as described herein.

REFERENCES

1. Kimura S et al. The T/ebp null mouse: thyroid-specific enhancer-binding protein is essential for the organogenesis of the thyroid, lung, ventral forebrain, and pituitary. Genes & Development 1996; 10(1):60-69.
2. Lazzaro D, Price M, de Felice M, Di Lauro R. The transcription factor TTF-1 is expressed at the onset of thyroid and lung morphogenesis and in restricted regions of the foetal brain. Development 1991; 113(4):1093-1104.
3. Minoo P, Su G, Drum H, Bringas P, Kimura S. Defects in tracheoesophageal and lung morphogenesis in Nkx2.1 (−/−) mouse embryos. Dev Biol 1999; 209(1):60-71.
4. Coraux C et al. Embryonic stem cells generate airway epithelial tissue. Am J Respir Cell Mol Biol 2005; 32(2): 87-92.
5. Wang D, Haviland D L, Burns A R, Zsigmond E, Wetsel R A. A pure population of lung alveolar epithelial type II cells derived from human embryonic stem cells. Proc Natl Acad Sci USA 2007; 104(11):4449-4454.
6. Van Haute L, De Block G, Liebaers I. Generation of lung epithelial-like tissue from human embryonic stem cells 2009;
7. Green M D et al. Generation of anterior foregut endoderm from human embryonic and induced pluripotent stem cells. Nat. Biotechnol. 2011; 29(3):267-272.
8. Longmire T A et al. Efficient derivation of purified lung and thyroid progenitors from embryonic stem cells. Cell Stem Cell 2012; 10(4):398-411.
9. Huang S X L et al. Efficient generation of lung and airway epithelial cells from human pluripotent stem cells. Nat. Biotechnol. 2014; 32(1):84-91.
10. Firth A L et al. Generation of multiciliated cells in functional airway epithelia from human induced pluripotent stem cells. Proceedings of the National Academy of Sciences 2014; 201403470.
11. Mou H et al. Generation of multipotent lung and airway progenitors from mouse ESCs and patient-specific cystic fibrosis iPSCs. Cell Stem Cell 2012; 10(4):385-397.
12. Hawkins F, Rankin S A, Kotton D N, Zorn A M. The Genetic Programs Regulating Embryonic Lung Development and Induced Pluripotent Stem Cell Differentiation. In: Fetal and Neonatal Lung Development. Cambridge University Press; 2016:1-20
13. Hawkins F, Kotton D N. Embryonic and induced pluripotent stem cells for lung regeneration. Ann Am Thorac Soc 2015; 12 Suppl 1(Supplement 1):S50-3.
14. Wong A P et al. Directed differentiation of human pluripotent stem cells into mature airway epithelia expressing functional CFTR protein. Nat. Biotechnol. 2012; 30(9):876-882.
15. Dye B R et al. In vitro generation of human pluripotent stem cell derived lung organoids. Elife 2015; 4:1999.
16. Gotoh S et al. Generation of Alveolar Epithelial Spheroids via Isolated Progenitor Cells from Human Pluripotent Stem Cells. Stem Cell Reports 2014; 3(3):394-403.
17. Goulburn A L et al. A targeted NKX2.1 human embryonic stem cell reporter line enables identification of human basal forebrain derivatives. STEM CELLS 2011; 29(3):462-473.
18. Crane A M et al. Targeted Correction and Restored Function of the CFTR Gene in Cystic Fibrosis Induced Pluripotent Stem Cells. Stem Cell Reports 2015; 4(4): 569-577.
19. Kurmann A A et al. Regeneration of Thyroid Function by Transplantation of Differentiated Pluripotent Stem Cells. Cell Stem Cell 2015; 17(5):527-542.
20. Kim J-E et al. Investigating synapse formation and function using human pluripotent stem cell-derived neurons. Proceedings of the National Academy of Sciences 2011; 108(7):3005-3010.
21. Ma L et al. Human embryonic stem cell-derived GABA neurons correct locomotion deficits in quinolinic acid-lesioned mice. Cell Stem Cell 2012; 10(4):455-464.
22. Rishniw M et al. Molecular aspects of esophageal development. Annals of the New York Academy of Sciences 2011; 1232(1):309-315.
23. Shannon J M, Hyatt B A. Epithelial-mesenchymal interactions in the developing lung. Annu. Rev. Physiol. 2004; 66(1):625-645.
24. Shannon J M. Induction of alveolar type II cell differentiation in fetal tracheal epithelium by grafted distal lung mesenchyme. Dev Biol 1994; 166(2):600-614.
25. Shannon J M, Nielsen L D, Gebb S A, Randell S H. Mesenchyme specifies epithelial differentiation in reciprocal recombinants of embryonic lung and trachea. Dev Dyn 1998; 212(4):482-494.
26. Herriges J C et al. Genome-scale study of transcription factor expression in the branching mouse lung. Dev. Dyn. 2012; 241(9):1432-1453.
27. Maeda Y, Davé V, Whitsett J A. Transcriptional control of lung morphogenesis. Physiol. Rev. 2007; 87(1):219-244.
28. Millien G et al. Characterization of the mid-foregut transcriptome identifies genes regulated during lung bud induction. Gene Expr. Patterns 2008; 8(2):124-139.
29. Vukicevic S, Helder M N, Luyten F P. Developing human lung and kidney are major sites for synthesis of bone morphogenetic protein-3 (osteogenin). J Histochem Cytochem 1994; 42(7):869-875.
30. Takahashi H, Ikeda T. Transcripts for two members of the transforming growth factor-beta superfamily BMP-3 and BMP-7 are expressed in developing rat embryos. Dev Dyn 1996; 207(4):439-449.
31. Keegan C E et al. Differential expression of corticotropin-releasing hormone in developing mouse embryos and adult brain. 1994; 134(6):2547-2555.
32. Emanuel R L, Torday J S, Asokananthan N, Sunday M E. Direct effects of corticotropin-releasing hormone and thyrotropin-releasing hormone on fetal lung explants. Peptides 2000; 21(12):1819-1829.
33. Simard M, Côté M, Provost P R, Tremblay Y. Expression of genes related to the hypothalamic-pituitary-adrenal axis in murine fetal lungs in late gestation. Reprod. Biol. Endocrinol. 2010; 8(1):134.
34. Provost P R, Tremblay Y. Genes involved in the adrenal pathway of glucocorticoid synthesis are transiently expressed in the developing lung. 2005; 146(5):2239-2245.
35. Herriges M J et al. Long noncoding RNAs are spatially correlated with transcription factors and regulate lung development. Genes Dev. 2014; 28(12):1363-1379.
36. Herriges M, Morrisey E E. Lung development: orchestrating the generation and regeneration of a complex organ. Development 2014; 141(3):502-513.
37. Williams M C. Alveolar type I cells: molecular phenotype and development. Annu. Rev. Physiol. 2003; 65(1): 669-695.
38. Zorn A M, Wells J M. Vertebrate endoderm development and organ formation. Annu Rev Cell Dev Biol 2009; 25(1):221-251.

39. Rankin S A, Kormish J, Kofron M, Jegga A, Zorn A M. A gene regulatory network controlling hhex transcription in the anterior endoderm of the organizer. Dev Biol 2011; 351(2):297-310.
40. Perkins A S, Mercer J A, Jenkins N A, Copeland N G. Patterns of Evi-1 expression in embryonic and adult tissues suggest that Evi-1 plays an important regulatory role in mouse development. Development 1991; 111(2): 479-487.
41. Attar M A et al. Induction of ICAM-1 expression on alveolar epithelial cells during lung development in rats and humans. Exp. Lung Res. 1999; 25(3):245-259.
42. Li Y, Linnoila R I. Multidirectional differentiation of Achaete-Scute homologue-1-defined progenitors in lung development and injury repair. Am J Respir Cell Mol Biol 2012; 47(6):768-775.
43. Metzger D E, Xu Y, Shannon J M. Elf5 is an epithelium-specific, fibroblast growth factor-sensitive transcription factor in the embryonic lung. Dev Dyn 2007; 236(5): 1175-1192.
44. Lu M M, Li S, Yang H, Morrisey E E. Foxp4: a novel member of the Foxp subfamily of winged-helix genes co-expressed with Foxp1 and Foxp2 in pulmonary and gut tissues. Mech. Dev. 2002; 119 Suppl 1:S197-202.
45. Yu Y et al. Gene expression profiling in human fetal liver and identification of tissue- and developmental-stage-specific genes through compiled expression profiles and efficient cloning of full-length cDNAs. Genome Res. 2001; 11(8): 1392-1403.
46. Wilson A A et al. Emergence of a stage-dependent human liver disease signature with directed differentiation of alpha-1 antitrypsin-deficient iPS cells. Stem Cell Reports 2015; 4(5):873-885.
47. Trapnell C et al. The dynamics and regulators of cell fate decisions are revealed by pseudotemporal ordering of single cells. Nat. Biotechnol. 2014; 32(4):381-386.
48. Shalek A K et al. Single-cell transcriptomics reveals bimodality in expression and splicing in immune cells. Nature 2013; 498(7453):236-240.
49. Guo G et al. Resolution of cell fate decisions revealed by single-cell gene expression analysis from zygote to blastocyst. Dev Cell 2010; 18(4):675-685.
50. Tang F et al. Tracing the derivation of embryonic stem cells from the inner cell mass by single-cell RNA-Seq analysis. Cell Stem Cell 2010; 6(5):468-478.
51. Buganim Y et al. Single-cell expression analyses during cellular reprogramming reveal an early stochastic and a late hierarchic phase. Cell 2012; 150(6): 1209-1222.
52. Lü J, Izvolsky K I, Qian J, Cardoso W V. Identification of FGF10 targets in the embryonic lung epithelium during bud morphogenesis. J. Biol. Chem. 2005; 280(6):4834-4841.
53. Kho A T et al. Transcriptomic analysis of human lung development. Am. J. Respir. Crit. Care Med. 2010; 181 (1):54-63.
54. Kido T et al. CPM Is a Useful Cell Surface Marker to Isolate Expandable Bi-Potential Liver Progenitor Cells Derived from Human iPS Cells. Stem Cell Reports 2015; 5(4):508-515.
55. Somers A et al. Generation of transgene-free lung disease-specific human induced pluripotent stem cells using a single excisable lentiviral stem cell cassette. STEM CELLS 2010; 28(10):1728-1740.
56. Sherwood R I, Chen T-Y A, Melton D A. Transcriptional dynamics of endodermal organ formation. Dev Dyn 2009; 238(1):29-42.
57. Barclay A N, Van den Berg T K. The Interaction Between Signal Regulatory Protein Alpha (SIRP α) and CD47: Structure, Function, and Therapeutic Target. Annu. Rev. Immunol. 2014; 32(1):25-50.
58. Herold S et al. Alveolar epithelial cells direct monocyte transepithelial migration upon influenza virus infection: impact of chemokines and adhesion molecules. J. Immunol. 2006; 177(3): 1817-1824.
59. Wade K C et al. Gene induction during differentiation of human pulmonary type II cells in vitro. Am J Respir Cell Mol Biol 2006; 34(6):727-737.
60. Gonzales L W, Guttentag S H, Wade K C, Postle A D, Ballard P L. Differentiation of human pulmonary type II cells in vitro by glucocorticoid plus cAMP. Am. J. Physiol. Lung Cell Mol. Physiol. 2002; 283(5):L940-51.
61. Weaver M, Batts L, Hogan B L M. Tissue interactions pattern the mesenchyme of the embryonic mouse lung. Dev Biol 2003; 258(1):169-184.
62. Wilkinson D G. In situ Hybridization. A Practical Approach. Edited by D. G. Wilkinson. IRL Press, Oxford. 1992. 163 pages. £18.50 Softback. ISBN 0 19 963327 4. In: Wilkinson D G ed. Whole mount in situ hybridization of vertebrate embryo. Oxford University Press; 1992:75-83

Supplemental Experimental Procedures

Human iPSC Derivation and Maintenance

The iPSC line "C17" was generated from a patient with cystic fibrosis as previously described (Crane et al. (2015) *Stem Cell Reports* 4:569-577). "BU3" iPSC line was generated from the peripheral blood of a normal donor according to published methods (Kurmann et al. (2015) *Cell Stem Cell* 17:527-542). WA09 (H9) ESC was obtained from WiCell (Madison, Wis.). iPSCs were initially maintained on a feeder layer of mitomycin-inactivated mouse embryonic fibroblasts in human iPSC media (WiCell feeder-dependent protocol) and subsequently transitioned to feeder free conditions on MATRIGEL™ (Corning) in mTeSR1 (Stem Cell Technologies) and passaged with Gentle Cell Dissociation Reagent (Stem Cell Technologies).

Generating a Fluorescent Reporter by CRISPR- or TALEN-Targeting the NKX2-1 Locus.

NXK2-1$^{GFP+}$ iPSC: Transcription Activator Like Effector Nucleases (TALEN), with left TAL effector DNA-binding sequence TCGAGCGCCCGGCCCGG (SEQ ID NO: 2) and right TAL effector DNA-binding domain AGTCTGGGCAGGTGGGA (SEQ ID NO: 3), were designed by Cellectis to introduce a DNA double stranded break into the second intron of NKX2-1 at a site at least 50 bp distant from any known SNPs in either human iPSC (C17) or ES line (WA09) (FIG. 8A). CRISPR-mediated introduction of a DNA double strand break in this same region in BU3 iPSCs was engineered by designing a guide RNA of sequence GCCCTCTCTCCAGCGGAGTC (SEQ ID NO: 4) delivered through transfection of a plasmid encoding a Pol II-driven Cas9 (pSpCas9(BB)-2A-GFP; Addgene, PX458) as well as the Pol III-driven gRNA (pU6-gRNA; Sigma). Detection of error-prone non-homologous end joining (NHEJ) after TALEN-introduced or CRISPR introduced DNA break resulted in cleavage efficiencies of up to 24% in C17 iPSCs and 27% in WA09 determined by Surveyor nuclease assay (Integrated DNA Technologies) (data not shown). A donor matrix containing a splice acceptor, NKX2-1 exon 3, 2A-eGFP and loxP-flanked PGK-puroΔTK selection cassette was integrated by homologous recombination (in the presence of either TALEN or CRISPR based targeting). Targeted, puromycin-resistant clones were obtained after co-electroporation of TALEN expression plasmids and delivery of the targeting donor vector using AMAXAS NUCLEOFECTOR™ (Lonza). Isolated clones were confirmed by a total of four different PCRs spanning 5'-3' and 3'-5' junctions between genomic DNA and donor matrix sequences or vice versa (FIG. 8B, left panel). A unique PCR using primers 5 and 5-1' was capable of binding to both the targeted and unmodified allele, amplifying a smaller and larger DNA fragment, respectively. Successful targeting was achieved in 1 out of 5 screened C17 iPSC, 10 out of 176 WA09 ESC, and 2 out 3 BU iPSC clones, including donor integration into both alleles and the generation of homozygous NKX2-1$^{GFP}$ clones in both ESC/iPSC lines. Cre-mediated excision of the loxP-flanked puroΔTK selection cassette was confirmed by negative selection with FIAU, puromycin selection and PCR analysis (FIG. 8B, right panel). Three homozygous targeted NKX2-1$^{GFP+}$ ESC/iPSC reporter lines showed normal karyotype when analyzed at the Clinical and Research Cytogenetic Laboratory at the Texas Children's Hospital, Houston, Tex. (FIG. 8D). Both targeted lines expressed pluripotency markers SSEA4, OCT-4, NANOG and SOX2 (Stemflow Human Pluripotent Stem Cell Transcription Factor Analysis Kit) (FIG. 8E). Appropriate FITC mouse anti-human SSEA-4 (clone MC813-70) and FITC Mouse IgG3, kappa isotype (all BD Biosciences) were used as controls (FIG. 8E).

Human iPSC Directed Differentiation

Neuroectodermal NKX2-1$^{GFP+}$ cells were generated using STEMDIFF™ Neural Induction Medium (STEMCELL Technologies) according to the manufacturer's protocol. On day 6 of differentiation, 2 µM of purmorphamine (Stemgent) was added to the base media. NKX2-1+ cells were sorted on Day 12-14. Thyroid NKX2-1GFP$^+$ cells were derived using a recently published protocol[2] lung NKX2-1GFP$^+$ cells were generated by adapting published protocols[3,4]. For both lung and thyroid differentiations definitive endoderm was first induced using STEMDIFF™ definitive endoderm kit (STEMCELL Technologies) according to the accompanying protocol. After 72 to 84 hours, as indicated in the results text, cells were harvested and analyzed by flow cytometry for efficiency of definitive endoderm induction by the co-expression of the surface markers CKIT (APC-conjugated mouse monoclonal antibody, Life Technologies CD11705) and CXCR4 (PE-conjugated mouse monoclonal antibody Life Technologies MHCXCR404) with appropriate APC (Life Technologies MG105) and PE (Life Technologies MG204) isotype controls and for intracellular endodermal markers SOX17 (APC goat anti-human SOX17, R&D Systems IC1924A) and FOXA2 (Alexa Fluor 488 goat anti-human FOXA2, R&D Systems IC2400G) with appropriate APC (R&D Systems IC108A) and Alexa Fluor 488 (R&D Systems, IC108G) isotype controls, respectively. After definitive endoderm induction cells were plated in small clumps at 50,000-150,000 cells/cm$^2$ on MATRIGEL™-coated plates in complete serum-free differentiation media (CSFDM) supplemented with 2 µM Dorsomorphin (Stemgent), 10 µM SB431542 (Tocris) for 72 hours. 10 µM Y-27632 (Tocris) was added for the first 24 hours. CSFDM was composed of 375 ml IMDM (ThermoFisher Scientific, 12440-053), 125 ml Ham's F12 (Corning Cellgro, 10-080-CV), 50 µg/ml Ascorbic acid (Sigma, A4544), 5 ml B27 supplement (ThermoFisher Scientific, 12587-044), 2.5 ml N2 supplement (ThermoFisher Scientific, 17502-048), 3.75 ml bovine serum albumin (ThermoFisher Scientific, 15260-037), 5 ml GLUTAMAX™ (ThermoFisher Scientific, 35050061) 0.02 µl monothioglycerol (Sigma, M6145) and 100 g/ml Primocin (Invivogen). To specify thyroid epithelium, differentiation media was changed on day 6 to CSFDM supplemented with 250 ng/ml rhFGF2 (R&D Systems), 100 ng/ml of rhBMP4 (R&D) and 100 ng/ml Heparin Salt (Sigma) according to recently published methods[2]. To specify lung epithelium, differentiation media was changed on day 6 to "CFKBRa"; CSFDM supplemented with 3 µM CHIR99021 (Tocris), 10 ng/ml rhFGF10, 10 ng/ml rhKGF, 10 ng/ml rhBMP4 (all from R&D Systems), 50-100 nM Retinoic acid (Sigma)[4]. Day 15 cells were dissociated by incubating in 0.05% trypsin (ThermoFisher Scientific) at 37° C. for 2-4 minutes, aspirating trypsin, washing once with DMEM (ThermoFisher Scientific)+10% FBS (ThermoFisher Scientific), resuspending as small clumps in CSFDM supplemented with 3 uM CHIR99021, 10 ng/ml rhFGF10 and 10 ng/ml rhKGF ("CFK" media) and plated on freshly-coated MATRIGEL™ (Corning 354277) plates. 10 µM Y-27632 was added to "CFK" media for the first 24 hours. On day 22 media was changed to "CFK+DCI": "CFK" media plus 50 nM dexamethasone (Sigma), 0.1 mM 8-Bromoadenosine 3',5'-cyclic monophosphate (8-Br-cAMP) sodium salt (Sigma) and 0.1 mM 3-Isobutyl-1-methylxanthine (IBMX) (Sigma).

Sorting iPSC-Derived Lung Progenitors

On day 15, cells were sorted for downstream applications including RNA analysis and generating organoids. Day 15 cells were washed with CSFDM and incubated in 0.05% trypsin at 37° C. for 12 to 18 minutes then gently triturated and inactivated with 10% FBS in DMEM. The resulting cell suspension was centrifuged at 200×g for 5 min and re-suspended in FACS Buffer: Hanks Balanced Salt Solution (Life Technologies 14175-079), 2% FBS, 25 mM HEPES (Life Technologies 15630), 2 mM EDTA (Sigma E7889-100 ml), 100 µg/ml Primocin (Invivogen), 10 µM y-27632 (Tocris 1254). The suspension was filtered twice through 40 um filters (Falcon 352340). For CD47/CD26 staining 1×10$^6$ cells in 100 µL were incubated in CD47-PerCP/Cy5.5 (mouse monoclonal, Biolegend, B191878, 1:200) and CD26-PE (mouse monoclonal, Biolegend, 302706, 1:200) or isotype controls (PE mouse IgG1 isotype, Biolegend, 400113 and PerCP/Cy5-5 mouse IgG1 isotype, Biolegend, 400149) for 30 min on ice. Cells were then washed in FACS buffer, centrifuged at 200×g for 5 min and re-suspended in FACS Buffer. Live cells were sorted by staining with propidium iodide (PI) (Life Technologies p3566) and excluding PI+ events or in the case of CD47/CD26 staining with calcein blue (ThermoFisher Scientific, C1429). Cells were sorted into FACS buffer. Sorting was performed on a Mo-Flo Legacy in the BU Flow Cytometry Core.

Generating Organoids

To generate unsorted organoids day 15 cells were dissociated with 0.05% trypsin for 2 to 4 min. Trypsin was aspirated and the cells were washed with DMEM+10% FBS, re-suspended as clumps in CSFDM in a 1.5 ml Eppendorf tube and centrifuged at 200G for 5 min. The Eppendorf was then placed on ice, the supernatant aspirated and the cell pellet resuspended in MATRIGEL™ (Corning 356230). 40-50 uL of MATRIGEL™ was then pipetted into the center of each well of a 12 well tissue culture plate and allowed to gel in the incubator for 15 to 20 min. "CFK" media was then added to each well, supplemented with 10 µM Y-27632 media for the first 24 hours. To generate sorted NKX2-1$^{GFP+}$ or NKX2-1$^{GFP-}$ organoids the relevant sorted populations were resuspended in MATRIGEL™ at a density of 50,000 cells per 50 µL MATRIGEL™ and allowed to gel as above.

Fluidigm Single Cell Analysis of Day 15 iPSC-Derived Lung Progenitors

Day 15 NKX2-1$^{GFP+}$ and BU3 unsorted cells were generated using the lung protocol, dissociated and sorted as described above. Fluidigm C1 and C1 integrated fluidics circuits (IFCs) were used to capture live cells, lyse, convert polyA+RNA into full length cDNA, amplify cDNA and generate cDNA according to their detailed protocol ("Using C1 to Generate Single-Cell cDNA Libraries for mRNA Sequencing", Fluidigm, PN 100-7168). 69/96 NKX2-1$^{GFP+}$ cells were captured on IFC #1 and 84/96 BU3 cells were captured on IFC #2. Library preparation for sequencing was performed following the modified Illumina Nextera XT DNA library preparation protocol. The concentration of cDNA was determined using Quant-iT™ PicoGreen® dsDNA Assay Kit (Life Technologies). Sequencing was performed by Elim BioPharm (Oakland, Calif.) on 2 lanes of an Illumina HiSeq Flow cell. In total 570 million 50 bp reads were sequenced for each end.

Bioinformatics and Statistics:

For the single-cell Seq analysis sequenced reads were aligned and mapped using Tophat (v2.1.0) and Bowtie2 (v2.2.6) and Cufflinks (v2.2.1) software[5,6]. 515 million reads were aligned with an average of 2.8 million reads per cell per end. All of the accepted hits in bam files output from cufflinks were processed using Picard tools (broadinstitute.github.io/picard/) FixMateInformation and then counts were compiled using HTSeq-count¶ using the UCSC hg19 human assembly. All of the gene counts for each cell were compiled into a single file. Filtering was then performed to remove any cell that did not have at least a 50% alignment rate. Genes that did not have a least one read aligned in at least 3 cells were removed. The resulting cell/gene matrix file was then normalized using DESeq2. The clustering, PCA and significance testing were performed using SCI-CAST (details and a walkthrough can be found at github.com/iandriver/scicast). Hierarchical clustering linkage method was performed using the Ward variance minimization algorithm and the distance was computed using the standardized Euclidean distance. All correlation coefficients are Pearson's correlation coefficients, 2-tailed p-values. P-values were computed using one way ANOVA and adjusted p-values were calculated using the R package p.adjust(stat.ethz.ch/R-manual/R-devel/library/stats/html/p.adjust.html) using the Benjamini & Hochberg (1995) "FDR" method.

Monocle Analysis:

Using the software package Monocle (v2.2) cell data was tabulated as follows: CellOrigin was assigned to the respective cells by cell line (C17 or BU3). NKX2-1 level was assigned as "High" or "No/low" expression based on a simple cutoff where all cells with an NKX2-1 expression value of 10 or more were assigned NKX2-1 "High" and all others were assigned NKX2-1 "No/low". The three mitosis categories were assigned based on the unbiased clustering of all cells and all genes (see FIG. 13C). The full code and data for recreating the analysis can be found at github.com/iandriver/ips17-BU3-single-cell. Cells were filtered on number of mRNAs expressed and genes were filtered on both the sum expression of that gene (>80 across all 145 cells) and the number of cells that expressed a given gene at any level above 0 (>6 cells with non-zero expression). 145 cells and 12837 genes were present in the final Monocle analysis. Ordering genes were selected in an unbiased fashion using scicast k-means clustering and significance testing functions. The PCA plot of cells served as input to the scikit-learn Kmeans function for two clusters. All of the genes in the two clusters were then compared in using a one-way ANOVA test. The p-values were then adjusted using the Benjamini & Hochberg "FDR" method. Genes were then ranked by FDR-adjusted p-value and the top 200 genes were used as ordering genes for the Monocle package.

Isolation of Human Fetal Lung Epithelium

Week 10 or 21 human lung tissues were obtained under protocols originally reviewed by the Institutional Review Board at the Children's Hospital of Philadelphia and subsequently reviewed by Vanderbilt University. "Uncultured naïve lung epithelial cells" were isolated by the overnight culture of lung explants in Waymouth media; a technique that generally yields 86±2% epithelial cells with the remaining cells consisting of fibroblasts with <1% endothelial cells[7]. "Differentiated alveolar type 2 (AT2) cells" were prepared in a similar manner except that the lung explants were first cultured for 6 days in Waymouth media supplemented with 10 nM Dexamethasone, 0.1 mM 8-Br-cAMP, and 0.1 mM 3-isobutyl-1-1methylxanthine[8]. The method for isolating the AT2 cells was modified in the following way. After initial digestion using Collagenase and DNase as previously described, cells were filtered, rinsed in PBS, and centrifuged at 1200 RPM for 4 minutes at room temperature. Cells were then digested in 15 mL of PBS supplemented with 2 mL Dispase with 160 ul DNase for 30 min at room temperature with magnetic stirring, and the cells were then filtered through a 40 μm filter. Adherence to plastic for removal of fibroblasts was conducted as previously described[7,8]. This resulted in a more enriched population of epithelial cells (90-95%) with the remaining cells being exclusively fibroblasts. Assessment of cell purity by immunostaining of plated cells has been described previously[7,8]. For long-term storage in liquid nitrogen cells were frozen in DMEM supplemented with 10% by volume of DMSO, 20% by volume of fetal calf serum, 2 mM glutamine, 1× Penicillin with Streptomycin (final 1 U/ml and 1 ug/ml, respectively). For immunophenotyping of intact fetal lung tissue, week 10 lungs were fixed in paraformaldehyde and paraffin tissue sections were prepared for NKX2-1 and CD47 immunostainings.

Microarray Analysis.

Biological triplicates of all samples except human fetal lung were prepared. Biological duplicates from one embryo ("uncultured naïve lung epithelium") and a singlicate from a different embryo ("differentiated AT2 cells") were prepared for the human fetal lung sample controls. All 27 samples for microarray analysis were lysed and stored in Qiazol (Qiagen). RNA extraction was performed using RNeasy Plus Mini kit (Qiagen). Both Nanodrop and Agilent 2100 Bioanalyzer determined RNA concentration and quality. All samples had an RNA Integrity Number (RIN) score of >7.0. Affymetrix GeneChip Human Gene 2.0 ST arrays were used for gene expression profiling. Technical quality of the arrays was assessed by two quality metrics: Relative Log Expression and Normalized Unscaled Standard Error. Analyzing X and Y-lined genes established adequate dynamic range of gene expression across samples. Principal Component Analysis (PCA) was performed using the prcomp R function with expression values that had been normalized across all samples to a mean of zero and a standard deviation of one. Differential gene expression with respect to experimental group across all samples was assessed by performing a one-way ANOVA computed using the f.pvalue function in the sva package (version 3.4.0), and the significance of each pairwise comparison between groups (corrected for multiple hypothesis testing) was obtained using Tukey's Honest Significant Difference post-hoc test. Correction for multiple hypothesis testing was accomplished using the Benjamini-Hochberg false discovery rate (FDR). All statistical analyses were performed using the R environment for statistical computing (version 2.15.1). FIG. 4F was generated using GENE-E (oftware.broadinstitute.org/GENE-E/index.html). The heatmap scale was determined by the row minimum and maximum log 2 expression values in each row to convert values to colors. Heatmaps Sparkline plots (FIG. 11C-11D) were generated using Morpheus (software.broadinstitute-.org/morpheus/). For the comparison of candidate lung markers from our experiments to published human fetal lung samples (FIG. 13D) data matrix files were normalized from the NCBI GEO repository (ncbi.nlm.nih.gov/geo/, GSE14334)9. A heatmap of the log-transformed data for selected markers was generated. For samples with biological replicated or triplicates, the mean expression was calculated.

Recombination with Mouse Embryonic Lung Mesenchyme

Recombinations were performed essentially as previously described[10]. Briefly, small GFP-positive or GFP-negative fragments of day 21 hiPSC organoids were recombined with 10-12 pieces of LgM on the surface of a semisolid medium consisting of 0.5% agarose (Sigma) and 10% FBS in DMEM. The LgM rudiments were teased into close apposition to the endoderm with microsurgery knives (Fine Science Tools, Inc) and excess liquid medium was removed with a flame-drawn Pasteur pipet. After overnight culture to promote tissue adherence, the recombinants were transferred to the surface of a 8 μm pore size Whatman nucleopore filter and cultured for 5-7 days in BGJb medium containing 20% FBS, 0.2 mg/ml vitamin C (Sigma), and 5 mg/ml recombinant mouse amino-terminal SHH (R&D Systems) to promote mesenchyme viability[11]. The recombinants were maintained for 7 days, with medium changes every other day. Dexamethasone (50 nM) was added to the medium for the final 48 hours to promote lung epithelial differentiation.

Reverse Transcription Quantitative Polymerase Chain Reaction (RT-qPCR)

RNA was extracted by first lysing cells in QIAZOL™ (Qiagen) and subsequently using RNEASY™ Plus Minikit (Qiagen) according to the manufacturer's protocol. TAQMAN™ reverse transcription reagents (Applied Biosystems) were used to reverse transcribe RNA to cDNA. 2.5 μl of cDNA was added to a final volume of 25 μl of PCR reaction using TAQMAN™ Fast Universal PCR Master Mix (Applied Biosystems) in technical triplicate wells of a 96 well PCR plate and analyzed on a StepOne Real-Time PCR machine (Applied Biosystems) for 40 cycles. In some experiments, 1 μl of cDNA was used in a 20 μl PCR reaction. Relative gene expression, normalized to 18S control, was calculated as fold change in 18S-normalized gene expression, over baseline, using the $2^{(-\Delta\Delta CT)}$ method. Baseline, defined as fold change=1, was set to undifferentiated pluripotent stem cell levels, or if undetected, a cycle number of 40 was assigned to allow fold change calculations.

TABLE 3

| Gene | Vendor | Probe ID |
| --- | --- | --- |
| NFIB | ThermoFischer Scientific | Hs01029175_m1 |
| CYTL1 | ThermoFischer Scientific | Hs01573280_m1 |
| MUC1 | ThermoFischer Scientific | Hs00159357_m1 |
| SPOCK3 | ThermoFischer Scientific | Hs00213568_m1 |
| CRH | ThermoFischer Scientific | Hs01921237_s1 |
| BMP3 | ThermoFischer Scientific | Hs00609638_m1 |
| FOXP2 | ThermoFischer Scientific | Hs0036_m12818 |
| LAMA3 | ThermoFischer Scientific | Hs00165042_m1 |
| GRHL2 | ThermoFischer Scientific | Hs00227745_m1 |

TABLE 3-continued

| Gene | Vendor | Probe ID |
| --- | --- | --- |
| SEMA3C | ThermoFischer Scientific | Hs00989373_m1 |
| CD47 | ThermoFischer Scientific | Hs00179953_m1 |
| LMO7 | ThermoFischer Scientific | Hs00245600_m1 |
| ELF3 | ThermoFischer Scientific | Hs00963881_m1 |
| NKX2-1 | ThermoFischer Scientific | Hs00968940_m1 |
| SFTPC | ThermoFischer Scientific | Hs00161628_m1 |
| SFTPB | ThermoFischer Scientific | Hs01090667_m1 |
| TP63 | ThermoFischer Scientific | Hs00978343_m1 |
| PITX1 | ThermoFischer Scientific | Hs00267528_m1 |

Surface Marker Screen iPSC C17 was differentiated in the lung differentiation protocol and dissociated into a single cell suspension on day 15 of differentiation, as previously described. The BD Lyoplate Human Cell Surface Marker Screening Panel (BD Biosciences 560747) was used to screen, by flow cytometry, for the expression of 242 cell surface markers on day 15 cells according the manufacturer's instruction. The panel contains primary monoclonal mouse and rat antibodies against the 242 surface markers, appropriate isotype controls and secondary AlexaFluor 647 conjugated goat anti-mouse IgG and goat anti-rat IgG antibodies. Samples were analyzed on an BD LSR II flow cytometer. Surface marker expression (AlexaFluor 647) was plotted against NKX2-1$^{GFP+}$ to identify surface markers differentially expressed in either the NKX2-1$^{GFP+}$ or NKX2-1$^{GFP-}$ population.

Immunostaining

Day 15 cultures (FIG. 1D) and day 36 organoids (FIGS. 2A,2D) were fixed by incubating in 4% paraformaldehyde at room temperature for 10 minutes and 30 minutes respectively. Organoids were combined in low melting agarose (SeaPrep) to form a pellet and then paraffin embedded. For immunocytochemistry sections were rehydrated and antigen retrieval was performed at 95° C. for 20 minutes in Dako Target Retrieval Solution (DAKO, S-1699). For fixed cells blocking was performed with 2.5% normal donkey serum (NDS) and 0.25% Triton X-100 (Sigma, T-8787) for 30 minutes followed by 2.5% NDS for 20 minutes. Paraffin sections were blocked with 4% NDS for 30 min. Samples were incubated in primary antibody in 4-5% NDS overnight at 4° C. The staining was detected with secondary antibodies purchased from Jackson Immunoresearch (donkey anti-mouse, donkey anti-rabbit, donkey anti-chicken at 1:300 to 1:500 dilution for 2 hours at room temperature). Nuclear counterstaining was performed with DAPI (Invitrogen, 1:10,000) or SLOWFADE GOLD™ antifade reagent containing DAPI (Life Technologies, S36938). Antibodies include NKX2-1 (rabbit monoclonal, Abcam, Ab76013, 1:250), NKX2-1 (mouse monoclonal, Abcam, Ab72876, 1:100), EPCAM (mouse monoclonal, Abcam, GR224588-1, 1:250), GFP (polyclonal chicken IgY, AVES, GFP 1020, 1:10,000), Pro-SPC (polyclonal rabbit, Seven Hills, WRAB-9337, 1:100) and PAX8 (polyclonal rabbit, Abcam, Ab122944 1:50-1:100), CD47 (mouse monoclonal Abcam, Ab3283, 1:100), CD47 (mouse monoclonal FITC conjugated, Biolegend, 323106, 1:100) and SOX9 (rabbit monoclonal, Ab185230, 1:500).

In Situ Hybridization and Southern Blot

A full-length cDNA encoding human SFTPC was isolated by RT-PCR and cloned into vector pcDNA3, which was then used to transcribe digoxigenin-labeled antisense riboprobe. Whole mount in situ hybridization on tissue recombinants was performed according to the protocol described by Wilkinson[12]. Southern blot using digoxigenin (DIG)-labelled hybridization probes: PCR DIG Probe Synthesis Kit (Roche), Southern blot probe primers (5'-GACTCTAAGGGTCCGAGCAG-3' (SEQ ID NO:5) and 5'-GAGACCGGTAAGCGACAAAC-3' (SEQ ID NO: 6)) and 10 pg of NKX2-1 donor DNA were used to generate incorporated DIG-dUTP hybridization probes, by PCR labelling and following the manufacturer's instructions. Primer annealing temperature, primer and template concentrations were optimized prior to DIG-dUTP incorporation. 3.75 ug of genomic DNA samples from various unmodified, NKX2-1 targeted and Cre-excised clones were separated on a 0.7% agarose gel, transferred onto a positively charged nylon membrane (Roche) and UV crosslinked. The Southern blot was first prehybridized for 40 min at 42 degree Celsius using DIG Easy Hyb Granules (Roche) and afterwards hybridized with DIG-labeled NKX2-1 DNA probe according the manufacturer's instructions. After the hybridization and wash procedure the NKX2-1 probe on the Southern blot was detected by chemiluminescent alkaline phosphatase substrate using ready-to-use CDP Star (Roche).

Time-Lapse Microscopy

To generate time-lapse movies of differentiation in culture, NKX2-1$^{GFP}$ human C17 iPS cells (between days 19 and 21) were imaged in an 8-well plate at 37° C. and 5% C02, conditions maintained with a Controlled Environment Microscope Incubator (Nikon Instruments, Inc.) designed for live-cell imaging. Throughout, bright field images were collected every 30 minutes and fluorescent images were collected every 2 hours at 10× magnification (Plan Fluor 10×Ph1 Dll) using an Eclipse Ti-E inverted microscope (Nikon Instruments, Inc.) equipped with the "Perfect Focus System", a motorized stage, and a Clara-Echarge-coupled device (CCD) camera (Andor Technology). Each image in the time-lapse was constructed by stitching together two by two imaging fields (four total XY positions, 15% overlap) using the supplier's image acquisition software (NIS-Elements Advanced Research). Images were acquired in phase contrast configuration and in fluorescent (GFP and mCherry) channels. Filters and light sources (Nikon LED and Lumencor SPECTRA X Light Engine) were automatically controlled by the supplier's software (NIS-Elements Advanced Research).

REFERENCES FOR SUPPLEMENTAL EXPERIMENTAL PROCEDURES

1. Crane, A. M. et al. Targeted Correction and Restored Function of the CFTR Gene in Cystic Fibrosis Induced Pluripotent Stem Cells. *Stem Cell Reports* 4, 569-577 (2015).
2. Kurmann, A. A. et al. Regeneration of Thyroid Function by Transplantation of Differentiated Pluripotent Stem Cells. *Cell Stem Cell* 17, 527-542 (2015).
3. Longmire, T. A. et al. Efficient derivation of purified lung and thyroid progenitors from embryonic stem cells. *Cell Stem Cell* 10, 398-411 (2012).
4. Huang, S. X. L. et al. Efficient generation of lung and airway epithelial cells from human pluripotent stem cells. *Nat. Biotechnol.* 32, 84-91 (2014).
5. Kim, D. et al. TopHat2: accurate alignment of transcriptomes in the presence of insertions, deletions and gene fusions. *Genome Biol.* 14, R36 (2013).
6. Trapnell, C. et al. Differential gene and transcript expression analysis of RNA-seq experiments with TopHat and Cufflinks. *Nat Protoc* 7, 562-578 (2012).
7. Wade, K. C. et al. Gene induction during differentiation of human pulmonary type II cells in vitro. *Am J Respir Cell Mol Biol* 34, 727-737 (2006).
8. Gonzales, L. W., Guttentag, S. H., Wade, K. C., Postle, A. D. & Ballard, P. L. Differentiation of human pulmonary type II cells in vitro by glucocorticoid plus cAMP. *Am. J. Physiol. Lung Cell Mol. Physiol.* 283, L940-51 (2002).
9. Kho, A. T. et al. Transcriptomic analysis of human lung development. *Am. J. Respir. Crit. Care Med.* 181, 54-63 (2010).
10. Shannon, J. M., Nielsen, L. D., Gebb, S. A. & Randell, S. H. Mesenchyme specifies epithelial differentiation in reciprocal recombinants of embryonic lung and trachea. *Dev Dyn* 212, 482-494 (1998).
11. Weaver, M., Batts, L. & Hogan, B. L. M. Tissue interactions pattern the mesenchyme of the embryonic mouse lung. *Dev Biol* 258, 169-184 (2003).
12. Wilkinson, D. G. in *Whole mount in situ hybridization of vertebrate embryo* (ed. Wilkinson, D. G.) 61, 75-83 (Oxford University Press, 1992).

REFERENCES FOR TABLE 2

Attar, M. A., Bailie, M. B., Christensen, P. J., Brock, T. G., Wilcoxen, S. E. and Paine, R. (1999). Induction of ICAM-1 expression on alveolar epithelial cells during lung development in rats and humans. *Exp. Lung Res.* 25, 245-259.

Herriges, J. C., Yi, L., Hines, E. A., Harvey, J. F., Xu, G., Gray, P. A., Ma, Q. and Sun, X. (2012). Genome-scale study of transcription factor expression in the branching mouse lung. *Dev. Dyn.* 241, 1432-1453.

Li, Y. and Linnoila, R. I. (2012). Multidirectional differentiation of Achaete-Scute homologue-1-defined progenitors in lung development and injury repair. *Am J Respir Cell Mol Biol* 47, 768-775.

Lu, M. M., Li, S., Yang, H. and Morrisey, E. E. (2002). Foxp4: a novel member of the Foxp subfamily of winged-helix genes co-expressed with Foxp1 and Foxp2 in pulmonary and gut tissues. *Mech. Dev.* 119 Suppl 1, S197-202.

Maeda, Y., Davé, V. and Whitsett, J. A. (2007). Transcriptional control of lung morphogenesis. *Physiol. Rev.* 87, 219-244.

Metzger, D. E., Xu, Y. and Shannon, J. M. (2007). Elf5 is an epithelium-specific, fibroblast growth factor-sensitive transcription factor in the embryonic lung. *Dev Dyn* 236, 1175-1192.

Millien, G., Beane, J., Lenburg, M., Tsao, P.-N., Lü, J., Spira, A. and Ramirez, M. I. (2008). Characterization of the mid-foregut transcriptome identifies genes regulated during lung bud induction. *Gene Expr. Patterns* 8, 124-139.

Perkins, A. S., Mercer, J. A., Jenkins, N. A. and Copeland, N. G. (1991). Patterns of Evi-1 expression in embryonic and adult tissues suggest that Evi-1 plays an important regulatory role in mouse development. *Development* 111, 479-487.

Rankin, S. A., Kormish, J., Kofron, M., Jegga, A. and Zorn, A. M. (2011). A gene regulatory network controlling hhex transcription in the anterior endoderm of the organizer. *Dev Biol* 351, 297-310.

Zorn, A. M. and Wells, J. M. (2009). Vertebrate endoderm development and organ formation. *Annu Rev Cell Dev Biol* 25, 221-251.

INCORPORATION BY REFERENCE

The entire contents of all patents published, patent applications and other references cited herein are hereby expressly incorporated herein in their entireties by reference.

The invention claimed is:

1. A composition comprising: a population comprising at least 90% $CD47^{hi}/CD26^{lo}$ lung progenitor cells and a pharmaceutically acceptable carrier wherein the $CD47^{hi}/CD26^{lo}$ lung progenitor cells are derived from pluripotent stem cells, and wherein the composition is formulated for aerosol administration and comprises a propellant.

2. The composition of claim 1, where the $CD47^{hi}/CD26^{lo}$ lung progenitor cell also expresses NKX2-1.

3. The composition of claim 1, wherein the $CD47^{hi}/CD26^{lo}$ lung progenitor cell further expresses SFTA3, CPM, NFIB, NKX2-1, CRH, JUN, MECOM, SOX2, HES1, HOXA1, FOXA2, FOXA1, GATA6, GRHL2, IRX1, IRX2, ELF3, ELF5, HNFIB, FOXP2, HOXA4, HOXC4, SHH, EPCAM, CD166, CD227, SOX9, and/or LAMA2.

4. The composition of claim 1, wherein the $CD47^{hi}/CD26^{lo}$ lung progenitor cell comprises expression of NKX2-1, SFTA3, CPM, and LAMA3.

5. The composition of claim 1, wherein the $CD47^{hi}/CD26^{lo}$ lung progenitor cell does not express SCGB3A2, SFTPB, TP63, ICAM1, IL8, ASCL1, FOXJ1, SCGB1A1, ITGB6, SIX3, SIX6, OTX1 or PAX8.

6. The composition of claim 1, wherein the $CD47^{hi}/CD26^{lo}$ lung progenitor cell is engineered to comprise at least one genomic modification.

7. The composition of claim 1, wherein the $CD47^{hi}/CD26^{lo}$ lung progenitor cells are isolated by a method comprising:

(a) contacting a population of cells comprising lung primordial progenitor cells with an antibody that recognizes CD47 and a second antibody that recognizes CD26 to determine the level of expression of CD47 and CD26, and (b) isolating at least one cell with a cell surface phenotype comprising a CD47 expression level that is at least 20% greater than the CD47 expression level in a control cell and comprising a CD26 expression level that is at least 20% lower than the CD26 expression level in a control cell, wherein the control cell is a cell that is not committed to the lung lineage, thereby isolating a $CD47^{hi}/CD26^{lo}$ lung progenitor cell from the population of cells comprising lung primordial progenitor cells.

* * * * *